US008338380B2

(12) United States Patent
Bevec et al.

(10) Patent No.: US 8,338,380 B2
(45) Date of Patent: Dec. 25, 2012

(54) USE OF THE PEPTIDE RFMWMR AS A THERAPEUTIC AGENT

(75) Inventors: Dorian Bevec, Germering (DE); Fabio Cavalli, Beckenried (CH); Vera Cavalli, Muzzano (CH); Gerald Bacher, Germering (DE)

(73) Assignee: mondoBIOTECH Laboratories AG, Vaduz (LI)

( * ) Notice: Subject to any disclaimer, the term of this patent is extended or adjusted under 35 U.S.C. 154(b) by 304 days.

(21) Appl. No.: 12/677,290

(22) PCT Filed: Sep. 9, 2008

(86) PCT No.: PCT/EP2008/007601
§ 371 (c)(1),
(2), (4) Date: Mar. 9, 2010

(87) PCT Pub. No.: WO2009/040005
PCT Pub. Date: Apr. 2, 2009

(65) Prior Publication Data
US 2010/0204154 A1    Aug. 12, 2010

(30) Foreign Application Priority Data
Sep. 11, 2007   (EP) .................................. 07017762

(51) Int. Cl.
| *A01N 37/18* | (2006.01) |
| *A61K 38/00* | (2006.01) |
| *A61P 31/04* | (2006.01) |
| *C07K 2/00*  | (2006.01) |
| *C07K 4/00*  | (2006.01) |
| *C07K 5/00*  | (2006.01) |
| *C07K 7/00*  | (2006.01) |
| *C07K 14/00* | (2006.01) |
| *C07K 16/00* | (2006.01) |
| *C07K 17/00* | (2006.01) |

(52) U.S. Cl. .......... 514/21.8; 514/2.4; 930/20; 930/190; 530/329

(58) Field of Classification Search ....................... None
See application file for complete search history.

(56) References Cited

OTHER PUBLICATIONS

Dooley et al, Proc. Natl. Acad. Sci. USA (1993), vol. 90, pp. 10811-10815.*
Dooley et al., Acetalins: Opioid Receptor antagonists determined through the use of synthetic peptide combinatorial libraries, PNAS, vol. 90, pp. 10811-10815 (Nov. 1993).*
Peterson et al. , Morphine stimulates the phagocytosis of *Mycobacterium tuberculosis* by human microglial cells: involvement of G protein-coupled opiate receptor, Advances in Neuroimmunology, vol. 5, pp. 299-309 (2005).*
Dooley et al.,PNAS, 1993, 90: 10818.

\* cited by examiner

*Primary Examiner* — Anish Gupta
*Assistant Examiner* — Randall L Beane
(74) *Attorney, Agent, or Firm* — Winstead PC

(57) ABSTRACT

The present invention is directed to the use of the peptide compound Ac-Arg-Phe-Met-Trp-Met-Arg-$NH_2$ as a therapeutic agent for the prophylaxis and/or treatment of cancer, autoimmune diseases, fibrotic diseases, inflammatory diseases, neurodegenerative diseases, infectious diseases, lung diseases, heart and vascular diseases and metabolic diseases. Moreover the present invention relates to pharmaceutical compositions preferably in form of a lyophilisate or liquid buffer solution or artificial mother milk formulation or mother milk substitute containing the peptide Ac-Arg-Phe-Met-Trp-Met-Arg-$NH_2$ optionally together with at least one pharmaceutically acceptable carrier, cryoprotectant, lyoprotectant, excipient and/or diluent.

3 Claims, No Drawings

SEQUENCE LISTING

```
<160> NUMBER OF SEQ ID NOS: 1

<210> SEQ ID NO 1
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 1

Arg Phe Met Trp Met Arg
1               5
```

USE OF THE PEPTIDE RFMWMR AS A THERAPEUTIC AGENT

The present invention is directed to the use of the peptide compound Ac-Arg-Phe-Met-Trp-Met-Arg-NH$_2$ as a therapeutic agent for the prophylaxis and/or treatment of cancer, autoimmune diseases, fibrotic diseases, inflammatory diseases, neurodegenerative diseases, infectious diseases, lung diseases, heart and vascular diseases and metabolic diseases.

BACKGROUND OF THE INVENTION

The identification of a therapeutic compound effective for the prophylaxis and/or treatment of a disease can be based on the activity of the compound in a biological assay. A biological assay that mimics a disease causative mechanism can be used to test the therapeutic activity of a candidate peptide.

The causative mechanism of many diseases is the over activity of a biological pathway. A peptide that can reduce the activity of the biological pathway can be effective in the prophylaxis and/or treatment of the disease caused by the over activity of the biological pathway. Similarly the causative mechanism of many diseases is the over production of a biological molecule. A peptide that can reduce the production of the biological molecule or block the activity of the over produced biological molecule can be effective in the prophylaxis and/or treatment of the disease caused by the over production of the biological molecule.

Conversely, the causative mechanism of many diseases is the under activity of a biological pathway. A peptide that can increase the activity of the biological pathway can be effective in the prophylaxis and/or treatment of the disease caused by the under activity of the biological pathway. Also similarly the causative mechanism of many diseases is the under production of a biological molecule. A peptide that can increase the production of the biological molecule or mimic the biological activity of the under produced biological molecule can be effective in the prophylaxis and/or treatment of the disease caused by the under production of the biological molecule.

It is the object of the present invention to provide a compound for the prophylaxis and/or treatment of cancer, autoimmune diseases, fibrotic diseases, inflammatory diseases, neurodegenerative diseases, infectious diseases, lung diseases, heart and vascular diseases and metabolic diseases.

The object of the present invention is solved by the teaching of the independent claims. Further advantageous features, aspects and details of the invention are evident from the dependent claims, the description, and the examples of the present application.

DESCRIPTION OF THE INVENTION

The present invention relates to the use of the peptide Ac-Arg-Phe-Met-Trp-Met-Arg-NH$_2$ or the deacetylated form thereof, its use as a therapeutic in medicine and for the prophylaxis and/or treatment of cancer, autoimmune diseases, fibrotic diseases, inflammatory diseases, neurodegenerative diseases, infectious diseases, lung diseases, heart and vascular diseases and metabolic diseases. Also disclosed are pharmaceutical formulations preferably in form of a lyophilisate or liquid buffer solution or artificial mother milk formulation containing the inventive peptide. The peptide is especially useful for prophylaxis and/or treatment of *Mycobacterium tuberculosis* infection and infectious diseases caused by *Mycobacterium tuberculosis* infection selected from infectious diseases in the lung, of the central nervous system, in the lymphatic system, in the circulatory system, in the genitourinary system, of the bones, joints, and skin.

Cancer, Tumors, Proliferative Diseases, Malignancies and their Metastases

The term "cancer" as used herein refers also to tumors, proliferative diseases, malignancies and their metastases. Examples for cancer diseases are adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, non-small cell lung cancer (NSCLC), breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, squamous cell carcinoma of the head and neck (SCCHN), prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer.

The peptide of the present invention was tested using the assays described in Examples 1-7, 9-17 for their effect as active therapeutic agents in the prophylaxis and/or treatment of cancer, proliferative diseases, tumors and their metastases.

Infectious Disease

The immune system in higher vertebrates represents the first line of defense against various antigens that can enter the vertebrate body, including microorganisms such as bacteria, fungi and viruses that are the causative agents of a variety of diseases.

Despite large immunization programs, viral infections, such as influenza virus, human immunodeficiency virus ("HIV"), herpes simplex virus ("HSV", type 1 or 2), human papilloma virus ("HPV", type 16 or 18), human cytomegalovirus ("HCMV") or human hepatitis B or C virus ("HBV", Type B; "HCV", type C) infections, remain a serious source of morbidity and mortality throughout the world and a significant cause of illness and death among people with immune-deficiency associated with aging or different clinical conditions. Although antiviral chemotherapy with compounds such as amantadine and rimantadine have been shown to reduce the duration of symptoms of clinical infections (i.e., influenza infection), major side effects and the emergence of drug-resistant variants have been described. New classes of antiviral agents designed to target particular viral proteins such as influenza neuraminidase are being developed. However, the ability of viruses to mutate the target proteins represents an obstacle for effective treatment with molecules which selectively inhibit the function of specific viral polypeptides. Thus, there is need for new therapeutic strategies to prevent and treat viral infections.

Additionally, there is a need for new therapies for the prevention and treatment of bacterial infections, especially bacterial infections caused by multiple drug resistant bacteria. Currently, bacterial infections are treated with various antibiotics. Although antibiotics have and can be effective in the treatment of various bacterial infections, there are a number of limitations to the effectiveness and safety of antibiotics. For example, some individuals have an allergic reaction to certain antibiotics and other individuals suffer from serious side effects. Moreover, continued use of antibiotics for the treatment of bacterial infections contributes to formation of antibiotic-resistant strains of bacteria.

Another aspect of the present invention is directed to the use of the peptide for prophylaxis and/or treatment of infectious diseases including opportunistic infections.

Examples of infectious diseases are AIDS, alveolar hydatid disease (AHD, echinococcosis), amebiasis (*Entamoeba histolytica* infection), Angiostrongylus infection, anisakiasis, anthrax, babesiosis (*Babesia* infection), *Balantidium* infection (balantidiasis), *Baylisascaris* infection (raccoon roundworm), bilharzia (schistosomiasis), *Blastocystis hominis* infection (blastomycosis), boreliosis, botulism, Brainerd diarrhea, brucellosis, bovine spongiform encephalopathy (BSE), candidiasis, capillariasis (*Capillaria* infection), chronic fatigue syndrome (CFS), Chagas disease (American trypanosomiasis), chickenpox (Varicella-Zoster virus), *Chlamydia pneumoniae* infection, cholera, Creutzfeldt-Jakob disease (CJD), clonorchiasis (*Clonorchis* infection), cutaneous larva migrans (CLM) (hookworm infection), coccidioidomycosis, conjunctivitis, Coxsackievirus A16 (hand, foot and mouth disease), cryptococcosis, *Cryptosporidium* infection (cryptosporidiosis), *Culex* mosquito (West Nile virus vector), cyclosporiasis (*Cyclospora* infection), cysticercosis (neurocysticercosis), Cytomegalovirus infection, Dengue/Dengue fever, *Dipylidium* infection (dog and cat flea tapeworm), Ebola virus hemorrhagic fever, encephalitis, *Entamoeba coli* infection, *Entamoeba dispar* infection, *Entamoeba hartmanni* infection, *Entamoeba histolytica* infection (amebiasis), *Entamoeba polecki* infection, enterobiasis (pinworm infection), enterovirus infection (non-polio), Epstein-Barr virus infection, *Escherichia coli* infection, foodborne infection, foot and mouth disease, fungal dermatitis, gastroenteritis, group A streptococcal disease, group B streptococcal disease, Hansen's disease (leprosy), Hantavirus pulmonary syndrome, head lice infestation (pediculosis), *Helicobacter pylori* infection, hematologic disease, Hendra virus infection, hepatitis (HCV, HBV), herpes zoster (shingles), HIV Infection, human ehrlichiosis, human parainfluenza virus infection, influenza, isosporiasis (*Isospora* infection), Lassa fever, leishmaniasis, Kala-azar (Kala-azar, *Leishmania* Infection), lice (body lice, head lice, pubic lice), Lyme disease, malaria, Marburg hemorrhagic fever, measles, meningitis, mosquito-borne diseases, *Mycobacterium avium* complex (MAC) infection, *Naegleria* infection, nosocomial infections, nonpathogenic intestinal ameobae infection, onchocerciasis (river blindness), opisthorciasis (Opisthorcis infection), parvovirus infection, plague, *Pneumocystis carinii* pneumonia (PCP), polio, Q fever, rabies, respiratory syncytial virus (RSV) Infection, rheumatic fever, Rift Valley fever, river blindness (onchocerciasis), rotavirus infection, roundworm infection, salmonellosis, salmonella enteritidis, scabies, shigellosis, shingles, sleeping sickness, smallpox, streptococcal Infection, tapeworm infection (*Taenia* infection), tetanus, toxic shock syndrome, tuberculosis, ulcers (peptic ulcer disease), valley fever, *Vibrio parahaemolyticus* infection, *Vibrio vulnificus* infection, viral hemorrhagic fever, warts, waterborne infectious diseases, West Nile virus infection (West Nile encephalitis), whooping cough, yellow fever.

Another aspect of the present invention is directed to the use of the peptide for prophylaxis and/or treatment of prion diseases.

Prions are infectious agents which do not have a nucleic acid genome. It seems that a protein alone is the infectious agent. A prion has been defined as "small proteinaceous infectious particle which resists inactivation by procedures that modify nucleic acids". The discovery that proteins alone can transmit an infectious disease came as a considerable surprise to the scientific community. Prion diseases are often called "transmissible spongiform encephalopathies", because of the post mortem appearance of the brain with large vacuoles in the cortex and cerebellum. Probably most mammalian species develop these diseases. Prion diseases are a group of neurodegenerative disorders of humans and animals and the prion diseases can manifest as sporadic, genetic or infectious disorders. Examples of prion diseases acquired by exogenous infection are bovine spongiform encephalitis (BSE) of cattle and the new variant of Creutzfeld-Jakob disease (vCJD) caused by BSE as well as scrapie of animals. Examples of human prion diseases include kuru, sporadic Creutzfeldt-Jakob disease (sCJD), familial CJD (fCJD), iatrogenic CJD (iCJD), Gerstmann-Sträussler-Scheinker (GSS) disease, fatal familial insomnia (FFI), and especially the new variant CJD (m/CJD or vCJD).

The name "prion" is used to describe the causative agents which underlie the transmissible spongiform encephalopathies. A prion is proposed to be a novel infectious particle that differs from viruses and viroids. It is composed solely of one unique protein that resists most inactivation procedures such as heat, radiation, and proteases. The latter characteristic has led to the term protease-resistant isoform of the prion protein. The protease-resistant isoform has been proposed to slowly catalyze the conversion of the normal prion protein into the abnormal form.

The term "isoform" in the context of prions means two proteins with exactly the same amino acid sequence that can fold into molecules with dramatically different tertiary structures. The normal cellular isoform of the prion protein ($PrP^C$) has a high α-helix content, a low β-sheet content, and is sensitive to protease digestion. The abnormal, disease-causing isoform ($PrP^{Sc}$) has a lower a-helix content, a much higher β-sheet content, and is much more resistant to protease digestion.

As used herein the term "prion diseases" refers to transmissible spongiform encephalopathies. Examples for prion diseases comprise scrapie (sheep, goat), transmissible mink encephalopathy (TME; mink), chronic wasting disease (CWD; muledeer, deer, elk), bovine spongiform encephalopathy (BSE; cows, cattles), Creutzfeld-Jacob Disease (CJD), variant CJD (vCJD), sporadic Creutzfeldt-Jakob disease (sCJD), familial CJD (fCJD), iatrogenic CJD (iCJD, Gerstmann-Sträussler-Scheinker syndrome (GSS), fatal familial insomnia (FFI), and kuru. Preferred are BSE, vCJD, and CJD.

The peptide of the present invention was tested using the assays described in Examples 1-7 for their effect as active therapeutic agents in the prophylaxis and/or treatment of infectious diseases and disorders.

*Mycobacterium tuberculosis* infection

Tuberculosis (TB) is an often severe and contagious airborne disease caused by infection with *Mycobacterium tuberculosis* (Mtb). TB typically affects the lungs but it also may affect any other organ of the body. It is usually treated with a regimen of drugs taken for six months to two years depending on the type of infection. TB infection begins when the mycobacteria reach the pulmonary alveoli, where they invade and replicate within alveolar macrophages. Bacteria are picked up by dendritic cells, which do not allow replication, although these cells can transport the bacilli to local lymph nodes. Further spread is through the bloodstream to the more distant tissues and organs where secondary TB lesions can develop in lung apices, peripheral lymph nodes, kidneys, brain, and bone.

Tuberculosis is classified as one of the granulomatous inflammatory conditions. Macrophages, T lymphocytes, B lymphocytes and fibroblasts are among the cells that aggregate to form a granuloma, with lymphocytes surrounding the infected macrophages. The granuloma functions not only to prevent dissemination of the mycobacteria, but also provides a local environment for communication of cells of the immune system. Within the granuloma, T lymphocytes (CD4+) secrete cytokines such as interferon gamma, which activates macrophages to destroy the bacteria with which they are infected. T lymphocytes (CD8+) can also directly kill infected cells. Importantly, bacteria are not always eliminated within the granuloma, but can become dormant, resulting in a latent infection. Another feature of the granulomas of human tuberculosis is the development of cell death, also called necrosis, in the center of tubercles.

If TB bacteria gain entry to the bloodstream from an area of damaged tissue they spread through the body and set up many foci of infection, all appearing as tiny white tubercles in the tissues. This severe form of TB disease is most common in infants and the elderly and is called miliary tuberculosis. Patients with this disseminated TB have a fatality rate of approximately 20%, even with intensive treatment. In many patients the infection waxes and wanes. Tissue destruction and necrosis are balanced by healing and fibrosis. Affected tissue is replaced by scarring and cavities filled with cheese-like white necrotic material.

Difference Between Mtb Infection and TB Disease

In understanding tuberculosis, it's important to understand the difference between Mtb infection and TB disease.

Mtb Infection

It is estimated that more than one-third of the world's population has the TB bacterium in their bodies, which means they have Mtb infection. In addition, new infections are occurring at the rate of one per second. Fortunately, only a fraction of people infected with Mtb develops active TB disease. Those who do not get sick are known to have non-contagious latent TB, so-called because the bacteria are inactive or "asleep" in the body. TB bacteria can remain in this dormant state for months, years, and even decades without increasing in number and without making the person sick. Most people with latent Mtb infection will test positive on the tuberculin skin test, or their chest X-ray will show signs of latent TB. These findings indicate that they have the TB germ in their bodies, but most infected people will not develop active TB disease, may never get sick, may never show any symptoms, and may never spread the bacteria to others. However, one in ten people infected with TB bacteria, do develop active TB disease.

TB Disease

People with weakened immune systems (individuals with HIV disease, those receiving chemotherapy, or children under five years of age, for example) are at a greater risk for developing TB disease. When they breathe in TB bacteria, the bacteria settle in the lungs and start growing because the individual's immune system cannot fight the bacteria. In these people, TB disease may develop within days or weeks after the infection. However, in some other people, TB disease may develop months or years after the initial infection, at a time when the immune system becomes weak for other reasons and is no longer able to fight the bacteria.

When a person gets active TB, it means the TB bacteria are multiplying and attacking the lung(s), or other parts of the body such as the lymph nodes, bones, kidney, brain, spine, and even the skin. From the lungs, the TB bacteria move through the blood to different parts of the body. Symptoms of active disease include cough, loss of weight and appetite, fever, chills and night sweats as well as symptoms from the specific organ or system that is affected; for example, coughing up blood or sputum in TB of the lungs, or bone pain if the bacteria have invaded the bones.

TB disease usually can be cured with prompt and appropriate treatment, but it remains a major cause of death and disability in the world, particularly among persons infected with human immunodeficiency virus (HIV).

TB Bacteria are Spread Only from a Person with Active TB Disease

In people who develop active TB of the lungs, the TB skin test will often be positive. In addition, these people will show all the signs and symptoms of TB disease, and can pass the bacteria to others. Statistics show that approximately one-third of the people exposed to pulmonary TB become infected with the bacteria, but only one in ten of these infected people develop active TB disease during their lifetimes. Among people suffering from TB disease, three out of four have disease affecting the lungs. If not treated immediately, the bacteria have the potential to destroy the lungs and kill the person. Tuberculosis, which results from an infection with *Mycobacterium tuberculosis*, can usually be cured with a combination of first-line drugs taken for several months. Shown here are the four drugs in the standard regimen of first-line drugs and their modes of action. Also shown are the dates these four drugs were discovered–all more than 40 years ago.

Multidrug-Resistant Tuberculosis (MDR TB)

MDR TB is a form of drug-resistant TB in which the TB bacteria can no longer be killed by at least the two best antibiotics, isoniazid (INH) and rifampin (RIF), commonly used to cure TB. As a result, this form of the disease is more difficult to treat than ordinary TB and requires up to two years of multidrug treatment.

People may get MDR TB in two ways:
directly, if they spend time with an MDR TB patient and breathe in the MDR TB bacteria, and
if they already have active TB and do not properly follow their prescribed treatment regimen or TB medication is not reliably available to them. This inconsistent use of TB antibiotics gives the bacteria enough time to evolve and evade the first-line anti-TB medications, and regular TB may then progress to MDR TB, which is more challenging to treat.

MDR TB occurs when a *Mycobacterium tuberculosis* strain is resistant to isoniazid and rifampin, two of the most powerful first-line drugs. To cure MDR TB, healthcare providers must turn to a combination of second-line drugs, several of which are shown here. Second line drugs may have more side effects, the treatment may last much longer, and the cost may be up to 100 times more than first-line therapy. MDR TB strains can also grow resistant to second-line drugs, further complicating treatment.

Extensively Drug-Resistant Tuberculosis (XDR TB)

XDR TB is a less common form of multidrug-resistant TB in which the TB bacteria have changed enough to circumvent the two best antibiotics, isoniazid (INH) and rifampin (RIF), as well as most of the alternative drugs used against MDR TB. These second-line drugs include any fluoroquinolone, and at least one of the other three injectable anti-TB drugs: amikacin, kanamycin, or capreomycin. As a result, this form of the disease needs up to two years of extensive drug treatment and is the most challenging to treat.

People may get XDR TB in two ways:
 directly, if they spend time with an XDR TB patient and breathe in the XDR TB bacteria, and
 if they already have MDR TB or active TB, and do not properly follow their prescribed treatment regimen or TB medication is not reliably available to them. This inconsistent use of TB antibiotics gives the bacteria enough time to evolve and evade most if not all TB drugs, making it extremely difficult or impossible to treat XDR TB.

XDR TB occurs when a *Mycobacterium tuberculosis* strain is resistant to isoniazid and rifampin, two of the most powerful first-line drugs, as well as key drugs of the second line regimen—any fluoroquinolone and at least one of the three injectable drugs shown above. XDR TB strains may also be resistant to additional drugs, greatly complicating therapy.

In the European Community countries, comprising 495 million people, there are estimated 1 300 patients suffering from MDR Tuberculosis. In the USA, comprising 302 million people, there are estimated 200 patients suffering from MDR Tuberculosis.

TABLE 2

|  | New | | Previous | | Combined | |
| --- | --- | --- | --- | --- | --- | --- |
|  | N | % | N | % | N | % |
| Total number of strains tested | 9,751 | 100.0 | 537 | 100.0 | 10,288 | 100.0 |
| SUSCEPTIBLE TO ALL 4 DRUGS | 8,516 | 87.3 | 436 | 81.2 | 8,952 | 87.0 |
| ANY RESISTANCE | 1,235 | 12.7 | 101 | 18.8 | 1,336 | 13.0 |
| Isoniazid (INH) | 753 | 7.7 | 75 | 14.0 | 828 | 8.0 |
| Rifampicin (RMP) | 142 | 1.5 | 35 | 6.5 | 177 | 1.7 |
| Ethambutol (EMB) | 154 | 1.6 | 19 | 3.5 | 173 | 1.7 |
| Streptomycin (SM) | 718 | 7.4 | 46 | 8.6 | 764 | 7.4 |
| MONORESISTANCE | 859 | 8.8 | 59 | 11.0 | 918 | 8.9 |
| Isoniazid (INH) | 391 | 4.0 | 35 | 6.5 | 426 | 4.1 |
| Rifampicin (RMP) | 23 | 0.2 | 6 | 1.1 | 29 | 0.3 |
| Ethambutol (EMB) | 43 | 0.4 | 1 | 0.2 | 44 | 0.4 |
| Streptomycin (SM) | 402 | 4.1 | 17 | 3.2 | 419 | 4.0 |
| MULTIDRUG RESISTANCE | 112 | 1.1 | 28 | 5.2 | 140 | 1.4 |
| INH + RMP | 31 | 0.3 | 9 | 1.7 | 40 | 0.4 |
| INH + RMP + EMB | 9 | 0.1 | 3 | 0.6 | 12 | 0.1 |
| INH + RMP + SM | 20 | 0.2 | 5 | 0.9 | 25 | 0.2 |
| INH + RMP + EMB + SM | 52 | 0.5 | 11 | 2.1 | 63 | 0.6 |
| OTHER PATTERNS | 264 | 2.7 | 14 | 2.6 | 278 | 2.7 |
| INH + EMB | 16 | 0.2 | 1 | 0.2 | 17 | 0.2 |
| INH + SM | 212 | 2.2 | 9 | 1.7 | 221 | 2.1 |
| INH + EMB + SM | 22 | 0.2 | 2 | 0.4 | 24 | 0.2 |
| RMP + EMB | 4 | 0.1 | 0 | 0.0 | 4 | 0.1 |
| RMP + SM | 2 | 0.1 | 1 | 0.2 | 3 | 0.1 |
| RMP + EMB + SM | 1 | 0.1 | 0 | 0.0 | 1 | 0.1 |
| EMB + SM | 7 | 0.1 | 1 | 0.2 | 8 | 0.1 |
| NUMBER OF DRUGS RESISTANT TO: | | | | | | |
| susceptible to 4 drugs | 8,516 | 87.3 | 436 | 81.2 | 8,952 | 87.0 |
| resistant to 1 drug | 859 | 8.8 | 59 | 11.0 | 918 | 8.9 |
| resistant to 2 drugs | 272 | 2.8 | 21 | 3.9 | 293 | 2.8 |
| resistant to 3 drugs | 52 | 0.5 | 10 | 1.9 | 62 | 0.6 |
| resistant to 4 drugs | 52 | 0.5 | 11 | 2.0 | 63 | 0.6 |

TABLE 1

Country examples
UNITED STATES
Countrywide: 2001

PROFILE OF THE COUNTRY AND ITS CONTROL PROGRAMME

| Population in year of survey | 284,796,887 | Year N.T.P was established | 1953 | |
| --- | --- | --- | --- | --- |
| Notification all cases (rate) | 6/100,000 | Year of Rifampicin introduction | 1971 | |
| Estimated incidence (all cases) | 5.6/100,000 | Year of Isoniazid introduction | 1952 | |
| Notification new sputum smear + | 5600 | Use of Standardized Regimens | Yes | |
| Notification new sputum smear + (rate) | 2.0/100,000 | % Use of Short Course Chemotherapy | Yes | 90% |
| Treatment Success | 76% | Use of Directly Observed Therapy | Yes | 49% |
| Retreatment cases | NA | During continuation phase | Yes | |
| Retreatment as % of NTP | % | Use of Fixed Dose Combination | Yes | % |
| Estimated HIV positive TB cases | 9.0% | Treatment in private sector | Cat 3 | |
| | | Category 1: virtually all TB patients public sector | | |
| | | Category 2: <15% in private sector | | |
| | | Category 3: 15% or more in private sector | | |
| | | TB drugs available on the private market | Rx required | |

CHARACTERISTICS OF THE SURVEY/SURVEILLANCE PROGRAMME

| Study Duration | 12 Months |
| --- | --- |
| Target Area | Countrywide |
| Sampling Method | All cases |
| Culture Media | Various |
| DST Method | Various |
| Supranational Reference Laboratory | Centers for Disease Control and Prevention (CDC), Atlanta, United States of America |

TABLE 3

Germany
NUMBER OF RESISTANT STRAIN ANALYSED AT THE NRC FROM 1993-2004

| year/ M. tuberculosis strains = patients (n) | resistant to | | | | | | | Resistant M. tuberculosis strains = patients (n) |
|---|---|---|---|---|---|---|---|---|
| | INH | RMP | EMB | PZA | SM | MDR | multiple resistance | |
| 1993/2592 | 128 | 52 | 21 | 21 | n.d. | 47 | 23 | 152 |
| 1994/2495 | 158 | 72 | 33 | 43 | n.d. | 70 | 20 | 171 |
| 1995/2212 | 161 | 95 | 54 | 50 | n.d. | 87 | 34 | 186 |
| 1996/2156 | 180 | 91 | 50 | 53 | n.d. | 85 | 38 | 202 |
| 1997/2140 | 212 | 91 | 68 | 55 | n.d. | 81 | 40 | 247 |
| 1998/2311 | 273 | 118 | 72 | 48 | n.d. | 111 | 44 | 289 |
| 1999/2103 | 224 | 101 | 74 | 57 | n.d. | 92 | 63 | 253 |
| 2000/2198 | 339 | 127 | 94 | 51 | 302 | 122 | 147 (a) | 427 (b) |
| 2001/2104 | 298 | 116 | 103 | 66 | 307 | 115 | 135 | 385 |
| 2002/1985 | 305 | 113 | 93 | 49 | 325 | 105 | 149 | 418 |
| 2003/1912 | 297 | 114 | 101 | 44 | 291 | 110 | 214 | 397 |
| 2004/1878 | 315 | 117 | 91 | 59 | 287 | 109 | 131 | 394 |

(a) includes 49 SM resistant strains;
(b) includes 69 SM monoresistant strains

Currently, the treatment options are overall unsatisfactory and the disease is a ticking bomb.

The peptide of the present invention was tested using the assays described in Examples 1-7 for their effect as active therapeutic agents in the prophylaxis and/or treatment of infectious diseases and disorders.

Autoimmune Disease

Autoimmune disease refers to any of a group of diseases or disorders in which tissue injury is associated with a humoral and/or cell-mediated immune response to body constituents or, in a broader sense, an immune response to self. The pathological immune response may be systemic or organ specific. That is, for example, the immune response directed to self may affect joints, skin, myelin sheath that protects neurons, kidney, liver, pancreas, thyroid, adrenals, and ovaries.

In fact, the list of autoimmune diseases is composed of more than eighty disorders. A few autoimmune diseases such as vitiligo, in which patches of skin lose pigmentation, are merely annoying. Most others are debilitating, often progressive with time and eventually fatal. Systemic lupus erythematosus (SLE), for example, is a chronic disease in which 10-15% of patients die within a decade of diagnosis, in all but a few autoimmune diseases, the sex ratio skews towards women. For example, in SLE the ratio of female to male patients is nine to one. In one particular case, Hashimoto's disease in which the immune system attacks the thyroid gland, the ratio is fifty to one.

It has long been known that immune complex formation plays a role in the etiology and progression of autoimmune disease. For example, inflammation in patients with arthritis has long been considered to involve phagocytosis by leukocytes of complexes of antigen, antibody and complement-immune complexes. However, only now it is being recognized that inflammation caused by immune complexes in the joints (arthritis), the kidneys (glomerulonephritis), and blood vessels (vasculitis) is a major cause of morbidity in autoimmune diseases. Increased immune complex formation correlates with the presence of antibodies directed to self or so-called autoantibodies, and the presence of the latter can also contribute to tissue inflammation either as part of an immune complex or unbound to antigen (free antibody). In some autoimmune diseases, the presence of free autoantibody contributes significantly to disease pathology. This has been clearly demonstrated for example in SLE (anti-DNA antibodies), immune thrombocytopenia (antibody response directed to platelets), and to a lesser extent rheumatoid arthritis (IgG reactive rheumatoid factor). The important role of immune complexes and free autoantibodies is further demonstrated by the fact that successful treatment of certain autoimmune diseases has been achieved by the removal of immune complexes and free antibody by means of specific immunoadsorption procedures. For example, the use of an apheresis procedure in which immune complexes and antibodies are removed by passage of a patient's blood through an immunoaffinity column was approved by the U.S. FDA in 1987 for immune thrombocytopenia (ITP) and in 1999 for rheumatoid arthritis. However, currently there is no approved method for the treatment of autoimmune diseases which facilitates the elimination of immune complexes and autoantibodies by administration of a drug.

Another aspect of the etiology and progression of autoimmune disease is the role of proinflammatory cytokines. Under normal circumstances, proinflammatory cytokines such as tumor necrosis factor α (TNFα) and interleukin-1 (IL-1) play a protective role in the response to infection and cellular stress. However, the pathological consequences which result from chronic and/or excessive production of TNFα and IL-1 are believed to underlie the progression of many autoimmune diseases such as rheumatoid arthritis, Crohn's disease, inflammatory bowel disease, and psoriasis. Other proinflammatory cytokines include interleukin-6, interleukin-8, interleukin-17, and granulocyte-macrophage colony stimulating factor.

Naturally occurring CD4+CD25+ regulatory T cells (Tregs) play a critical role in the control of periphery tolerance to self-antigens. Interestingly, they also control immune responses to allergens and transplant antigens. Recent studies in animal models have shown that adoptive transfer of CD4+ CD25+ Tregs can prevent or even cure allergic and autoimmune diseases, and appear to induce transplantation tolerance. Thus, adoptive cell therapy using patient-specific CD4+ CD25+ Tregs has emerged as an individualized medicine for the treatment of inflammatory disease including allergy, autoimmune disease and transplant rejection. Furthermore, strategies to activate and expand antigen-specific CD4+

CD25+ Tregs in vivo using pharmacological agents may represent a novel avenue for drug development.

The interaction of leukocytes with the vessel endothelium to facilitate the extravasation into the tissue represents a key process of the body's defense mechanisms. Excessive recruitment of leukocytes into the inflamed tissue in chronic diseases like autoimmune disorders could be prevented by interfering with the mechanisms of leukocyte extravasation. Significant progress in elucidating the molecular basis of the trafficking of leukocytes from the blood stream to the extravascular tissue has been achieved that enables new strategies for therapeutic approaches. The multistep process of leukocyte rolling, firm adhesion and transmigration through the endothelial wall is facilitated by a dynamic interplay of adhesion receptors on both leukocytes and on endothelial cells as well as chemokines. In preclinical studies using various animal models, promising results have been obtained demonstrating that blocking of adhesion receptors of the selectin and integrin families improved the inflammation process in models of ulcerative colitis, autoimmune encephalomyelitis or contact hypersensitivity. In addition to the targeting of adhesion receptors by antibodies, small molecules that mimic epitopes of adhesion receptor ligands have been developed and successfully applied in animal models. Clinical studies revealed a limited response using antibodies to selectins or leukocyte function-associated antigen 1 (LFA-1) integrins compared with animal models. However, using humanized antibodies to the alpha 4-integrin subunit significant efficacy has been demonstrated in autoimmune diseases like psoriasis, multiple sclerosis and inflammatory bowel disease.

Examples of autoimmune diseases of the eyes are idiopathic opticus-neuritis, ophthalmia sympathica, anterior uveitis and other uveitis forms, retina degeneration, and Mooren's ulcer.

Examples of autoimmune diseases of the skin are bullous pemphigoides, chronic urticaria (autoimmune subtype), dermatitis herpetiformis (morbus Duhring), epidermolysis bullosa aquisita (EBA), acquired angioedema, herpes gestationes, hypocomplementemic urticarial vasculitis syndrome (HUVS), linear IgA-dermatosis, and pemphigus.

Examples of hematological autoimmune diseases are autoimmune hemolytic anemia, autoimmune neutropenia, Evans syndrome, inhibitor hemophilia, idiopathic thrombocytopenial purpura (ITP) and pernicious anemia.

Examples of gynecological autoimmune diseases are habitual abortion and infertility.

Examples of autoimmune diseases of the heart are congenital heart block, idiopathic dilatative cardiomyopathy, peripartum-cardiomyopathy, postcardiotomy syndrome, and postinfarct syndrome (Dressler syndrome).

Examples of autoimmune diseases of the ear, nose and throat are chronic sensorineural hearing loss and morbus Meniére.

Examples of autoimmune diseases of the colon are autoimmune enteropathy, colitis ulcerosa, indeterminant colitis, Crohn's disease and gluten-sensitive enteropathy.

Examples of autoimmune endocrinological autoimmune disorders are autoimmune polyglandular syndrome type 1, autoimmune polyglandular syndrome type 2, diabetes mellitus type 1 (IDDM), Hashimoto-thyroiditis, insulin-autoimmune-syndrome (IAS), idiopathic diabetes insipidus, idiopathic hypoparathyroidism, idiopathic Addison's disease and Graves-Basedow disease.

Examples of autoimmune diseases of the liver are autoimmune hepatitis (AIH type 1, 2 and 3), primary biliary cirrhosis (PBC), and primary sclerosing cholangitis.

Example of autoimmune diseases of the lung is Goodpasture's syndrome.

An example of an autoimmune disease of the stomach is chronic atrophic (type A) gastritis.

Examples of neurological autoimmune disorders are Guillain-Barré syndrome, IgM gammopathy-associated neuropathy, Lambert-Eaton syndrome, Miller-Fisher syndrome, multiple sclerosis, multifocal motoric neuropathy, myasthenia gravis, paraneoplastic neurological syndrome, Rasmussen's encephalitis, and stiff-man syndrome.

Examples of autoimmune diseases of the kidney are anti-TBM-nephritis, Goodpasture's syndrome/anti-GBM-nephritis, IgA-nephropathy, interstitial nephritis, and membrane proliferative glomerulonephritides.

Further diseases that may be caused by an autoimmune reaction are Behcet disease, chronic fatigue immune dysfunction syndrome (CFIDS), Cogan syndrome I, endometriosis, HELLP syndrome, Bechterew's disease, polymyalgia rheumatica, psoriasis, sarcoidosis and vitiligo.

During the last decade, new biotherapies have been developed for the treatment of systemic autoimmune diseases. The targets of these new treatments are all the steps of the immune response. These new therapies are: B lymphocyte (BL) inhibitors such as anti-CD20 monoclonal antibody, B lymphocyte stimulator (BLyS) antagonists and tolerogens of pathogenic-antibody secreting LB; inhibitors of the costimulation between antigen-presenting cells and T lymphocyte (TL) like monoclonal anti-CD40 ligand antibody or CTLA4-Ig (abatecept); TL antagonists which can inhibit the proliferation of autoreactive T cells; cytokine antagonists; chemokine and adhesin antagonists which inhibit trafficking of immunocompetent cells to target organs. These new approaches are based on a better understanding of the autoimmune response.

The peptide of the present invention was tested using the assays described in Examples 14-15 for their effect as active therapeutic agents in the prophylaxis and/or treatment of autoimmune diseases and disorders.

Fibrotic Disease

Fibrosis or fibrosis associated disorder affects the liver, epidermis, endodermis, muscle, tendon, cartilage, heart, pancreas, lung, uterus, nervous system, testis, ovary, adrenal gland, artery, vein, colon, small intestine, biliary tract, or stomach. In a further embodiment, the fibrosis or fibrosis associated disorder is interstitial lung fibrosis. In another embodiment the fibrosis or fibrosis associated disorder is the result of an infection with *schistosoma*. In another embodiment the fibrosis or fibrosis associated disorder is the result of wound healing.

Fibrosis is generally characterized by the pathologic or excessive accumulation of collagenous connective tissue. Fibrotic diseases and disorders include, but are not limited to, collagen disease, interstitial lung disease, human fibrotic lung disease (e.g., obliterative bronchiolitis, idiopathic pulmonary fibrosis, pulmonary fibrosis from a known etiology, tumor stroma in lung disease, systemic sclerosis affecting the lungs, Hermansky-Pudlak syndrome, coal worker's pneumoconiosis, asbestosis, silicosis, chronic pulmonary hypertension, AIDS associated pulmonary hypertension, sarcoidosis, and the like), fibrotic vascular disease, tubulointerstitial and glomerular fibrosis, myocardial fibrosis, arterial sclerosis, atherosclerosis, varicose veins, coronary infarcts, cerebral infarcts, myocardial fibrosis, musculoskeletal fibrosis, post-surgical adhesions, human kidney disease (e.g., nephritic syndrome, Alport's syndrome, HIV associated nephropathy, polycystic kidney disease, Fabry's disease, diabetic nephropathy, chronic glomerulonephritis, nephritis associated with systemic lupus, and the like), cutis keloid formation, progressive systemic sclerosis (PSS), primary sclerosing cholangitis (PSC), liver fibrosis, liver cirrhosis, renal fibrosis, pulmonary fibrosis, cystic fibrosis, chronic graft versus host disease, scleroderma (local and systemic), Grave's opthalmopathy, diabetic retinopathy, glaucoma, Peyronie's disease, penis fibrosis, urethrostenosis after a test using a cystoscope, inner accretion after surgery, scarring, myelofibrosis, idiopathic retroperitoneal fibrosis, peritoneal fibrosis from a known etiology, drug induced ergotism, fibrosis incident to benign or malignant cancer, fibrosis incident to microbial infection (e.g., viral, bacterial, parasitic, fungal, etc.), Alzheimer's disease, fibrosis incident to inflammatory bowel disease (including stricture formation in Crohn's disease and microscopic colitis), fibrosis induced by chemical or environmental insult (e.g., cancer chemotherapy, pesticides, radiation/cancer radiotherapy), and the like.

Diseases associated with fibrosis include lupus, graft versus host disease, scleroderma, systemic sclerosis, scleroderma-like disorders, sine scleroderma, calcinosis, Raynaud's esophageal dysfunction, sclerodactyl), telangiectasiae, hypersensitivity pneumonitis, collagen vascular disease, asthma, pulmonary arterial hypertension, glomerulonephritis, chronic obstructive pulmonary disease, fibrosis following myocardial infarction, central nervous system fibrosis following a stroke or neuro-degenerative diseases (e.g. Alzheimer's disease), proliferative vitreoretinopathy (PVR) and arthritis, silicosis, asbestos induced pulmonary fibrosis, acute lung injury and acute respiratory distress syndrome (including bacterial pneumonia induced, trauma induced, viral pneumonia induced, tuberculosis, ventilator induced, non-pulmonary sepsis induced, and aspiration induced).

Increased Number of Activated Myofibroblasts in Fibrotic Diseases

The emergence and disappearance of the myofibroblast appears to correlate with the initiation of active fibrosis and its resolution, respectively. In addition, the myofibroblast has many phenotypic features, which embody much of the pathologic alterations in fibrotic tissue, e.g. lung tissue. These features would seem to argue for an important role for the myofibroblast in the pathogenesis of fibrosis, e.g. lung fibrosis. Furthermore, the persistence of the myofibroblast may herald progressive disease, and, conversely, its disappearance may be an indicator of resolution. This in turn suggests that future therapeutic strategies targeting the myofibroblast would be productive.

Patients usually exhibit evidence of active fibrosis with increased numbers of activated fibroblasts, many of which have the phenotypic characteristics of myofibroblasts. At these sites, increased amounts of extracellular matrix deposition are evident with effacement of the normal alveolar architecture. Animal model studies show the myofibroblast to be the primary source of type I collagen gene expression in active fibrotic sites. In vitro studies show differentiation of these cells from fibroblasts under the influence of certain cytokines but indicate their susceptibility to nitric oxide mediated apoptosis. In addition to promoting myofibroblast differentiation, transforming growth factor-β1 (TGF-β1) provides protection against apoptosis. Thus, this well-known fibrogenic cytokine is important both for the emergence of the myofibroblast and its survival against apoptotic stimuli. This is consistent with the critical importance of this cytokine in diverse models of fibrosis in various tissues. In view of these properties, the persistence or prolonged survival of the myofibroblast may be the key to understanding why certain forms of lung injury may result in progressive disease, terminating in end stage disease.

Although pulmonary fibrosis has diverse etiologies, there is a common feature characteristic of this process, namely, the abnormal deposition of extracellular matrix that effaces the normal lung tissue architecture. A key cellular source of this matrix is the mesenchymal cell population that occupies much of the fibrotic lesion during the active period of fibrosis. This population is heterogeneous with respect to a number of key phenotypes. One of these phenotypes is the myofibroblast, which is commonly identified by its expression in a-smooth muscle actin and by features that are intermediate between the bona fide smooth muscle cell and the fibroblast. The de novo appearance of myofibroblasts at sites of wound healing and tissue repair/fibrosis is associated with the period of active fibrosis and is considered to be involved in wound contraction. Furthermore, the localization of myofibroblasts at sites undergoing active extracellular matrix deposition suggests an important role for these cells in the genesis of the fibrotic lesion.

Increased TGF-$\beta_1$ Family Levels in Fibrotic Diseases

The transforming growth factor-$\beta_1$ (TGF-$\beta_1$) family of proteins has the most potent stimulatory effect on extracellular matrix deposition of any cytokines so far examined. In animal models of pulmonary fibrosis enhanced TGF-$\beta_1$ gene expression is temporally and spatially related to increased collagen gene expression and protein deposition. TGF-$\beta_1$ antibodies reduce collagen deposition in murine bleomycin-induced lung fibrosis and human fibrotic lung tissue shows enhanced TGF-$\beta_1$ gene and protein expression. Several lines of evidence suggest that TGF-β is a central regulator of pulmonary fibrosis. Several animal models over expressing TGF-β showed extensive progressive fibrosis but limited inflammation, indicating that TGF-β may play a predominant role in the progression of pulmonary fibrosis. Therapeutic efforts are therefore focusing on inhibition of TGF-β activity, for instance by anti-TGF-β1-antibodies, or modulators of TGF-β1 such as pirfenidone. Pirfenidone inhibits TGF-β1 gene expression in vivo resulting in inhibition of TGF-β1-mediated collagen synthesis and appears to slow progression of IPF in patients. Other novel, promising antifibrotic agents include relaxin (inhibits TGF-β-mediated overexpression of collagen and increases collagenases), suramin (inhibits growth factors), prostaglandin E2 (inhibits collagen production) and lovastatin (blocks formation of granulation tissue by induction of fibroblast apoptosis).

Diseases involving the lung associated with increased levels of TGF-β include chronic lung disease of prematurity, idiopathic pulmonary fibrosis, rapid progressive pulmonary fibrosis, giant-cell interstitial pneumonia, acute rejection after lung transplantation, cytomegalovirus pneumonitis after lung transplantation, bronchiolitis obliterans, asbestosis, coal worker's pneumoconiosis, silicosis, histiocytosis, sarcoidosis, eosinophilic granuloma, scleroderma, systemic lupus erythematosus, lymphangioleiomyomatosis, central fibrosis in pulmonary adenocarcinoma, cystic fibrosis, chronic obstructive lung disease, and asthma.

Increased TNF-α Levels in Fibrotic Diseases

An important role of tumor necrosis factor-α (TNF-α) in interstitial fibrosis has been established using transgenic mice, which either overexpress or display a deficiency of this cytokine. Mice transgenically modified to overexpress TNF-a develop lung fibrosis. In contrast, mice null for TNF-α show marked resistance to bleomycin induced fibrosis. TNF-α can stimulate fibroblast replication and collagen synthesis in vitro, and pulmonary TNF-α gene expression rises after administration of bleomycin in mice. Soluble TNF-α receptors reduce lung fibrosis in murine models and pulmonary overexpression of TNF-α in transgenic mice is characterized by lung fibrosis. In patients with CFA or asbestosis, bronchoalveolar lavage fluid-derived macrophages release increased amounts of TNF-α compared with controls.

Increased TNF-α may induce fibrosis or fibrosis-associated conditions affecting any tissue including, for example, fibrosis of an internal organ, a cutaneous or dermal fibrosing disorder, and fibrotic conditions of the eye. Fibrosis of internal organs (e.g., liver, lung, kidney, heart blood vessels, gastrointestinal tract) occurs in disorders such as pulmonary fibrosis, idiopathic fibrosis, autoimmune fibrosis, myelofibrosis, liver cirrhosis, veno-occlusive disease, mesangial proliferative glomerulonephritis, crescentic glomerulonephritis, diabetic nephropathy, renal interstitial fibrosis, renal fibrosis in subjects receiving cyclosporin, allograft rejection, HTV associated nephropathy. Other fibrosis-associated disorders include systemic sclerosis, eosinophilia-myalgia syndrome, and fibrosis-associated CNS disorders such as intraocular fibrosis. Dermal fibrosing disorders include, for example, scleroderma, morphea, keloids, hypertrophic scars, familial cutaneous collagenoma, and connective tissue nevi of the collagen type. Fibrotic conditions of the eye include conditions such as diabetic retinopathy, post-surgical scarring (for example, after glaucoma filtering surgery and after crossed-eyes (strabismus) surgery), and proliferative vitreoretinopathy. Additional fibrotic conditions that may be treated by the methods of the present invention may result, for example, from rheumatoid arthritis, diseases associated with prolonged joint pain and deteriorated joints; progressive systemic sclerosis, polymyositis, dermatomyositis, eosinophilic fascitis, morphea, Raynaud's syndrome, and nasal polyposis.

Increased Matrix Metalloproteases Levels in Fibrotic Diseases

The abnormal extracellular matrix (ECM) remodeling observed in the lungs of patients with interstitial pulmonary fibrosis (IPF) is due, at least in part, to an imbalance between matrix metalloproteases (MMPs) and tissue inhibitor of metalloproteinases (TIMPs). Normal lung fibroblasts do not make MMP-9 in vitro, whereas fibroblasts from IPF lungs strongly express MMP-9. In addition, fibroblasts from patients with IPF express increased levels of all TIMPs. In this setting, TIMPs may play a role in apoptosis in some cell populations. In vitro studies of alveolar macrophages obtained from untreated patients with idiopathic pulmonary fibrosis showed marked increase in MMP-9 secretion compared to macrophages collected from healthy individuals. In animals models of bleomycin-induced pulmonary fibrosis MMPs have been shown to be elevated in bronchoalveolar lavage (BAL) fluid. Indeed, a synthetic inhibitor of MMP, Batimastat, has been shown to significantly reduce bleomycin-induced lung fibrosis, again pointing to the importance of MMPs in the development of this fibrotic disease in the lung. A number of studies have shown that the actions of MMPs can result in the release of growth factors and cytokines. These profibrotic factors require proteolytic processing for their activation or release from extracellular matrix or carrier proteins before they can exert their activity. In fact, the proteolytic activity processing of several key factors involved in the pathogenesis of pulmonary fibrosis such as insulin-like growth factor (IGF), TGF-$\beta_1$ and TNF-α occur through the actions of MMPs, thereby activating or releasing them from inhibitory protein-protein interactions. For example, IGFs in vivo are sequestered by six high affinity IGF binding proteins (IGFBPs1-6), preventing their ability to interact with IGF receptors. Studies examining adults and children IPF and interstitial lung disease show that beside IPF, IGFBP-3 and IFPB-2 levels are increased in IPF BAL fluid. MMPs have recently been shown to regulate the cleavage of IGF binding proteins, thereby liberating the complexed ligand to affect IGF actions in target cells. Observations have also shown that the gelatinases, MMP-9 and MMP-2 may be involved in proteolytic activation of latent TGF-β complexes. Furthermore, the MMP inhibitor Batimastat reduces MMP-9 activity in BAL fluid, which was associated with decreased amount of TGF-β and TNF-α.

Pulmonary fibrosis can be an all too common consequence of an acute inflammatory response of the lung to a host of inciting events. Chronic lung injury due to fibrotic changes can result from an identifiable inflammatory event or an insidious, unknown event. The inflammatory process can include infiltration of various inflammatory cell types, such as neutrophils and macrophages, the secretion of inflammatory cytokines and chemokines and the secretion of matrix remodeling proteinases.

Increased CCL18 Levels in Fibrotic Diseases

The expression and regulation of cysteine-cysteine (CC) chemokine ligand 18 (CCL18), a marker of alternative activation, by human alveolar macrophages (AMs) is increased in patients with pulmonary fibrosis and correlates negatively with pulmonary function test parameters. Thus, CCL18 is an ideal diagnostic marker for pulmonary fibrosis.

The peptide of the present invention was tested using the assays described in Examples 14-15 for their effect as active therapeutic agents in the prophylaxis and/or treatment of fibrotic diseases and disorders.

Inflammatory Disease

Inflammation is the final common pathway of various insults, such as infection, trauma, and allergies to the human body. It is characterized by activation of the immune system with recruitment of inflammatory cells, production of pro-inflammatory cells and production of pro-inflammatory cytokines. Most inflammatory diseases and disorders are characterized by abnormal accumulation of inflammatory cells including monocytes/macrophages, granulocytes, plasma cells, lymphocytes and platelets. Along with tissue endothelial cells and fibroblasts, these inflammatory cells release a complex array of lipids, growth factors, cytokines and destructive enzymes that cause local tissue damage.

One form of inflammatory response is neutrophilic inflammation which is characterized by infiltration of the inflamed tissue by neutrophil polymorphonuclear leukocytes (PMN), which are a major component of the host defense. Tissue infection by extracellular bacteria represents the prototype of this inflammatory response. On the other hand, various non-infectious diseases are characterized by extravascular recruitment of neutrophils. This group of inflammatory diseases includes chronic obstructive pulmonary disease, adult respiratory distress syndrome, some types of immune-complex alveolitis, cystic fibrosis, bronchitis, bronchiectasis, emphysema, glomerulonephritis, rheumatoid arthritis, gouty arthritis, ulcerative colitis, certain dermatoses such as psoriasis and vasculitis. In these conditions neutrophils are thought to play a crucial role in the development of tissue injury which, when persistent, can lead to the irreversible destruction of the normal tissue architecture with consequent organ dysfunction. Tissue damage is primarily caused by the activation of neutrophils followed by their release of proteinases and increased production of oxygen species.

Chronic obstructive pulmonary disease (COPD) is described by the progressive development of airflow limitation that is not fully reversible. Most patients with COPD have three pathological conditions; bronchitis, emphysema and mucus plugging. This disease is characterized by a slowly progressive and irreversible decrease in forced expiratory volume in the first second of expiration (FEVi), with relative preservation of forced vital capacity (FVC). In both asthma and COPD there is significant, but distinct, remodeling of airways. Most of the airflow obstruction is due to two major components, alveolar destruction (emphysema) and small airways obstruction (chronic obstructive bronchitis). COPD is mainly characterized by profound mucus cell hyperplasia. Neutrophil infiltration of the patient's lungs is a primary characteristic of COPD. Elevated levels of proinflammatory cytokines, like TNF-$\alpha$, and especially chemokines like interleukin-8 (IL-8) and growth-regulated oncogene-$\alpha$ (GRO-$\alpha$) play a very important role in pathogenesis of this disease. Platelet thromboxane synthesis is also enhanced in patients with COPD. Most of the tissue damage is caused by activation of neutrophils followed by their release of metalloproteinases, and increased production of oxygen species.

TNF-$\alpha$ has several biologic activities that are important in homeostasis as well as in pathophysiological conditions. The main sources of TNF-$\alpha$ are monocytes-macrophages, T-lymphocytes and mast cells. The finding that anti-TNF-$\alpha$ antibodies (cA2) are effective in the treatment of patients suffering from rheumatoid arthritis (RA) intensified the interest to find new TNF-a inhibitors as possible potent medicaments for RA. Rheumatoid arthritis is an autoimmune chronic inflammatory disease characterized by irreversible pathological changes of the joints. In addition to RA, TNF-$\alpha$ antagonists are also applicable to several other pathological conditions and diseases such as spondylitis, osteoarthritis, gout and other arthritic conditions, sepsis, septic shock, toxic shock syndrome, atopic dermatitis, contact dermatitis, psoriasis, glomerulonephritis, lupus erythematosus, scleroderma, asthma, cachexia, chronic obstructive lung disease, congestive heart failure, insulin resistance, lung (pulmonary) fibrosis, multiple sclerosis, Crohn's disease, ulcerative colitis, viral infections and AIDS.

The term "immunoinflammatory disorder" encompasses a variety of conditions, including autoimmune diseases, proliferative skin diseases, and inflammatory dermatoses. Immunoinflammatory disorders result in the destruction of healthy tissue by an inflammatory process, dysregulation of the immune system, and unwanted proliferation of cells. Examples of immunoinflammatory disorders are acne vulgaris; acute respiratory distress syndrome; Addison's disease; allergic rhinitis; allergic intraocular inflammatory diseases, antineutrophil cytoplasmic antibody (ANCA)-associated small-vessel vasculitis; ankylosing spondylitis; arthritis, asthma; atherosclerosis; atopic dermatitis; autoimmune hepatitis; autoimmune hemolytic anemia; autoimmune hepatitis; Behcet's disease; Bell's palsy; bullous pemphigoid; cerebral ischemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; erythema nodosum; exfoliative dermatitis; fibromyalgia; focal glomerulosclerosis; focal segmental glomerulosclerosis; giant cell arteritis; gout; gouty arthritis; graft versus host disease; hand eczema; Henoch-Schonlein purpura; herpes gestationis; hirsutism; idiopathic ceratoscleritis; idiopathic pulmonary fibrosis; idiopathic thrombocytopenic purpura; immune thrombocytopenic purpura inflammatory bowel or gastrointestinal disorders, inflammatory dermatoses; lichen planus; lupus nephritis; lymphomatous tracheobronchitis; macular edema; multiple sclerosis; myasthenia gravis; myositis; nonspecific fibrosing lung disease; osteoarthritis; pancreatitis; pemphigoid gestationis; pemphigus vulgaris; periodontitis; polyarteritis nodosa; polymyalgia rheumatica; pruritus scroti; pruritis/inflammation, psoriasis; psoriatic arthritis; pulmonary histoplasmosis; rheumatoid arthritis; relapsing polychondritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; shoulder tendinitis or bursitis; Sjogren's syndrome; Still's disease; stroke-induced brain cell death; Sweet's disease; systemic lupus erythematosus; systemic sclerosis; Takayasu's arteritis; temporal arteritis; toxic epidermal necrolysis; transplant-rejection and transplant-rejection-related syndromes; tuberculosis; type-1 diabetes; ulcerative colitis; uveitis; vasculitis; and Wegener's granulomatosis.

As used herein, "non-dermal inflammatory disorders" include, for example, rheumatoid arthritis, inflammatory bowel disease, asthma, and chronic obstructive pulmonary disease. By "dermal inflammatory disorders" or "inflammatory dermatoses" is meant an inflammatory disorder selected from psoriasis, guttate psoriasis, inverse psoriasis, pustular psoriasis, erythrodermic psoriasis, acute febrile neutrophilic dermatosis, eczema, asteatotic eczema, dyshidrotic eczema, vesicular palmoplantar eczema, acne vulgaris, atopic dermatitis, contact dermatitis, allergic contact dermatitis, dermatomyositis, exfoliative dermatitis, hand eczema, pompholyx, rosacea, rosacea caused by sarcoidosis, rosacea caused by scleroderma, rosacea caused by Sweet's syndrome, rosacea caused by systemic lupus erythematosus, rosacea caused by urticaria, rosacea caused by zoster-associated pain, Sweet's disease, neutrophilic hidradenitis, sterile pustulosis, drug eruptions, seborrheic dermatitis, pityriasis rosea, cutaneous kikuchi disease, pruritic urticarial papules and plaques of pregnancy, Stevens-Johnson syndrome and toxic epidermal necrolysis, tattoo reactions, Wells syndrome (eosinophilic cellulitis), reactive arthritis (Reiter's syndrome), bowel-associated dermatosis-arthritis syndrome, rheumatoid neutrophilic dermatosis, neutrophilic eccrine hidradenitis, neutrophilic dermatosis of the dorsal hands, balanitis circumscripta plasmacellularis, balanoposthitis, Behcet's disease, erythema annulare centrifugum, erythema dyschromicum perstans, erythema multiforme, granuloma annulare, hand dermatitis, lichen nitidus, lichen planus, lichen sclerosus et atrophicus, lichen simplex chronicus, lichen spinulosus, nummular dermatitis, pyoderma gangrenosum, sarcoidosis, subcorneal pustular dermatosis, urticaria, and transient acantholytic dermatosis.

By "proliferative skin disease" is meant a benign or malignant disease that is characterized by accelerated cell division in the epidermis or dermis. Examples of proliferative skin diseases are psoriasis, atopic dermatitis, nonspecific dermatitis, primary irritant contact dermatitis, allergic contact dermatitis, basal and squamous cell carcinomas of the skin, lamellar ichthyosis, epidermolytic hyperkeratosis, premalignant keratosis, acne, and seborrheic dermatitis. As will be appreciated by one skilled in the art, a particular disease, disorder, or condition may be characterized as being both a proliferative skin disease and an inflammatory dermatosis. An example of such a disease is psoriasis.

Symptoms and signs of inflammation associated with specific conditions include:
rheumatoid arthritis:—pain, swelling, warmth and tenderness of the involved joints; generalized and morning stiffness;
insulin-dependent diabetes mellitus-insulitis; this condition can lead to a variety of complications with an inflammatory component, including:—retinopathy, neuropathy, nephropathy; coronary artery disease, peripheral vascular disease, and cerebrovascular disease;

autoimmune thyroiditis:—weakness, constipation, shortness of breath, puffiness of the face, hands and feet, peripheral edema, bradycardia;

multiple sclerosis:—spasticity, blurry vision, vertigo, limb weakness, paresthesias;

uveoretinitis:—decreased night vision, loss of peripheral vision;

lupus erythematosus:—joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis;

scleroderma:—Raynaud's disease; swelling of the hands, arms, legs and face; skin thickening; pain, swelling and stiffness of the fingers and knees, gastrointestinal dysfunction, restrictive lung disease; pericarditis; renal failure;

other arthritic conditions having an inflammatory component such as rheumatoid spondylitis, osteoarthritis, septic arthritis and polyarthritis:—fever, pain, swelling, tenderness;

other inflammatory brain disorders, such as meningitis, Alzheimer's disease, AIDS dementia encephalitis:—photophobia, cognitive dysfunction, memory loss;

other inflammatory eye inflammations, such as retinitis:—decreased visual acuity;

inflammatory skin disorders, such as, eczema, other dermatites (e.g., atopic, contact), psoriasis, burns induced by UV radiation (sun rays and similar UV sources):—erythema, pain, scaling, swelling, tenderness;

inflammatory bowel disease, such as Crohn's disease, ulcerative colitis:—pain, diarrhea, constipation, rectal bleeding, fever, arthritis;

asthma:—shortness of breath, wheezing;

other allergy disorders, such as allergic rhinitis:—sneezing, itching, runny nose conditions associated with acute trauma such as cerebral injury following stroke-sensory loss, motor loss, cognitive loss;

heart tissue injury due to myocardial ischemia:—pain, shortness of breath;

lung injury such as that which occurs in adult respiratory distress syndrome:—shortness of breath, hyperventilation, decreased oxygenation, pulmonary infiltrates;

inflammation accompanying infection, such as sepsis, septic shock, toxic shock syndrome:—fever, respiratory failure, tachycardia, hypotension, leukocytosis;

other inflammatory conditions associated with particular organs or tissues, such as:

(i) nephritis (e.g., glomeralonephritis):—oliguria, abnormal urinalysis;

(ii) inflamed appendix:—fever, pain, tenderness, leukocytosis;

(iii) gout:—pain, tenderness, swelling and erythema of the involved joint, elevated serum and/or urinary uric acid;

(iv) inflamed gall bladder:—abdominal pain and tenderness, fever, nausea, leukocytosis;

(v) congestive heart failure:—shortness of breath, rales, peripheral edema;

(vi) Type II diabetes:—end organ complications including cardiovascular, ocular, renal, and peripheral vascular disease;

(vii) lung (pulmonary) fibrosis:—hyperventilation, shortness of breath, decreased oxygenation;

(viii) vascular disease, such as atherosclerosis and restenosis:—pain, loss of sensation, diminished pulses, loss of function; and (ix) alloimmunity leading to transplant rejection:—pain, tenderness, fever.

A human peptide is "active" in an inflammatory disease if the inhibition is >50% in one of the assays described below. Inhibition (as percentage) was calculated using the following formula: % inhibition=(1−concentration of cytokines in sample/concentration of cytokines in positive control)×100. The positive control refers to stimulated samples, not treated with substances.

The peptide of the present invention was tested using the assays described in Examples 1-7, 9-17 for their effect as active therapeutic agents in the prophylaxis and/or treatment of inflammatory diseases and disorders.

Neurodegenerative Disease

The present invention also relates generally to the fields of neurology and psychiatry and to methods of protecting the cells of a mammalian central nervous system from damage or injury.

Injuries or trauma of various kinds to the central nervous system (CNS) or the peripheral nervous system (PNS) can produce profound and long-lasting neurological and/or psychiatric symptoms and disorders. One form that this can take is the progressive death of neurons or other cells of the central nervous system (CNS), i.e., neurodegeneration or neuronal degeneration.

Neuronal degeneration as a result of, for example; Alzheimer's disease, multiple sclerosis, cerebral-vascular accidents (CVAs)/stroke, traumatic brain injury, spinal cord injuries, degeneration of the optic nerve, e.g., ischemic optic neuropathy or retinal degeneration and other central nervous system disorders is an enormous medical and public health problem by virtue of both its high incidence and the frequency of long-term sequelae. Animal studies and clinical trials have shown that amino acid transmitters (especially glutamate), oxidative stress and inflammatory reactions contribute strongly to cell death in these conditions. Upon injury or upon ischemic insult, damaged neurons release massive amounts of the neurotransmitter glutamate, which is excitotoxic to the surrounding neurons. Glutamate is a negatively charged amino acid that is an excitatory synaptic transmitter in the mammalian nervous system. Although the concentration of glutamate can reach the millimolar range in nerve terminals its extracellular concentration is maintained at a low level to prevent neurotoxicity. It has been noted that glutamate can be toxic to neurons if presented at a high concentration. The term "excitotoxicity" has been used to describe the cytotoxic effect that glutamate (and other such excitatory amino acids) can have on neurons when applied at high dosages.

Patients with injury or damage of any kind to the central (CNS) or peripheral (PNS) nervous system including the retina may benefit from neuroprotective methods. This nervous system injury may take the form of an abrupt insult or an acute injury to the nervous system as in, for example, acute neurodegenerative disorders including, but not limited to; acute injury, hypoxia-ischemia or the combination thereof resulting in neuronal cell death or compromise. Acute injury includes, but is not limited to, traumatic brain injury (TBI) including, closed, blunt or penetrating brain trauma, focal brain trauma, diffuse brain damage, spinal cord injury, intracranial or intravertebral lesions (including, but not limited to, contusion, penetration, shear, compression or laceration lesions of the spinal cord or whiplash shaken infant syndrome).

In addition, deprivation of oxygen or blood supply in general can cause acute injury as in hypoxia and/or ischemia including, but not limited to, cerebrovascular insufficiency, cerebral ischemia or cerebral infarction (including cerebral ischemia or infarctions originating from embolic occlusion and thrombosis, retinal ischemia (diabetic or otherwise), glaucoma, retinal degeneration, multiple sclerosis, toxic and ischemic optic neuropathy, reperfusion following acute ischemia, perinatal hypoxic-ischemic injury, cardiac arrest or intracranial hemorrhage of any type (including, but not limited to, epidural, subdural, subarachnoid or intracerebral hemorrhage).

Trauma or injury to tissues of the nervous system may also take the form of more chronic and progressive neurodegenerative disorders, such as those associated with progressive neuronal cell death or compromise over a period of time including, but not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases (amyotrophic lateral sclerosis), multiple sclerosis, degenerative ataxias, cortical basal degeneration, ALS-Parkinson's-dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease or spinocerebellar ataxia type 3 and olivopontocerebellar degenerations, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome) or prion diseases (including, but not limited to Creutzfeld-Jakob disease, Gerstmann-Strussler-Scheinker disease, Kuru disease or fatal familial insomnia).

In addition, trauma and progressive injury to the nervous system can take place in various psychiatric disorders, including but not limited to, progressive, deteriorating forms of bipolar disorder or schizoaffective disorder or schizophrenia, impulse control disorders, obsessive compulsive disorder (OCD), behavioral changes in temporal lobe epilepsy and personality disorders.

In one preferred embodiment the compounds of the invention would be used to provide neuroprotection in disorders involving trauma and progressive injury to the nervous system in various psychiatric disorders. These disorders would be selected from the group consisting of; schizoaffective disorder, schizophrenia, impulse control disorders, obsessive compulsive disorder (OCD) and personality disorders.

In addition, trauma and injury make take the form of disorders associated with overt and extensive memory loss including, but not limited to, neurodegenerative disorders associated with age-related dementia, vascular dementia, diffuse white matter disease (Binswanger's disease), dementia of endocrine or metabolic origin, dementia of head trauma and diffuse brain damage, dementia pugilistica or frontal lobe dementia, including but not limited to Pick's Disease.

Other disorders associated with neuronal injury include, but are not limited to, disorders associated with chemical, toxic, infectious and radiation injury of the nervous system including the retina, injury during fetal development, prematurity at time of birth, anoxic-ischemia, injury from hepatic, glycemic, uremic, electrolyte and endocrine origin, injury of psychiatric origin (including, but not limited to, psychopathology, depression or anxiety), injury from peripheral diseases and plexopathies (including plexus palsies) or injury from neuropathy (including neuropathy selected from multifocal, sensory, motor, sensory-motor, autonomic, sensory-autonomic or demyelinating neuropathies (including, but not limited to Guillain-Barre syndrome or chronic inflammatory demyelinating polyradiculoneuropathy) or those neuropathies originating from infections, inflammation, immune disorders, drug abuse, pharmacological treatments, toxins, trauma (including, but not limited to compression, crush, laceration or segmentation traumas), metabolic disorders (including, but not limited to, endocrine or paraneoplastic), Charcot-Marie-Tooth disease (including, but not limited to, type 1a, 1b, 2, 4a or 1-X linked), Friedreich's ataxia, metachromatic leukodystrophy, Refsum's disease, adrenomyeloneuropathy, ataxia-telangiectasia, Djerine-Sottas (including, but not limited to, types A or B), Lambert-Eaton syndrome or disorders of the cranial nerves).

Further indications are cognitive disorders. The term "cognitive disorder" shall refer to anxiety disorders, delirium, dementia, amnestic disorders, dissociative disorders, eating disorders, mood disorders, schizophrenia, psychotic disorders, sexual and gender identity disorders, sleep disorders, somatoform disorders, acute stress disorder, obsessive-compulsive disorder, panic disorder, posttraumatic stress disorder, specific phobia, social phobia, substance withdrawal delirium, Alzheimer's disease, Creutzfeldt-Jakob disease, head trauma, Huntington's disease, HIV disease, Parkinson's disease, Pick's disease, learning disorders, motor skills disorders, developmental coordination disorder, communication disorders, phonological disorder, pervasive developmental disorders, Asperger's disorder, autistic disorder, childhood disintegrative disorder, Rett's disorder, pervasive developmental disorder, attention-deficit/hyperactivity disorder (ADHD), conduct disorder, oppositional defiant disorder, pica, rumination disorder, tic disorders, chronic motor or vocal tic disorder, Tourette's disorder, elimination disorders, encopresis, enuresis, selective mutism, separation anxiety disorder, dissociative amnesia, depersonalization disorder, dissociative fugue, dissociative identity disorder, anorexia nervosa, bulimia nervosa, bipolar disorders, schizophreniform disorder, schizoaffective disorder, delusional disorder, psychotic disorder, shared psychotic disorder, delusions, hallucinations, substance-induced psychotic disorder, orgasmic disorders, sexual pain disorders, dyspareunia, vaginismus, sexual dysfunction, paraphilias, dyssomnias, breathing-related sleep disorder, circadian rhythm sleep disorder, hypersomnia, insomnia, narcolepsy, dyssomnia, parasomnias, nightmare disorder, sleep terror disorder, sleepwalking disorder, parasomnia, body dysmorphic disorder, conversion disorder, hypochondriasis, pain disorder, somatization disorder, alcohol related disorders, amphetamine related disorders, caffeine related disorders, *cannabis* related disorders, cocaine related disorders, hallucinogen related disorders, inhalant related disorders, nicotine related disorders, opioid related disorders, phencyclidine-related disorder, abuse, persisting amnestic disorder, intoxication, withdrawal.

The term "bipolar and clinical disorders" shall refer to adjustment disorders, anxiety disorders, delirium, dementia, amnestic and other cognitive disorders, disorders usually first diagnosed in infancy (e.g.), childhood, or adolescence, dissociative disorders (e.g. dissociative amnesia, depersonalization disorder, dissociative fugue and dissociative identity disorder), eating disorders, factitious disorders, impulse-control disorders, mental disorders due to a general medical condition, mood disorders, other conditions that may be a focus of clinical attention, personality disorders, schizophrenia and other psychotic disorders, sexual and gender identity disorders, sleep disorders, somatoform disorders, substance-related disorders, generalized anxiety disorder (e.g. acute stress disorder, posttraumatic stress disorder), panic disorder, phobia, agoraphobia, obsessive-compulsive disorder, stress, acute stress disorder, anxiety neurosis, nervousness, phobia, posttraumatic stress disorder, posttraumatic stress disorder (PTSD), abuse, obsessive-compulsive disorder (OCD), manic depressive psychosis, specific phobias, social phobia, adjustment disorder with anxious features.

Examples for disorders usually first diagnosed in infancy, childhood, or adolescence are: mental retardation, learning disorders, mathematics disorder, reading disorder, disorder of written expression, motor skills disorders, developmental coordination disorder, communication disorders, expressive language disorder, phonological disorder, mixed receptive-expressive language disorder, stuttering, pervasive developmental disorders, Asperger's disorder, autistic disorder, childhood disintegrative disorder, Rett's disorder, pervasive developmental disorder, attention-deficit/hyperactivity disorder (ADHD), conduct disorder, oppositional defiant disorder, feeding disorder of infancy or early childhood, pica, rumination disorder, tic disorders, chronic motor or vocal tic disorder, Tourette's syndrome, elimination disorders, encopresis, enuresis, selective mutism, separation anxiety disorder, reactive attachment disorder of infancy or early childhood, stereotypic movement disorder.

Examples for substance-related disorders are: alcohol related disorders, amphetamine related disorders, caffeine related disorders, *cannabis* related disorders, cocaine related disorders, hallucinogen related disorders, inhalant related disorders, nicotine related disorders, opioid related disorders, psychotic disorder, psychotic disorder, phencyclidine-related disorder, abuse, persisting amnestic disorder, anxiety disorder, persisting dementia, dependence, intoxication, intoxication delirium, mood disorder, psychotic disorder, withdrawal, withdrawal delirium, sexual dysfunction, sleep disorder.

The term "neuroprotection" as used herein shall mean; inhibiting, preventing, ameliorating or reducing the severity of the dysfunction, degeneration or death of nerve cells, axons or their supporting cells in the central or peripheral nervous system of a mammal, including a human. This includes the treatment or prophylaxis of a neurodegenerative disease; protection against excitotoxicity or ameliorating the cytotoxic effect of a compound (for example, a excitatory amino acid such as glutamate; a toxin; or a prophylactic or therapeutic compound that exerts an immediate or delayed cytotoxic side effect including but not limited to the immediate or delayed induction of apoptosis) in a patient in need thereof.

The term "a patient in need of treatment with a neuroprotective drug" as used herein will refer to any patient who currently has or may develop any of the above syndromes or disorders, or any disorder in which the patient's present clinical condition or prognosis could benefit from providing neuroprotection to prevent the development, extension, worsening or increased resistance to treatment of any neurological or psychiatric disorder.

The term "treating" or "treatment" as used herein, refers to any indicia of success in the prevention or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluations.

In some embodiments this invention provides methods of neuroprotection. In certain embodiments, these methods comprise administering a therapeutically effective amount of the peptide of the invention to a patient who has not yet developed overt, clinical signs or symptoms of injury or damage to the cells of the nervous system but who may be in a high risk group for the development of neuronal damage because of injury or trauma to the nervous system or because of some known predisposition either biochemical or genetic or the finding of a verified biomarker of one or more of these disorders.

Thus, in some embodiments, the methods and compositions of the present invention are directed toward neuroprotection in a subject who is at risk of developing neuronal damage but who has not yet developed clinical evidence. This patient may simply be at "greater risk" as determined by the recognition of any factor in a subject's, or their families, medical history, physical exam or testing that is indicative of a greater than average risk for developing neuronal damage. Therefore, this determination that a patient may be at a "greater risk" by any available means can be used to determine whether the patient should be treated with the methods of the present invention.

Accordingly, in an exemplary embodiment, subjects who may benefit from treatment by the methods and peptide of this invention can be identified using accepted screening methods to determine risk factors for neuronal damage. These screening methods include, for example, conventional work-ups to determine risk factors including but not limited to: for example, head trauma, either closed or penetrating, CNS infections, bacterial or viral, cerebrovascular disease including but not limited to stroke, brain tumors, brain edema, cysticercosis, porphyria, metabolic encephalopathy, drug withdrawal including but not limited to sedative-hypnotic or alcohol withdrawal, abnormal perinatal history including anoxia at birth or birth injury of any kind, cerebral palsy, learning disabilities, hyperactivity, history of febrile convulsions as a child, history of status epilepticus, family history of epilepsy or any seizure related disorder, inflammatory disease of the brain including lupus, drug intoxication either direct or by placental transfer, including but not limited to cocaine poisoning, parental consanguinity, and treatment with medications that are toxic to the nervous system including psychotropic medications.

The determination of which patients may benefit from treatment with a neuroprotective drug in patients who have no clinical signs or symptoms may be based on a variety of "surrogate markers" or "biomarkers".

As used herein, the terms "surrogate marker" and "biomarker" are used interchangeably and refer to any anatomical, biochemical, structural, electrical, genetic or chemical indicator or marker that can be reliably correlated with the present existence or future development of neuronal damage. In some instances, brain-imaging techniques, such as computer tomography (CT), magnetic resonance imaging (MRI) or positron emission tomography (PET), can be used to determine whether a subject is at risk for neuronal damage. Suitable biomarkers for the methods of this invention include, but are not limited to: the determination by MRI, CT or other imaging techniques, of sclerosis, atrophy or volume loss in the hippocampus or overt mesial temporal sclerosis (MTS) or similar relevant anatomical pathology; the detection in the patient's blood, serum or tissues of a molecular species such as a protein or other biochemical biomarker, e.g., elevated levels of ciliary neurotrophic factor (CNTF) or elevated serum levels of a neuronal degradation product; or other evidence from surrogate markers or biomarkers that the patient is in need of treatment with a neuroprotective drug.

It is expected that many more such biomarkers utilizing a wide variety of detection techniques will be developed in the future. It is intended that any such marker or indicator of the existence or possible future development of neuronal damage, as the latter term is used herein, may be used in the methods of this invention for determining the need for treatment with the compounds and methods of this invention.

A determination that a subject has, or may be at risk for developing, neuronal damage would also include, for example, a medical evaluation that includes a thorough history, a physical examination, and a series of relevant bloods tests. It can also include an electroencephalogram (EEG), CT, MRI or PET scan. A determination of an increased risk of developing neuronal damage or injury may also be made by means of genetic testing, including gene expression profiling or proteomic techniques. For psychiatric disorders that may be stabilized or improved by a neuroprotective drug, e.g., bipolar disorder, schizoaffective disorder, schizophrenia, impulse control disorders, etc. the above tests may also include a present state exam and a detailed history of the course of the patients symptoms such as mood disorder symptoms and psychotic symptoms over time and in relation to other treatments the patient may have received over time, e.g., a life chart. These and other specialized and routine methods allow the clinician to select patients in need of therapy using the methods and formulations of this invention. In some embodiments of the present invention peptide suitable for use in the practice of this invention will be administered either singly or concomitantly with at least one or more other compounds or therapeutic agents, e.g., with other neuroprotective drugs or antiepileptic drugs, anticonvulsant drugs. In these embodiments, the present invention provides methods to treat or prevent neuronal injury in a patient. The method includes the step of; administering to a patient in need of treatment, an effective amount of one of the peptide disclosed herein in combination with an effective amount of one or more other compounds or therapeutic agents that have the ability to provide neuroprotection or to treat or prevent seizures or epileptogenesis or the ability to augment the neuroprotective effects of the compounds of the invention.

As used herein the term "combination administration" of a compound, therapeutic agent or known drug with the peptide of the present invention means administration of the drug and the one or more compounds at such time that both the known drug and the peptide will have a therapeutic effect. In some cases this therapeutic effect will be synergistic. Such concomitant administration can involve concurrent (i.e. at the same time), prior, or subsequent administration of the drug with respect to the administration of the peptide of the present invention. A person of ordinary skill in the art would have no difficulty determining the appropriate timing, sequence and dosages of administration for particular drugs and peptide of the present invention.

The said one or more other compounds or therapeutic agents may be selected from compounds that have one or more of the following properties: antioxidant activity; NMDA receptor antagonist activity, augmentation of endogenous GABA inhibition; NO synthase inhibitor activity; iron binding ability, e.g., an iron chelator; calcium binding ability, e.g., a Ca (II) chelator; zinc binding ability, e.g., a Zn (II) chelator; the ability to effectively block sodium or calcium ion channels, or to open potassium or chloride ion channels in the CNS of a patient.

The peptide of the present invention was tested using the assays described in Examples 1-7, 9-17 for their effect as active therapeutic agents in the prophylaxis and/or treatment of neurodegenerative diseases and disorders.

Heart and Vascular Disease

Heart disease is a general term used to describe many different heart conditions. For example, coronary artery disease, which is the most common heart disease, is characterized by constriction or narrowing of the arteries supplying the heart with oxygen-rich blood, and can lead to myocardial infarction, which is the death of a portion of the heart muscle. Heart failure is a condition resulting from the inability of the heart to pump an adequate amount of blood through the body. Heart failure is not a sudden, abrupt stop of heart activity but, rather, typically develops slowly over many years, as the heart gradually loses its ability to pump blood efficiently. Risk factors for heart failure include coronary artery disease, hypertension, valvular heart disease, cardiomyopathy, disease of the heart muscle, obesity, diabetes, and/or a family history of heart failure.

Examples of cardiovascular diseases and disorders are: aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive card iomyopathy, hypertrophic cardiomyopathy, restrictive cardiomyopathy, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, cardiac hypertrophy, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, Sneddon syndrome, superior vena cava syndrome, syndrome X, tachycardia, Takayasu's arteritis, hereditary hemorrhagic telangiectasia, telangiectasis, temporal arteritis, tetralogy of Fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Vascular diseases are often the result of decreased perfusion in the vascular system or physical or biochemical injury to the blood vessel.

Peripheral vascular disease (PVD) is defined as a disease of blood vessels often encountered as narrowing of the vessels of the limbs. There are two main types of these disorders, functional disease which doesn't involve defects in the blood vessels but rather arises from stimuli such as cold, stress, or smoking, and organic disease which arises from structural defects in the vasculature such as atherosclerotic lesions, local inflammation, or traumatic injury. This can lead to occlusion of the vessel, aberrant blood flow, and ultimately to tissue ischemia.

One of the more clinically significant forms of PVD is peripheral artery disease (PAD). PAD is often treated by angioplasty and implantation of a stent or by artery bypass surgery. Clinical presentation depends on the location of the occluded vessel. For example, narrowing of the artery that supplies blood to the intestine can result in severe postprandial pain in the lower abdomen resulting from the inability of the occluded vessel to meet the increased oxygen demand arising from digestive and absorptive processes. In severe forms the ischemia can lead to intestinal necrosis. Similarly, PAD in the leg can lead to intermittent pain, usually in the calf, that comes and goes with activity. This disorder is known as intermittent claudication (IC) and can progress to persistent pain while resting, ischemic ulceration, and even amputation.

Peripheral vascular disease is also manifested in atherosclerotic stenosis of the renal artery, which can lead to renal ischemia and kidney dysfunction.

One disease in which vascular diseases and their complications are very common is diabetes mellitus. Diabetes mellitus causes a variety of physiological and anatomical irregularities, the most prominent of which is the inability of the body to utilize glucose normally, which results in hyperglycemia. Chronic diabetes can lead to complications of the vascular system which include atherosclerosis, abnormalities involving large and medium size blood vessels (macroangiopathy) and abnormalities involving small blood vessels (microangiopathy) such as arterioles and capillaries.

Patients with diabetes mellitus are at increased risk of developing one or more foot ulcers as a result of established long-term complications of the disease, which include impaired nerve function (neuropathy) and/or ischemia. Local tissue ischemia is a key contributing factor to diabetic foot ulceration.

In addition to large vessel disease, patients with diabetes suffer further threat to their skin perfusion in at least two additional ways. First, by involvement of the non-conduit arteries, which are detrimentally affected by the process of atherosclerosis, and secondly, and perhaps more importantly, by impairment of the microcirculatory control mechanisms (small vessel disease). Normally, when a body part suffers some form of trauma, the body part will, as part of the body's healing mechanism, experience an increased blood flow. When small vessel disease and ischemia are both present, as in the case of many diabetics, this natural increased blood flow response is significantly reduced. This fact, together with the tendency of diabetics to form blood clots (thrombosis) in the microcirculatory system during low levels of blood flow, is believed to be an important factor in ulcer pathogenesis.

Neuropathy is a general term which describes a disease process which leads to the dysfunction of the nervous system, and is one of the major complications of diabetes mellitus, with no well-established therapies for either its symptomatic treatment or for prevention of progressive decline in nerve function.

The thickening and leakage of capillaries caused by diabetes primarily affect the eyes (retinopathy) and kidneys (nephropathy). The thickening and leakage of capillaries caused by diabetes are also associated with skin disorders and disorders of the nervous system (neuropathy).

The eye diseases associated with diabetes are nonproliferative diabetic retinopathy, proliferative diabetic retinopathy, diabetic maculopathy, glaucoma, cataracts and the like.

Other diseases, although not known to be related to diabetes are similar in their physiological effects on the peripheral vascular system. Such diseases include Raynaud syndrome, CREST syndrome, autoimmune diseases such as erythematosis, rheumatoid disease, and the like.

As used herein, the term "peripheral vascular diseases" comprises any peripheral vascular disease including peripheral and autonomic neuropathies. Examples of "peripheral vascular disease" include peripheral arterial disease, such as chronic arterial occlusion including arteriosclerosis, arteriosclerosis obliterans and thromboangiitis obliterans (Buerger's disease), macroangiopathy, microangiopathy, diabetes mellitus, thrombophlebitis, phlebemphraxis, Raynaud's disease, Raynaud's syndrome, CREST syndrome, health hazard due to vibration, Sudeck's syndrome, intermittent claudication, cold sense in extremities, abnormal sensation in extremities, sensitivity to the cold, Meniere's disease, Meniere's syndrome, numbness, lack of sensation, anesthesia, resting pain, causalgia (burning pain), disturbance of peripheral circulation function, disturbance of nerve function, disturbance of motor function, motor paralysis, diabetic peripheral circulation disorder, lumbar spinal canal stenosis, diabetic neuropathy, shock, autoimmune disease such as erythematosis, rheumatoid disease and rheumatoid arthritis, autonomic neuropathy, diabetic autonomic neuropathy, autonomic imbalance, orthostatic hypotension, erectile dysfunction, female sexual dysfunction, retrograde ejaculation, cystopathy, neurogenic bladder, defective vaginal lubrication, exercise intolerance, cardiac denervation, heat intolerance, gustatory sweating, diabetic complication, hyperglycemia, hypoglycemia unawareness, hypoglycemia unresponsiveness; glaucoma, neovascular glaucoma, cataract, retinopathy, diabetic retinopathy, diabetic maculopathy, occlusion of retinal artery, obstruction of central artery of retina, occlusion of retinal vein, macular edema, aged macular degeneration, aged disciform macular degeneration, cystoid macular edema, palpebral edema, retinal edema, chorioretinopathy, neovascular maculopathy, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, damage of skin, skin ulcer including foot ulcer, diabetic ulcer, burn ulcer, lower leg ulcer, postoperative ulcer, traumatic ulcer, ulcer after herpes zoster, radiation ulcer, drug induced ulcer, frostbite (cold injury), chilblain, gangrene and sudden gangrene, angina pectoris/variant angiitis, coronary arteriosclerosis (chronic ischemic heart disease, asymptomatic ischemic heart disease, arteriosclerotic cardiovascular disease), myocardial infarction, heart failure, congestive heart failure and painless ischemic heart disease, pulmonary edema, hypertension, pulmonary hypertension; portal hypertension, diabetic nephropathy, decubitus, renal failure.

The peptide of the present invention was tested using the assays described in Examples 1-7, 9-17 for their effect as active therapeutic agents in the prophylaxis and/or treatment of heart and vascular diseases and disorders.

Rare or Orphan Diseases

Another aspect of the present invention is directed to the use of the peptide as a therapeutic agent for the prophylaxis and/or treatment of an autoimmune disease, a fibrotic disease, an inflammatory disease, a neurodegenerative disease, an infectious disease, or a heart and vascular disease in patients suffering from one or more of the following Rare or Orphan Diseases:

ABCD syndrome, AAE, ABSD, ACPS III, ACRP syndrome, ACS, ACTH deficiency, isolated ACTH resistance, ADANE, ADCA, ADCME, ADEM, ADLTE, ADULT syndrome, AEC syndrome, AGM2, AHDS, AIDS wasting syndrome, ALS, ALSG, AMME syndrome, ANOTHER syndrome, AOA1, AOS, APC, Autoimmune polyendocrinopathy-candidiasis-ectodermal dystrophy syndrome, APUDoma, AR-CMT, ARC syndrome, ARCA, AREDYLD syndrome, ASD, ASPED, ASPWSCR duplication, ATLD, ATR16, ATRUS syndrome, ATS-MR, AVED Aagenaes syndrome, Aarskog like syndrome, Aarskog-Ose-Pande syndrome, Aarskog-Scott syndrome, Aase syndrome, Aase-Smith syndrome, Abdominal aortic aneurysm, Aberrant left pulmonary artery, Abetalipoproteinemia, Ablepharon macrostomia syndrome, Abruzzo-Erickson syndrome, Acalvaria, Acampomelic campomelic dysplasia, Acanthamoeba keratitis, Acanthocytic disorder, Acanthocytosis, Acanthosis nigricans, Acatalasemia, Aceruloplasminemia, Achalasia, Achard Thiers syndrome, Ad Acheiropodia, Achondroplasia, Achromatopsia, Acitretin embryofetopathy, Ackerman syndrome, Acoustic neurinoma, Acquired generalized lipodystrophy, Acquired hypoprothrombinemia, Acquired ichthyosis, Acquired idiopathic sideroblastic anaemia, Acquired lipoatrophic diabates, Acquired prothrombin deficiency, Acrodermatitis enteropathica zinc deficiency type, Acrodysostosis, Acrodysplasia, Acrofacial dysostosis, Acrokeratoderma, Acrokeratoelastoidosis, Acromelanosis, Acromesomelic dwarfism, Acromicric dysplasia, Acroosteolysis dominant type, Acrorenal defect-ectodermal dysplasia-diabetes, Acrorenal syndrome, Actinic porokeratosis disseminated superficial, Actinic porokeratosis, Acute Respiratory Distress Syndrome, Acute basophilic leukaemia, Acute erythroblastic leukaemia, Acute febrile neutrophilic dermatosis, Acute inflammatory demyelinating polyradiculoneuropathy (aidp), Acute interstitial pneumonia, Acute leukaemia of ambiguous lineage, Acute leukaemia of indeterminate lineage, Acute liver failure, Acute lymphoblastic leukaemia, Acute medullary lesions, Acute megacaryoblastic leukaemia, Acute monoblastic leukaemia, Acute motor and sensory axonal neuropathy (AMSAN), Acute motor axonal neuropathy (AMAN), Acute myeloblastic leukaemia, Acute myelodysplasia with myelofibrosis, Acute myelofibrosis, Acute myeloid leukaemia in Down syndrome, Acute myelomonocytic leukaemia, Acute myelosclerosis, Acute non lymphoblastic leukaemia, Acute panmyelosis with myelofibrosis, Acute peripheral arterial occlusion, Acute promyelocytic leukaemia, Acute tubulointerstitial nephritis and uveitis syndrome, Adactylia unilateral, Adamantinoma, Adams nance syndrome, Adams-Oliver syndrome, Addison's disease, Adenine phosphoribosyltransferase deficiency, Adenosine deaminase deficiency, Adenosylcobalamin deficiency, Adenovirus infection in immunocompromised patients, Adenylosuccinase deficiency Adhesive arachnoiditis, Adie syndrome, Adrenal adenoma, Adrenal hyperplasia, Adrenal incidentaloma, Adrenal insufficiency, Adrenocortical carcinoma, Adrenoleukodystrophy, Adrenomyeloneuropathy, Adrenomyodystrophy, Adult Onset Still's disease, Adult T-cell leukaemia/lymphoma, Adult idiopathic neutropenia, Adult neuronal ceroid lipofuscinosis (Kufs disease, CLN4), Adult spinal muscular atrophy, Afibrinogenemia, African tick typhus, African trypanosomiasis, Agammaglobulinemia, Age-related macular degeneration, Ahn-Lerman-Sagie syndrome, Ahumada-Del Castillo syndrome, Aicardi syndrome, Aicardi-Goutieres syndrome, AIDS, Akaba hayasaka syndrome, Akesson syndrome, Alagille syndrome, Alanine-glyoxylate aminotransferase deficiency (hyperoxaluria type 1), Albers-Schonberg disease, Albright hereditary osteodystophy, Alcock syndrome, Aldolase A deficiency, Aldosterone synthase deficiency, Aldred syndrome, Alexander disease, Algodystrophy, Alkaptonuria, Alkylglycerone phosphate synthase deficiency, Allan-Herndon-Dudley syndrome, Allergic bronchopulmonary aspergillosis, Allgrove syndrome, Alopecia, Alpers syndrome, Alpers-Huttenlocher syndrome, Alpha-thalassemia, Alport syndrome, Alström syndrome, Alternating hemiplegia, Alveolar echinococcosis, Alves dos santos castello syndrome, Alzheimer disease, Amaurosis-hypertrichosis, Ambras syndrome, Amegacaryocytosis, Amelia, Aminoaciduria, Amoebiasis due to Entamoeba histolytica, Ampola syndrome, Amyloid cardiopathy, Amyloid nephropathy, Amyloid polyneuropathy, Amyloidosis, Amylopectinosis, Amyoplasia congenita, Amyotrophic lateral sclerosis, Amyotrophy fat tissue anomaly, Anemia, Anauxetic dysplasia, Ancylostomiasis, Andermann syndrome, Andersen disease, Aneurysmal subarachnoid haemorrhage, Angelman syndrome, Angio-osteohypertrophic syndrome, Angiodysgenetic necrotizing myelopathy, Angioedema, Angiofollicular ganglionic hyperplasia, Angiokeratoma, Angioma and vascular malformation, Angiomatosis systemic cystic seip syndrome, Angioneurotic oedema, Angiostrongyliasis, Anguillulosis, Aniridia, Anisakiasis, Ankylosing spondylarthritis, Ankylostomiasis, Annuloaortic ectasia, Anodontia, Anonychia, Anophthalmia—heart and pulmonary anomalies, Anorchidia, Anorexia nervosa, Anotia, Antenatal Epstein-Barr virus infection, Anterior horn cell disease, Anti-phospholipid syndrome, Antinolo nieto borrego syndrome, Antiplasmin deficiency, Antithrombin deficiency, Antley-Bixler syndrome, Anyane-Yeboa syndrome, Aorta coarctation, Aorta hypoplasia, Aorta-pulmonary artery fistula, Aortic aneurysm syndrome, due to TGFbeta receptors anomalies, Aortic malformation, Aortic valve atresia, Aortic valve dysplasia, Aortic valve stenosis, APECED syndrome, Apert syndrome, Aphasia, Apical ballooning syndrome, Aplasia cutis, Aplastic anaemia, Apnea of infancy (AOI), Apnea of prematurity (AOP), Apo A-I deficiency, Apolipoprotein Al amyloidosis, Apple peel syndrome, Apraxia, Arbovirus fever, Arena syndrome, Areolar atrophy of the macula, Argyria, Argyrophilic grain disease, Arhinia choanal atresia microphthalmia, Arkless-Graham syndrome, Armfield syndrome, Arndt-Gottron disease, Arnold-Chiari malformation, Aromatase deficiency, Arrhinia, Arrhythmogenic right ventricular dysplasia, Arterial calcification, Arterial duct anomalies, Arterial occlusive disease, Arterial tortuosity, Arteriohepatic dysplasia, Arthritis juvenile, Arthrogryposis, Arthroophtalmopathy, Arthropathy, Arts syndrome, Asbestosis, Ascher syndrome, Aseptic abscesses syndrome, Aseptic osteitis, Asherman's syndrome, Aspartylglucosaminidase deficiency, Asperger syndrome, Aspergillosis, Asphyxiating thoracic dystrophy of the newborn, Astley-Kendall dysplasia, Astrocytoma, Ataxia, Atelencephaly, Atelosteogenesis, Atherosclerosis, Atkin-Flaitz syndrome, Atransferrinemia, Atresia, Atrial cardiomyopathy, Atrial myxoma, Atrial septal defect, Atrichia, Atrioventricular canal complete-fallot tetralogy, Atrophia aerata, Atrophoderma vermiculata, Atypical Mole syndrome, Atypical Werner syndrome, Aughton sloan milad syndrome, Aughton-Hufnagle syndrome, Ausems wittebol post hennekam syndrome, Autism, Autoimmune haemolytic anemia, Autoimmune lymphoproliferative syndrome, Autoimmune pancreatitits, Axenfeld-Rieger syndrome, Ayazi syndrome, B-cell chronic lymphocytic leukaemia, BAFME, BBB syndrome, X-linked, BCD, BEEC, BES, BIDS syndrome, BOD syndrome, BOFS, BOR syndrome, BOS syndrome, BPD, BRESEK syndrome, BRESHECK syndrome, BRIC, BS, BSCL, BTHS, BTK-deficiency, Babesiosis, Bacterial toxic-shock syndrome, Bahemuka brown syndrome, Baird syndrome, Balantidiasis, Ballard syndrome, Baller-Gerold syndrome, Ballooning cardiomyopathy, Balo diseases, Bamforth syndrome, Bangstad syndrome, Banti syndrome, Bannayan-Riley-Ruvalcaba syndrome, Barachydactyly type A4, Baraitser burn fixen syndrome, Baraitser-Brett-Piesowicz syndrome, Barakat syndrome, Barber-Say syndrome, Bardet-Biedl syndrome, Bare lymphocyte syndrome, Barnicoat baraitser syndrome, Barraquer-Simons syndrome, Barrett eosophagus, Barth syndrome, Bartonellosis, Bartsocas-Papas syndrome, Bartter syndrome, Basan syndrome, Bassen-Kornzweig disease, Bassoe syndrome, Battaglia neri syndrome, Batten disease, Baughman syndrome, Bazex syndrome, Bazex-Dupre-Christol syndrome, Bazopoulou kyrkanidou syndrome, Bd syndrome, Beals syndrome, Beals-Hecht syndrome, Bean syndrome, Beare stevenson syndrome, Bechterew syndrome, Beckwith-Wiedemann, Beemer-Ertbruggen syndrome, Behcet disease, Behr syndrome, Behrens-Baumann-Vogel syndrome, Bell's palsy, Bellini-Chiumello-Rimoldi syndrome, Benallegue Lacete syndrome, Bejel, Bencze syndrome, Bennion-Patterson syndrome, Benson's syndrome, Beradinelli-Seip syndrome, Berdon syndrome, Berger disease, Berk tabatznik syndrome, Berlin breakage syndrome, Bernard-soulier syndrome, Berylliosis, Besnier-Boeck-Schaumann disease, Bessel-Hagen disease, Best disease, Beta thalassemia, Bethlem myopathy, Bickel-Fanconi glycogenosis, Bickers-Adams syndrome, Bickerstaffs brainstem encephalitis, Bicuspid aortic valve, Biemond syndrome, Biermer disease, Bietti's crystalline dystrophy, Bile acid synthesis defect, Bile duct cancer, Biliary atresia, Biliary inflammatory disease, Bilineal acute leukaemia, Billard-Toutain-Maheut syndrome, Binder syndrome, Bindewald-Ulmer-Muller syndrome, Binswanger disease, Birt-Hogg-Dube syndrome, Bixler christian gorlin syndrome, Bjornstad syndrome, Blackfan-Diamond anaemia, Blaichman syndrome, Blake's pouch cyst, Blau syndrome, Blepharophimosis, Blepharoptosis, Blepharospasm, Blethen wenick hawkins syndrome, Bloch-Sulzberger syndrome, Bloom syndrome, Blount disease, Blue Diaper syndrome, Bohring syndrome, Bohring-Opitz syndrome, Boichis syndrome, Bone disease with defective bone mineralisation, Bone disease with increased bone density, Bone marrow failure, Bonneau-Beaumont syndrome, Bonnemann-Meinecke-Reich syndrome, Bonnet-Dechaume-Blanc syndrome, Book syndrome, Boomerang dysplasia, Booth haworth dilling syndrome, Borjeson-Forssman-Lehmann syndrome, Bork syndrome, Bornholm eye disease, Bosley-Salih-Alorainy syndrome, Bosma henkin christiansen syndrome, Bothnia retinal dystrophy, Boucher-Neuhauser syndrome, Bournevolle syndrome, Boutonneuse fever, Bouwes Bavinck syndrome, Bowen syndrome, Boyadjiev-Jabs syndrome, Boylan dew syndrome, Brachman-de Lange syndrome, Brachydactyly-arterial hypertension, Brachymesophalangy II and V, Brachyolmia, Braddock carey syndrome, Bradyopsia, Brain inflammatory disease, Brain injury, Brain sclerosis, Brauer syndrome, Braun bayer syndrome, Braun-Tinschert, Breast cancer, Brill-Zinsser disease, Brittle bone disease, Brody myopathy, Bronchial carcinoid tumour, Bronchiectasis, Bronchiolitis obliterans organizing pneumonia, Bronchiolitis obliterans with obstructive pulmonary disease, Bronchogenic cyst, Bronchopulmonary dysplasia, Bronspiegel-Zelnick syndrome, Brooke-Spiegler syndrome, Brown-Vialetto-van Laere syndrome, Bruce winship syndrome, Brucellosis, Bruck syndrome, Brugada syndrome, Brunner-Winter syndrome, Brunzell syndrome, Bruyn scheltens syndrome, Buckley syndrome, Budd-Chiari syndrome, Buerger's disease, Bull-Nixon syndrome, Bulldog syndrome, Bulimia, Bullous systemic lupus erythematosus, Buntinx lormans martin syndrome, Burkitt lymphoma, Burn-McKeown syndrome, Burning Mouth syndrome, Buschke-Fischer-Brauer syndrome, Buschke-Ollendorff syndrome, Buttiens-Fryns syndrome, C syndrome, CACD, CACH syndrome, CADASIL, CAMAK syndrome, CAMFAK syndrome, CAMOS syndrome, CANOMAD syndrome, CAP syndrome, CAPOS syndrome, CAPS (cryopyrin associated periodoc syndrome), CAR syndrome, CATCH 22, CATSHL syndrome, CAVC, CCFDN, CCGE syndrome, CDA type 1, CDG syndrome, CDGIIc, CDP, CDPD, CEDNIK syndrome, CFC syndrome, CHAND syndrome, CREST syndrome, CRMO, CRV, CSD, CSID, CSWSS syndrome, CVID, Cacchi-Ricci disease, Cafe au lait spots syndrome, Caffey disease, Cahmr syndrome, Calcinosis, Calderon gonzalez cantu syndrome, Calpainopathy, Camera lituania cohen syndrome, Campomelia Cumming type, Camptodactyl), Camurati engelmann disease, Canale-Smith syndrome, Canavan disease, Candidiasis, Cantalamessa baldini ambrosi syndrome, Canthus, Carbohydrate metabolism disorder, Cardiogenital syndrome, Cardiomyopathy, Cardioskeletal myopathy, Carey fineman ziter syndrome, Carnevale canun mendoza syndrome, Carnevale-Hernandez-del Castillo syndrome, Carnevale-Krajewska-Fischetto syndrome, Carney complex, Carney-Stratakis syndrome, Carnosinase deficiency, Carnosinemia, Caroli's disease, Carpal Tunnel syndrome, Carpenter syndrome, Carpenter-Waziri syndrome, Carrington's disease, Carrion disease, Carvajal syndrome, Casamassima-Morton-Nance syndrome, Cassia Stocco dos Santos syndrome, Castleman disease, Castro gago pombo novo syndrome, Catalase deficiency, Cataract, Catel-Manzke syndrome, Cayler syndrome, Celiac disease, Celosomia, Cenani lenz syndactylism, Central neurocytoma, Cephalopolysyndactyl), Ceramidase deficiency, Cerebellar hypoplasia, Cerebral arteriovenous shunt, Cerebral hemorrhage with amyloidosis, Cerebroretinal vasculopathy, Cfc syndrome, Chagas disease, Chanarin disease, Chandler syndrome, Chang-Davidson-Carlson syndrome, Chaotic atrial tachycardia, Char douglas dungan syndrome, Char syndrome, Charge syndrome, Charlevoix disease, Charlie m syndrome, Chediak-Higashi like syndrome, Cheilitis glandularis, Chemke oliver mallek syndrome, Chemodectoma, Cherry-red-spot myoclonus syndrome, Cherubism, Chiari Frommel syndrome, Chitayat haj chahine syndrome, Chitayat moore del bigio syndrome, Chitayat-Meunier-Hodgkinson syndrome, Chitty hall webb syndrome, Chitty-Hall-Baraitser syndrome, Cholera, Cholestasis, Cholesteryl ester storage disease, Choline acetyltransferase (ChAT) deficiency, Chondrocalcinosis, Chondrodysplasia, Chondrodystrophy, Chordoma, Choreoacanthocytosis, Chorioretinal atrophy, Choristoma, Choroidal dystrophy, Choroidal sclerosis, Choroideremia, Christ-Siemens-Touraine syndrome, Christian syndrome, Christian-Rosenberg syndrome, Christianson syndrome, Christianson-Fourie syndrome, Christmas tree syndrome, Chromomycosis, Chronic eosinophilic pneumonia, Chronic fatigue syndrome, Chronic inflammatory demyelinating polyneuropathy, Chronic myeloproliferative disease, Chronic neutrophilic leukaemia, Chronic pain requiring intraspinal analgesia, Chronic pneumonitis of infancy, Chronic osteomyelitis, Chronic spinal muscular atrophy, Chudley rozdilsky syndrome, Chudley-Lowry-Hoar syndrome, Churg-Strauss syndrome, Chylomicron retention disease, Ciliary dysentery, Ciliary dyskinesia-bronchiectasis, Cilliers-Beighton syndrome, Cirrhosis associated cardiac dysfunction, Cirrhotic cardiomyopathy, Clarkson disease, Classical Hodgkin disease, Classical homocystinuria, Claude-Bernard-Horner syndrome, ClaytonSmith-Donnai syndrome, Cleido rhizomelic syndrome, Cleidocranial dysostosis, Cleidocranial dysplasia, Clouston syndrome, Coagulation disorder, Coarctation of aorta, Coats disease, Cobb syndrome, Cocaine poisoning, Cockayne syndrome, Codas syndrome, Coeliac disease, Coenzyme Q cytochrome c reductase deficiency, Coffin syndrome, Coffin-Lowry syndrome, Coffin-Siris syndrome, Cogan syndrome, Cogan-reese syndrome, Cohen hayden syndrome, Cohen lockood wyborney syndrome, Cohen syndrome, Cole carpenter syndrome, Colitis, Collagen anomaly, Collins pope syndrome, Collins sakati syndrome, Coloboma, Colon cancer, Colonic atresia, Colorado tick encephalitis, Combined pituitary hormone deficiencies, Complement component deficiency, Congenital Lambert-Eaton-like syndrome, Congenital leptin deficiency, Congenital lobar emphysema, Conjunctival disease, Conjunctival vascular anomaly, Conn syndrome, Connective tissue disease, Conradi-Hunermann-Happle syndrome, Constrictive bronchiolitis, Cooks syndrome, Cooley anaemia, Cooper-Jabs syndrome, Cormier rustin munnich syndrome, Corneal dystrophy, Cornelia de Lange syndrome, Corneodermatoosseous syndrome, Corneogoniodysgenesis, Coronaro-cardiac fistula, Coronary arterial malformations, Coronary artery aneurysm, Coronary sinus type ASD, Cortada koussef matsumoto syndrome, Costeff optic atrophy syndrome, Costeff syndrome, Costello syndrome, Cote katsantoni syndrome, Cousin-Walbraum-Cegarra syndrome, Cowchock syndrome, Cowchock-Wapner-Kurtz syndrome, Cowden syndrome, Coxoauricular syndrome, Cramer-Niederdellmann syndrome, Crandall syndrome, Crane heise syndrome, Cranial malformation, Craniopharyngioma, Craniorachischisis, Craniostenosis, Craniosynostosis, Craniotelencephalic dysplasia, Craniotubular syndrome, Creatine deficiency, Creeping disease, Creutzfeldt-Jakob disease, Cri du chat syndrome, Crigler-Najjar syndrome, Crimean-Congo haemorragic fever (CCHF), Crisponi syndrome, Criss-cross heart, Criswick-Schepens syndrome, Crohn disease, Crome syndrome, Cronkhite canada syndrome, Cross syndrome, Crouzon disease, Crow-Fukase syndrome, Cryoglobulinaemia mixed, Cryptococcosis, Cryptogenic organizing pneumonia, Cryptophthalmia, Cryptosporidiosis, Culler-Jones syndrome, Currarino triad, Curry-Hall syndrome, Curry-Jones syndrome, Cushing disease, Cutaneomeningospinal angiomatosis, Cutaneous lupus erythematosus, Cutaneous mastocytoma, Cutaneous mastocytosis, Cutaneous photosensitivity colitis, Cutaneous vasculitis, Cutaneuous myiasis, Cutis laxa, Cutler bass romshe syndrome, Cyclosporosis, Cystathioninuria, Cystic fibrosis, Cystic hamartoma of lung and kidney, Cystic lymphangioma, Cystic renal disease, Cystinosis, Cystinuria, Cytochrome c oxydase deficiency, Cytomegalovirus (CMV) disease in patients with impaired cell mediated immunity deemed at risk, Cytopenia, Czeizel brooser syndrome, Czeizel losonci syndrome, D ercole syndrome, D-2-hydroxyglutaricaciduria, D-glycerate dehydrogenase deficiency (hyperoxaluria type 2), D-glycerate kinase deficiency, D-glycericacidemia, DCMA syndrome, DCMD, DEND syndrome, DI-CMT, DIDMOAD syndrome (Diabetes Insipidus-Diabetes Mellitus-Optic Atrophy-Deafness), DIS, DK phocomelia syndrome, DKC, DOOR syndrome, DORV, DTDP1, DYT6, Da silva syndrome, Dacryocystitis osteopoikilosis, Daentl-Townsend-Siegel syndrome, Dahlberg-Borer-Newcomer syndrome, Daish hardman lamont syndrome, Dancing Eye syndrome, Dandy walker malformation, Daneman davy mancer syndrome, Danon disease, Darier disease, Darier-Gottron disease, Davenport donlan syndrome, David syndrome, Davies disease, Davis lafer syndrome, De Barsy syndrome, De Hauwere-Leroy-Adriaenssens syndrome, De Santis-Cacchione syndrome, De Smet-Fabry-Fryns syndrome, De Vaal disease, De la Chapelle dysplasia, De morsier syndrome, Deafness-small bowel diverticulosis-neuropathy, Deal barratt dillon syndrome, Degos disease, Dejerine-Sottas syndrome, Dekaban-Arima syndrome, Delayed graft function after organ transplantation, Delleman-Oorthuys syndrome, Dementia associated with a metabolic disease, Dementia associated with a neurodegenerative disease, Dementia associated with an infectious disease, Dementia associated with hepatic and renal failure, Demodicidosis, Dendritic cell sarcoma, Dendritic cell tumor, Dengue, Dennis cohen syndrome, Dennis fairhurst moore syndrome, Dense (delta) granule disease, Dent disease, Dentin dysplasia, Denys-Drash syndrome, Der Kaloustian-Jarudi-Khoury syndrome, Der kaloustian mcintosh silver syndrome, Dercum's disease, Dermatofibrosarcoma protuberans, Dermatologic allergic disease, Dermatostomatitis Stevens Johnson type, Desbuquois syndrome, Desminopathy, Desmoid disease, Desmosterolosis, Devic's disease, Devriendt legius fryns syndrome, Devriendt vandenberghe fryns syndrome, DiGeorge syndrome, Diabetes, Dialysis-related arthropathy, Diaphanospondylodysostosis, Diaphragmatic agenesia, Diaphragmatic spinal muscular atrophy, Diffuse alveolar haemorrhage, Diffuse large B cell lymphoma, Diffuse leiomyomatosis-Alport syndrome X-linked, Diffuse neonatal haemangiomatosis, Dihydropyrimidinuria, Dilated cardiomyopathy with ataxia, Dincsoy-Salih-Patel syndrome, Dinno shearer weisskopf syndrome, Diomedi bernardi placidi syndrome, Dionisi-Vici-Sabetta-Gambarara syndrome, Diphtheria, Diprosopia, Discoid lupus erythematosus, Discrete fibromuscular subaortic stenosis, Distichiasis-congenital heart defects-peripheral vascular anomalies, Distomatosis, Dobrow syndrome, Donath-Landsteiner syndrome, Donnai-Barrow syndrome, Donohue syndrome, Doose syndrome, Dorfman-chanarin disease, Dowling-Degos disease, Dowling-Degos-Kitamura disease, Down syndrome, Doyne honeycomb retinal dystrophy (DHRD), Drachtman weinblatt sitarz syndrome, Drash syndrome, Dravet syndrome, Drummond syndrome, Du Pan syndrome, Duane syndrome, Dubin-Johnson syndrome, Dubowitz syndrome, Duhring brocq disease, Duker-Weiss-Siber syndrome, Dunnigan syndrome, Dupont sellier chochillon syndrome, Dyggve-Melchior-Clausen disease, Dykes-Markes-Harper syndrome, Dyschondrosteosis, Dyschromatosis universalis, Dysferlinopathy, Dysfibrinogenemia, Dyskeratosis, Dysmorphic syndrome with connective tissue involvement, Dysosteosclerosis, Dysostosis, Dysphagia lusoria, Dysplasia, Dysprothrombinemia, Dyssegmental dysplasia glaucoma, Dysspondyloenchondromatosis, Dystoni-like syndrome with paroxysmal disease, Dystonia, EBD, EBJ, EBS, ECP syndrome, EDS III, EEC syndrome, EEM syndrome, EGE, ENT, ERA, ESS1, Eagle-Barret syndrome, Eales disease, Ebola virus disease, Echinocytic disorder, Ectodermal dysplasia, Ectromelia, Ectropion, Eczema-thrombocytopenia-immunodeficiency syndrome, Edinburgh malformation syndrome, Edward syndrome, Edwards-Patton-Dilly syndrome, Ehlers-Danlos syndrome, Ehrlichiosis, Eiken syndrome, Eisenmenger syndrome, Elastosis perforans serpiginosa, Elejalde syndrome, Elliott ludman teebi syndrome, Elliptocytosis, Ellis Van Creveld syndrome, Ellis yale winter syndrome, Elsching syndrome, Emanuel syndrome, Emery-Dreifuss muscular dystrophy, Emery-Nelson syndrome, Empty Sella syndrome, Encephalitis, Encephalomyelitis, Encephalopathy, Enchondromatosis, Endometriosis, Endotheliitis, Eng strom syndrome, Engel congenital myasthenia, Engelhard yatziv syndrome, Enolase deficiency, Enteric anendocrinosis, Enteropathy, Enterovirus antenatal infection, Entropion, Envenomization, Eosinophilic endocarditis, Eosinophilic pneumonia, Ependymoma, Epidermolysis bullosa, Epilepsy, Epiphyseal dysplasia, Episodic ataxia, Epispadias, Epithelial ovarian cancer, Epithelioma, Epstein-Barr virus infection, Erdheim disease, Erdheim-Chester disease, Eronen-Somer-Gustafsson syndrome, Erythema, Erythermalgia, Erythroblastopenia, Erythrocytosis, Erythroderma, Erythrokeratoderma, Erythromelalgia, Escher hirt syndrome, Escobar syndrome, Esophageal adenocarcinoma, Esophageal atresia, Essential cryoglobulinaemia, Essential iris atrophy, Essential osteolysis, Esthesioneuroblastoma, Estrogen receptor deficiency, Estrogen resistance syndrome, Evans syndrome, Ewing sarcoma, Exner syndrome, Exostoses, Exsudative retinopathy, Extracutaneous mastocytoma, Extrinsic allergic alveolitis, Eye disease, F syndrome, FAP, FAS deficiency, FCS syndrome, FCU, FENIB, FEOM, FFDD type I, FG syndrome, FLOTCH syndrome, FOP, FOSMN syndrome, FPS/AML syndrome, FRAXA syndrome, FRAXE syndrome, FRAXF syndrome, FSH resistance, Fabry disease, Factor VII deficiency, Factor VIII deficiency, Factor X deficiency, Factor XI deficiency, Factor XII deficiency, Factor XIII deficiency, Factors II, VII, IX and X, combined deficiency, Fahr syndrome, Fallot complex, Familial LCAT deficiency, Fanconi anaemia, Fanconi ichthyosis dysmorphism, Fanconi syndrome, Fanconi-Bickel disease, Fara-Chlupackova syndrome, Farber lipogranulomatosis, Farmer's lung disease, Fatal infantile COX deficiency, Faulk-Epstein-Jones syndrome, Favism, Fazio-Londe disease, Fechtner syndrome, Feigenbaum-Bergeron-Richardson syndrome, Feingold syndrome, Felty syndrome, Fenton wilkinson toselano syndrome, Ferlini-Ragno-Calzolari syndrome, Fernhoff-Blackston-Oakley syndrome, Fetal cytomegalovirus syndrome, Fetal edema, Fetal left ventricular aneurysm, Fibrinogen disorder, Fibrochondrogenesis, Fibrodysplasia ossificans progressiva, Fibromatosis, Fibromuscular dysplasia of arteries, Fibromyalgia, Fibronectin glomerulopathy, Fibrosarcoma, Fibrosing mediastinitis, Fibrosis of extraocular muscles, Fiessinger-Leroy-Reiter's syndrome, Figuera syndrome, Filamin anomaly, Filariasis, Filippi syndrome, Fine-Lubinsky syndrome, Finlay-Markes syndrome, Finucane kurtz scott syndrome, Fitz Hugh Curtis syndrome, Fitzsimmons-Guilbert syndrome, Fitzsimmons-McLachlan-Gilbert syndrome, Fitzsimmons-Walson-Mellor syndrome, Fixed subaortic stenosis, Flegel disease, Floating-Harbor syndrome, Florid cemento-osseous dysplasia, Flynn aird syndrome, Foix chavany marie syndrome, Foix-Alajouanine syndrome, Follicular atrophoderma-basal cell carcinoma, Follicular dendritic cell sarcoma, Follicular dyskeratoma, Follicular ichthyosis, Follicular lymphoma, Fontaine-Farriaux-Blanckaert syndrome, Forbes disease, Forney-Robinson-Pascoe syndrome, Forunculoid myiasis, Fountain syndrome, Fowler-Christmas-Chapple syndrome, Fox Fordyce disease, Fra-X syndrome, Fragile X syndrome, Fragoso cid garcia hernandez syndrome, Franceschetti-Klein syndrome, Francois dyscephalic syndrome, Francois syndrome, Franek bocker kahlen syndrome, Frank-Ter Haar syndrome, Franklin disease, Fraser like syndrome, Fraser syndrome, Frasier syndrome, Freeman-Sheldon syndrome, Freiberg's disease, Freire maia pinheiro opitz syndrome, Frey's syndrome, Frias syndrome, Fried syndrome, Fried-Goldberg-Mundel syndrome, Friedman goodman syndrome, Friedreich ataxia, Froelich's syndrome, Froster-Huch syndrome, Froster-Iskenius-Waterson syndrome, Fructosuria, Frydman-Cohen-Karmon syndrome, Fryns macrocephaly, Fryns-Aftimos syndrome, Fryns-Hofkens-Fabry syndrome, Fuhrmann-Rieger-de Sousa syndrome, Fukuda miyanomae nakata syndrome, Fukuhara syndrome, Fuqua-Berkovitz syndrome, Furlong syndrome, Furukawa takagi nakao syndrome, G syndrome, G6PD deficiency, GABA metabolism disease, GAMT deficiency, GAPO syndrome, GIST, GM1 gangliosidosis, GOSHS, GRACILE syndrome, GRF Tumour, GSD, GTN, GVH, Gaisbock syndrome, Galactokinase deficiency, Galactosemia, Galactosialidosis, Galloway syndrome, Galloway-Mowat syndrome, Gamborg nielsen syndrome, Game-Friedman-Paradice syndrome, Gamstorp episodic adynamy, Ganglioglioma, Garcia torres guarner syndrome, Garcia-Lurie syndrome, Gardner silengo wachtel syndrome, Gardner-Morrison-Abbott syndrome, Garret tripp syndrome, Gastric cancer, Gastroschisis, Gaucher disease, Gaucher-like disease, Geen sandford davison syndrome, Gelineau disease, Gemignani syndrome, Gemss syndrome, Genes syndrome, Genochondromatosis, Gerbode defect, Gerhardt syndrome, German syndrome, Gershonibaruch-Leibo syndrome, Gerstmann-Straussler-Scheinker syndrome, Ghosal syndrome, Gianotti Crosti syndrome, Giant cell arteritis, Giant platelet syndrome, Gilbert syndrome, Gilles de la Tourette syndrome, Gillespie syndrome, Gitelman syndrome, Glanzmann thrombasthenia, Glass bone disease, Glass-Chapman-Hockley syndrome, Glaucoma, Glioblastoma, Glomerular disease, Glomerulonephritis, Glomerulopathy with fibronectin deposits (GFND), Gloomy syndrome, Glucagonoma, Glucocorticoid resistance, Glycogen storage disease, Gms syndrome, Goiter-deafness syndrome, Golabi-Rosen syndrome, Goldberg syndrome, Goldberg-Maxwell syndrome, Goldberg-Shprintzen megacolon syndrome, Goldblatt viljoen syndrome, Goldblatt wallis syndrome, Goldenhar syndrome, Goldmann-Favre syndrome, Goldstein hutt syndrome, Goldston syndrome, Gollop syndrome, Gollop wolfgang complex, Goltz syndrome, Goltz-Gorlin syndrome, Gombo syndrome, Gonzales del angel syndrome, Goodman syndrome, Goodpasture syndrome, Goossens-Devriendt syndrome, Gordon syndrome, Gorham syndrome, Gorham-Stout disease, Gorlin syndrome, Gorlin-Chaudhry-Moss syndrome, Graft rejection after lung transplantation, Graft versus host disease, Graham boyle troxell syndrome, Graham-Cox syndrome, Grand-Kaine-Fulling syndrome, Grange occlusive arterial syndrome, Grant syndrome, Granulocytic sarcoma, Granulomatous allergic angiitis, Granulomatous inflammatory arthritis, dermatitis, and uveitis, Granulomatous mastitis, Graves' disease, Gray platelet syndrome, Greenberg dysplasia, Greig syndrome, Greither's disease, Griscelli disease, Grix blankenship peterson syndrome, Groll hirschowitz syndrome, Gronblad-Strandberg-Touraine syndrome, Grosse syndrome, Grover's disease, Growth hormone deficiency, Grubben de cock borghgraef syndrome, Gräsbeck-Imerslund disease, Guam disease, Guanidinoacetate methyltransferase deficiency, Guibaud-Vainsel syndrome, Guillain-Barr syndrome, Guizar-Vasquez-Luengas syndrome, GuizarVazquez-Sanchez-Manzano syndrome, Gunal seber basaran syndrome, Gurrieri-Sammito-Bellussi syndrome, Gusher syndrome, Gynandroblastoma, Günther disease, HAD deficiency, HAE, HAIRAN syndrome, HANAC syndrome, HARD syndrome (Hydrocephalus-agyria-retinal dysplasia), HCDD, HCL, HDL metabolism disorder, HEM, HEP, HERNS syndrome, HHE syndrome, HHT, HHV-8, HID syndrome, HIGM1, HIT, HMSN 5, HMSNP, HNPCC, HNSCC, HPA-1 deficiency, HPE, HSAN 1, HSD deficiency, HSV encephalitis, HSV keratitis, HUS, HVR, Haas-Robinson syndrome, Haddad syndrome, Haematologic cancers, Haemochromatosis, Haemoglobin disorders, Haemolysis, Haemolytic anaemia, Haemolytic uremic syndrome, Haemorrhagic fever, Haemorrhagiparous thrombocytic dystrophy, Hageman factor deficiency, Hagemoser weinstein bresnick syndrome, Hailey-Hailey disease, Haim-Munk syndrome, Hairy cell leukaemia, Hajdu-Cheney syndrome, Hal-Berg- Rudolph syndrome, Halal syndrome, Halal-Setton-Wang syndrome, Hallermam streiff like syndrome, Hallermann-Streiff-Francois syndrome, Hallervorden-Spatz disease, Hamanishi ueba tsuji syndrome, Hamano tsukamoto syndrome, Hamman-Rich syndrome, Hanhart syndrome, Hand Foot Mouth syndrome, Hand-Shuller-Christian disease, Hanot syndrome, Hantavirus pulmonary syndrome, Hapnes boman skeie syndrome, Happy puppet syndrome, Harboyan syndrome, Hardcastle syndrome, Harding ataxia, Harrod syndrome, Harrod-Keele syndrome, Hartnup disorder, Hartsfield bixler demyer syndrome, Hashimoto struma, Hashimoto-Pritzker syndrome, Haspeslagh-Fryns-Muelenaere syndrome, Hawkinsinuria, Hay wells syndrome, Heart block progressive, Heart-hand syndrome, Heavy chain deposition disease, Hec syndrome, Hecht scott syndrome, Heckenlively syndrome, Heide syndrome, Heimler syndrome, Heiner syndrome (cow's milk hypersensitivity), Helmerhorst heaton crossen syndrome, Hemangioma-thrombocytopenia syndrome, Hemangiopericytoma, Hematopoietic hypoplasia, Hemeralopia, Hemi 3 syndrome, Hemiconvulsion-Hemiplegia-Epilepsy syndrome, Hemifacial hyperplasia strabismus, Hemihypertrophy intestinal web corneal opacity, Hemimelia, Hemitruncus, Hemochromatosis, Hemoglobin C disease, Hemoglobin E disease, Hemoglobin H disease, Hemolytic anaemia, Hemophilia, Hemorrhagiparous thrombocytic dystrophy, Hennekam koss de geest syndrome, Hennekam syndrome, Hennekam-Beemer syndrome, Henoch-Schoenlein purpura, Hepatic cystic hamartoma, Hepatic fibrosis, Hepatic cancer, Hepatic venoocclusive disease, Hepatitis B re-infection following liver transplantation, Hepatitis, Hepatoblastoma, Hepatocellular adenoma, Hepatocellular carcinoma, Hepatoerythropoeitic porphyria, Hepatoportal sclerosis, Hereditary coproporphyria, Hereditary endotheliopathy-retinopathy-nephropathy-stroke, Hereditary lymphoedema type I, Hereditary motor and sensory neuropathy, Hereditary vascular retinopathie-Raynaud phenomenon-migraine, Hermansky-Pudlak syndrome, Hernandez fragoso syndrome, Hernandez-Aguirre Negrete syndrome, Herpes virus infection, Herrmann opitz arthrogryposis syndrome, Hers disease, Hersh-Podruch-Weisskopf syndrome, Herva disease, Heterotaxia, Heterozygous OSMED, Hillig syndrome, Hinman syndrome, Hinson-Pepys disease, Hipo syndrome, Hirayama disease, Hirschsprung disease, Hirsutism, His bundle tachycardia, Histidine metabolism disorder, Histidinuria renal tubular defect, Histiocytic and dendritic cell tumour, Histiocytic sarcoma, Histiocytoid cardiomyopathy, Histiocytosis X, Histoplasmosis, Hittner hirsch kreh syndrome, Hmc syndrome, Hodgkin lymphoma, Hoepffner dreyer reimers syndrome, Hoffman's syndrome, Holmes benacerraf syndrome, Holmes collins syndrome, Holmes-Gang syndrome, Holoacardius amorphus, Holoprosencephaly, Holt-Oram syndrome, Holzgreve wagner rehder syndrome, Homocarnosinosis, Homocystinuria, Homogentisic acid oxydase deficiency, Hoon hall syndrome, Horner syndrome, Horton disease, Houlston ironton temple syndrome, House allergic alveolitis, Howard young syndrome, Howell-Evans syndrome, Hoyeraal-Hreidarsson syndrome, Humeroradial synostosis, Humeroradioulnar synostosis, Humerospinal dysostosis, Hunter carpenter mc donald syndrome, Hunter jurenka thompson syndrome, Hunter syndrome, Hunter-Rudd-Hoffmann syndrome, Hunter-Thompson-Reed syndrome, Huntington disease, Huriez syndrome, Hurler syndrome, Hurler-Scheie syndrome, Hutchinson-Gilford syndrome, Hutteroth spranger syndrome, Hyaline membrane disease, Hyaluronidase deficiency, Hydatidosis, Hyde-Forster-Mccarthy-Berry syndrome, Hygroma cysticum, Hyperaldosteronism, Hyperargininemia, Hyperbilirubinemia, Hypercalciuria idiopathic, Hypercholesterolemia, Hyperchylomicronemia, Hypercortisolism, Hyperexplexia, Hyperglycinemia, Hyperimidodipeptiduria, Hyperinsulinism, Hyperkeratosis, Hyperlipidaemia, Hyperlipoproteinemia, Hyperlysinemia, Hypermethioninemia, Hyperornithinemia, Hyperostosis, Hyperoxaluria, Hyperparathyroidism, Hyperphalangism dysmorphy bronchomalacia, Hyperphenylalaninemic embryopathy, Hyperpipecolatemia, Hypersensitivity pneumonitis, Hypertelorism, Hyperthermia, Hyperthyroidism, Hypertrichosis, Hypertrophic neuropathy, Hypertrophic or verrucous lupus erythematosus, Hypertrophic subaortic stenosis, Hypobetalipoproteinemia, Hypobetalipoproteinemia, Hypochondroplasia, Hypocomplementaemic leucocytoclasic vasculitis, Hypodontia, Hypofibrinogenemia, Hypokalemic alkalosis, Hypokeratosis, Hypomyelination, Hypoparathyroidism, Hypopituitarism, Hypoplastic left heart syndrome, Hypoplastic right heart syndrome, Hypospadias, Hypothalamic hamartoblastoma syndrome, Hypothyroidism, Hypotrichosis, Hypoxanthine guanine phosphoribosyltransferase (HPRT) complete deficiency, I-cell disease, IBIDS syndrome, ICCA syndrome, ICE syndrome, ICF syndrome, ICOS deficiency, IDI, IED, IFAP syndrome, IGDA, IGF-1 deficiency, IGHD, IMAGe syndrome, INAD, INCL, IOMID syndrome, IOSCA, IPEX, IPSID, IRAK4 deficiency, ISOD, ITP, IVC stenosis, Ichthyiosis, Idaho syndrome, Idiopathic dystonia DYT1, Idiopathic granulomatous mastitis, Idiopathic hypereosinophilic syndrome, Idiopathic infantile arterial calcification, Idiopathic infection caused by BCG or atypical mycobacteria, Idiopathic interstitial pneumonia, Idiopathic juvenile osteoporosis, Idiopathic myelofibrosis, Idiopathic obliterative arteriopathy, Idiopathic orthostatic hypotension, Idiopathic pulmonary fibrosis, Idiopathic thrombocytopenic purpura, Ieshima-Koeda-Inagaki syndrome, Illum syndrome, Ilyina amoashy grygory syndrome, Imaizumi kuroki syndrome, Immune thrombocytopaenia, Immunodeficiency, Immunoproliferative small intestinal disease, Infant respiratory distress syndrome, Insulin-resistance syndrome, Insulinoma, Interdigitating dendritic cell sarcoma, Intermediate DEND syndrome, Intermediate spinal muscular atrophy, Internal carotid agenesis, Interstitial cystitis, Interstitial granulomatous dermatitis with arthritis, Interstitial pneumonia, Interventricular septum aneurysm, Intestinal atresia multiple, Intestinal epithelial dysplasia, Intestinal hypomagnesemia with secondary hypocalcemia, Intestinal lipodystrophy, Intestinal lipophagic granulomatosis, Intestinal lymphangiectasia, Intestinal pseudoobstruction, Intracerebral haemorrhage, Intracranial aneurysms, Intracranial arterioveinous malformation, Inverse Marcus-Gunn phenomenon, Iridocorneal endothelial syndrome, Iridogoniodysgenesis, Irons-Bhan syndrome, Irritable bowel syndrome, Isaac's syndrome, Isaacs mertens syndrome, Ischaemic brain injury, Ischemia/perfusion injury associated with solid organ transplantation procedure, Ischio-vertebral dysplasia, Iso-Kikuchi syndrome, Isosporiasis, Isotretinoin syndrome, Isotretinoin-like syndrome, Isovaleric acidemia, Itin syndrome, Ito hypomelanosis, Ivemark syndrome, JAE, JWS, Jackson-Barr syndrome, Jackson-Weiss syndrome, Jacobs syndrome, Jacobsen syndrome, Jaffe campanacci syndrome, Jaffe-Lichtenstein disease, Jagell holmgren hofer syndrome, Jalili syndrome, Jancar syndrome, Japanese encephalitis, Jarcho-Levin syndrome, Jaw-Winking syndrome, Jensen syndrome, Jequier-Kozlowski syndrome, Jervell and Lange-Nielsen syndrome, Jeune syndrome, Job syndrome, Johanson-Blizzard syndrome, Johnson syndrome, Johnson-McMillin syndrome, Johnson-Munson syndrome, Johnston-Aarons-Schelley syndrome, Jones syndrome, Jorgenson lenz syndrome, Joubert syndrome, Joubert-Boltshauser syndrome, Juberg hayward syndrome, Juberg-Marsidi syndrome, Judge misch wright syndrome, Jumping Frenchman of Maine, Jung wolff back stahl syndrome, Juvenile chronic myelomonocytic leukaemia, Juvenile gastrointestinal polyposis, Juvenile glaucoma, Juvenile hemochromatosis, Juvenile hyaline fibromatosis, Juvenile idiopathic arthritis, Juvenile macular degeneration, Juvenile myelomonocytic leukaemia, Juvenile polyposis syndrome (JPS), Juvenile temporal arteritis, KBG syndrome, KBG-like syndrome, KID syndrome, Kabuki syndrome, Kaeser syndrome, Kahler's disease, Kaler garrity stern syndrome, Kallin syndrome, Kallmann syndrome, Kalyanaraman syndrome, Kanzaki disease, Kaplan-Plauchu-Fitch syndrome, Kaplowitz-Bodurtha syndrome, Kaposi's sarcoma, Kaposiform hemangioendothelioma, Kapur-Toriello syndrome, Karandikar-Maria-Kamble syndrome, Karsch neugebauer syndrome, Kartagener syndrome, Kasabach-Merritt syndrome, Kashani-Strom-Utley syndrome, Kasznica carlson coppedge syndrome, Katsantoni papadakou lagoyanni syndrome, Kaufman-Mckusick syndrome, Kawasaki disease, Kawashima syndrome, Kawashima-Tsuji syndrome, Kearns-Sayre syndrome, Kelley-Seegmiller syndrome, Kelly-Kirson-Wyatt syndrome, Kennedy disease, Kennedy-Teebi syndrome, Kennerknecht syndrome, Kenny syndrome, Kenny-Caffey syndrome, Kenya tick-bite fever, Keratinisation disorder associated with genetic eye disease, Keratitis, Keratoacanthoma, Keratoconus, Keratoderma, Keratosis, Kerion celsi, Kersey syndrome, Ketoacidosis, Ketoaciduria, Ketolysis disorder, Keutel syndrome, KGB syndrome, Khalifa-Graham syndrome, Kienbock disease, Kikuchi disease, Kikuchi-Fujimoto disease, Kimura disease, King-Denborough syndrome, Kinsbourne syndrome, Klatskin tumour, Klein-Waardenburg syndrome, Kleine-Levin syndrome, Kleiner holmes syndrome, Klinefelter syndrome, Klippel-Feil malformation, Klippel-Trenaunay syndrome, Kluver-Bucy syndrome, Kniest dysplasia, Knobloch layer syndrome, Kocher-Debre-Semelaigne syndrome, Kohler's disease, Kohlschutter-Tonz syndrome, Kok disease, Komar syndrome, Konigsmark knox hussels syndrome, Kopysc barczyk krol syndrome, Kosenow syndrome, Kostmann syndrome, Kosztolanyi syndrome, Koussef nichols syndrome, Kousseff syndrome, Kowarski syndrome, Kozlowski brown hardwick syndrome, Kozlowski massen syndrome, Kozlowski ouvrier syndrome, Kozlowski tsuruta syndrome, Kozlowski-Krajewska syndrome, Krabbe disease, Krasnow-Qazi syndrome, Krauss herman holmes syndrome, Kudo tamura fuse syndrome, Kugelberg-Welander disease, Kumar-Levick syndrome, Kunze riehm syndrome, Kurczynski-Casperson syndrome, Kuskokwim disease, Kuzniecky syndrome, Kynureninase deficiency, Kyphomelic dysplasia, Kyphosis brachyphalangy optic atrophy, Küssmaul-Maier disease, L1 syndrome, L-2-hydroxyglutaricaciduria, LADD syndrome, LBSL, LBWC syndrome, LCAD, LCAT deficiency, LCCS, LCDD, LCH, LCHAD deficiency, LDD, LEOPARD syndrome, LGMD, LHCDD, LIG4 syndrome, LMS, LORD, LPI, Laband syndrome, Lachiewicz sibley syndrome, Lactate dehydrogenase deficiency, Lactic acidosis, Lactotroph adenoma, Ladda zonana ramer syndrome, Lafora disease, Laing distal myopathy, Lambdoid synostosis, Lambert syndrome, Lambert-Eaton myasthenic syndrome, Lamellar ichthyosis, Laminopathy, Landau-Kleffner syndrome (LKS), Landing disease, Landouzy-Dejerine myopathy, Langer-Giedion syndrome, Langerhans cell granulomatosis, Langerhans cell histiocytosis, Langerhans cell sarcoma, Laparoschisis, Laplane fontaine lagardere syndrome, Laron syndrome, Larsen syndrome, Larsen-like syndrome, Laryngeal abductor paralysis, Laryngo onycho cutaneous syndrome, Laryngo-tracheo-esophageal cleft pulmonary hypoplasia, Lassa fever, Lassueur-Graham-Little syndrome, Late infantile neuronal ceroid lipofuscinosis, Late onset sepsis in premature infants, Lathosterolosis, Laubrypezzi syndrome, Launois-Bensaude adenolipomatosis, Laurence-Moon syndrome, Laurin-Sandrow syndrome, Lawrence syndrome, Lawrence-Seip syndrome, Laxova-Opitz syndrome, Le Merrer syndrome, Le marec bracq picaud syndrome, Leao-da Silva syndrome, Learman syndrome, Leber 'plus' disease, Leber congenital amaurosis, Leber miliary aneurysm, Left renal vein entrapment syndrome, Left ventricular hypertrabeculation, Left ventricular noncompaction, Legg-Calve-Perthes disease, Legionellosis, Legionnaires' disease, Leichtman-Wood-Rohn syndrome, Leifer lai buyse syndrome, Leigh disease, Leiner disease, Leiomyomatosis of esophagus cataract hematuria, Leiomyomatosis, Leiomyosarcoma, Leipala kaitila syndrome, Leishmaniasis, Leisti-Hollister-Rimoin syndrome, Lemierre syndrome, Lenegre disease, Lennox-Gastaut syndrome, Leprechaunism, Leprosy, Leptospirosis, Leri pleonosteosis, Leri-Weill syndrome, Lesch-Nyhan syndrome, Lethal arthrogryposis with anterior horn cell disease (LAAHD), Lethal chondrodysplasia moerman type, Lethal congenital contracture syndrome, Lethal osteosclerotic bone dysplasia, Letterer-Siwe disease, Leucinosis, Leukaemia, Leukocyte adhesion deficiency (LAD), Leukodystrophy, Leukoencephalopathy, Leukonychia totalis, Leukotriene C4 (LTC4) synthase deficiency, Levic stefanovic nikolic syndrome, Levine-Critchley syndrome, Levocardia, Levy-Hollister syndrome, Levy-Yeboa syndrome, Lewis-Pashayan syndrome, Lewis-Sumner syndrome, Lewy body dementia, Leydig cell hypoplasia, Lhermitte-Duclos disease, Li-Fraumeni syndrome, Lichen, Lichstenstein syndrome, Liddle syndrome, Lindsay-Burn syndrome, Linear hamartoma syndrome, Linitis plastica, Lip-pit syndrome, Lipid storage disease, Lipodystrophy, Lipodystrophy-HIV related, Lipoedema, Lipoid proteinosis, Lipomatosis, Lipoprotein metabolism disease, Liposarcoma, Lisker-Garcia-Ramos syndrome, Lissencephaly, Listeriosis, Little syndrome, Lobar atrophy of brain, Lobstein disease, Lobster-claw deformity, Localized Castleman disease, Localized scleroderma, Locked-in syndrome, Loeffler's endocarditis, Loeys-Dietz syndrome, Loffredo cennamo cecio syndrome, Logic syndrome, Loiasis, Long QT syndrome, Longman-Tolmie syndrome, Loose anagen syndrome, Lopes gorlin syndrome, Lopes marques de faria syndrome, Lopez-Hernandez syndrome, Lou-Gehrig disease, Louis-Bar syndrome, Lowe kohn cohen syndrome, Lowe oculocerebrorenal syndrome, Lowe syndrome, Lower mesodermal defects, Lown-Ganong-Levine syndrome, Lowry syndrome, Lowry-MacLean syndrome, Lowry-Yong syndrome, Lubani-Al Saleh-Teebi syndrome, Lubinsky syndrome, Lubs-Arena Syndrome, Lucey driscoll syndrome, Lucky gelehrter syndrome, Lujan-Fryns syndrome, Lunatomalacia, Lundberg syndrome, Lung agenesis heart defect thumb anomalies, Lung cancer small cell, Lung fibrosis, Lupus erythematosus, Lurie kletsky syndrome, Luteinizing hormone releasing hormone deficiency with ataxia, Lutz-Richner-Landolt syndrome, Lyell syndrome, Lyme borreliosis, Lyme disease, Lymphangioleiomyomatosis, Lymphangioma, Lymphatic filariasis, Lymphatic malformation, Lymphedema, Lymphocyte apoptosis anomaly, Lymphocyte-depleted classical hodgkin lymphoma, Lymphocyte-rich classical hodgkin lymphoma, Lymphocytic colitis, Lymphoid interstitial pneumonia, Lymphomatoid granulomatosis, Lymphoproliferative disease associated with primary immune disease, Lynch lee murday syndrome, Lynch syndrome, Lyngstadaas syndrome, Lysosomal disease, Lytico-bodig disease, M-CMTC, M/SCHAD, MAD, MADSAM, MAE, MALT lymphoma, MASA syndrome, MCA, MCAD deficiency, MCOPS1, MDC1A, MEB (Muscle-Eye-Brain) syndrome, MEHMO syndrome, MELAS, MEN 1, MEN 2, MERRF syndrome, MGA type I, MHBD deficiency, MIDD, MIRAS, MMEP syndrome, MMND, MNGIE syndrome, MOBA syndrome, MOCOD, MODY syndrome, MORM syndrome, MPPH syndrome, MPS, MRGH, MRKH syndrome, MRXS7, MSA, MTHFR deficiency, MVA syndrome, MYH9, Mac Duffie's syndrome, Mac dermot winter syndrome, Maccario mena syndrome, Macdermot-Patton-Williams syndrome, Machado-Joseph disease, Macias flores garcia cruz rivera syndrome, Mackay shek carr syndrome, Macroglossia, Macrophage or histiocytic tumour, Macrophagic activation syndrome, Macrophagic myofasciitis, Macrothrombocytopenia with leukocyte inclusions, Macular amyloidosis, Macular dystrophy, Macular edema, Madelung's disease, Madras motor neuron disease, Maffucci syndrome, Majeed syndrome, Majewxki orturk syndrome, Major airway collapse, Meleda disease, Malakoplakia, Malakoplasia, Malaria, Malignant fibrous histiocytoma, Malignant germ cell tumor, Malignant hyperpyrexia, Malignant hyperthermia, Malignant mesenchymal tumor, Malignant paroxysmal ventricular tachycardia, Mallory Weiss syndrome, Malouf syndrome, Maltase-glucoamylase deficiency, Maniac-depressive disorders, Manouvrier syndrome, Mansonellosis, Mantle cell lymphoma, Maple syrup urine disease, Marashi gorlin syndrome, Marble brain disease, Marburg disease, Marchiafava-Micheli disease, Marcus-Gunn syndrome, Marden walker like syndrome, Marfan syndrome, Margarita island ectodermal dysplasia, Marin-Amat syndrome, Marinesco-Sjogren syndrome, Marion mayers syndrome, Markel-Vikkula-Mulliken syndrome, Marles greenberg persaud syndrome, Maroteaux cohen solal bonaventure syndrome, Maroteaux le merrer bensahel syndrome, Maroteaux stanescu cousin syndrome, Maroteaux-Lamy syndrome, Maroteaux-Malamut syndrome, Marsden nyhan sakati syndrome, Marshall syndrome, Marshall-Smith syndrome, Martinez monasterio pinheiro syndrome, Martinez-Frias syndrome, Martsolf syndrome, Massa casaer ceulemans syndrome, Mast cell leukaemia, Mast cell sarcoma, Mastocytosis, Mastroiacovo de rosa satta syndrome, Mathieu de broca bony syndrome, Matsoukas liarikos giannika syndrome, Matthew-Wood syndrome, Mature B-cell tumour, Mature T-cell and NK-cell tumour, May-Hegglin thrombocytopenia, Mayer-Rokitansky-Kuster-Hauser syndrome, Mazabraud syndrome, McArdle disease, McCabe's disease, McCune-Albright syndrome, McDonough syndrome, McDowall syndrome, McGrath syndrome, McKusick-Kaufman syndrome, McLeod syndrome, McPherson-Hall syndrome, Mcalister crane syndrome, Mccallum macadam johnston syndrome, Mcgillivray syndrome, Mclain-Dekaban syndrome, Mcpherson clemens syndrome, Meacham winn culler syndrome, Meadows' syndrome, Meckel like syndrome, Meckel syndrome, Meckel-Gruber syndrome, Meconium aspiration syndrome, Medeira dennis donnai syndrome, Mediastinal (thymic) large b-cell lymphoma, Mediastinal diffuse large-cell lymphoma with sclerosis, Mediastinal fibrosis, Medrano roldan syndrome, Medullar disease, Medullary cystic kidney disease, Medulloblastoma, Megacalycosis, Megaduodenum and/or megacystis, Megaloblastic anaemia, Megarbane-Loiselet syndrome, Mehes syndrome, Mehta-Lewis-Patton syndrome, Meier blumberg imahorn syndrome, Meier-Gorlin syndrome, Meige disease, Meinecke pepper syndrome, Meinecke syndrome, Melanoma, Meleda disease, Melhem fahl syndrome, Melioidosis, Melkersson rosenthal syndrome, Melnick-Needles syndrome, Melorheostosis, Membranoproliferative glomerulonephritis, Membranous glomerulopathy, Menetrier's disease, Mengel konigsmark syndrome, Meniere's disease, Meningioma, Meningitis, Menkes syndrome, Mental retardation, Meretoja syndrome, Merkel cell carcinoma (MCC), Merlob grunebaum reisner syndrome, Mesangial sclerosis, Mesodermic dysplasia, Mesothelioma, Mesulam syndrome, Metabolic intoxication disease, Metabolic liver disease, Metaphyseal dysplasia, Michels syndrome, Mickleson syndrome, Micro syndrome, Microcephaly, Microcoria, Microcystic infiltrating lymphatic malformation, Microcytic anaemia, Microphthalmia, Microscopic colitis Microtia, Microvillous inclusion disease, Mid-aortic dysplastic syndrome, Midas syndrome, Middle aortic syndrome, Midline heart, Mietens syndrome, Mievis verellen dumoulin syndrome, Mikati najjar sahli syndrome, Mikulicz disease, Mild campomelic dysplasia, Miller syndrome, Miller-Dieker syndrome, Miller-Fisher syndrome (MFS), Mills syndrome, Milroy disease, Minimal change nephrotic syndrome (MCNS), Minkowski-Chauffard disease, Mirhosseini-Holmes-Walton syndrome, Mitral valve prolapse disease, Miura syndrome, Mixed connective tissue disease, Mixed phenotype acute leukaemia, Mixed sclerosing bone dystrophy, Miyoshi myopathy, Mls syndrome, Moderate and severe traumatic brain injury, Moebius syndrome, Moerman vandenberghe fryns syndrome, Moersch-Woltman syndrome, Moeschler clarren syndrome, Mohr syndrome, Mohr-Tranebjaerg syndrome, Mollica pavone antener syndrome, Moloney syndrome, Momo syndrome, Monilethrix, Mononen-Karnes-Senac syndrome, Monostotic fibrous dysplasia, Montefiore syndrome, Moore-Federman syndrome, Morava-Mehes syndrome, Morgagni-Stewart-Morel syndrome, Morillo cucci passarge syndrome, Morning glory syndrome, Morquio disease, Morris syndrome, Morse rawnsley sargent syndrome, Morvan syndrome, Moschcowitz disease, Mounier-Kuhn syndrome, Mousa-Al Din-Al Nassar syndrome, Movement disease, Mowat-Wilson syndrome, Moya-moya disease, Moynahan syndrome, Mpo deficiency, Msbd syndrome, Mseleni joint disease (MJD), Mucha Habermann Disease, Muckle-Wells syndrome, Mucoepithelial dysplasia, Mucolipidosis, Mucopolysaccharidosis, Mucormycosis, Mucosal pemphigoid, Mucosulfatidosis, Muenke syndrome, Muir-Torre syndrome, Mullerian aplasia, Multicentric Castleman disease (MCD), Multicentric giant lymph node hyperplasia, Multicentric osteolysis, Multifocal acquired demyelinating sensory and motor neuropathy, Multifocal pattern dystrophy simulating fundus flavimaculatus, Multiglandular hyperplasia, Multiminicore disease (MmD), Multinodular goiter cystic kidney polydactyl), Multiple carboxylase deficiency, Multiple contracture syndrome, Multiple cutaneous and uterine leiomyomas, Multiple endocrine neoplasia, Multiple epiphyseal dysplasia, Multiple fibrofolliculoma, Multiple hamartoma syndrome, Multiple keratoacanthoma, Multiple pterygium syndrome, Multiple sclerosis, Multiple sulfatase deficiency, Multiple system atrophy, Multiple ventricular septal defects, Mulvihill-Smith syndrome, MURCS association, Murray-Puretic-Drescher syndrome, Muscular channelopathy, Muscular dystrophy, Muscular fibrosis multifocal obstructed vessels, Mutchinick syndrome, Myalgia eosinophilia associated with tryptophan, Myasthenia gravis, Myasthenic syndromes, Mycetoma, *Mycoplasma* encephalitis, Mycosis fungoides, Myelinoclastic diffuse sclerosis, Myelinosis centralis diffusa, Myelocerebellar disorder, Myelodysplastic or myeloproliferative disease, Myelofibrosis with myeloid metaplasia, Myeloid sarcoma, Myeloma, Myhre syndrome, Myiasis, Myoclonic dystonia, Myoclonic epilepsy, Myodysplasia, Myofibrillar myopathy, Myoglobinuria, Myopathy and diabetes mellitus, Myopathy, Myopia, Myositis ossificans progressiva, Myotilinopathy, Myotonia congenita, Myotonic disease, Myotubular myopathy, Myxofibrosarcoma, Myxoid liposarcoma, Myxoid malignant fibrous histiocytoma, Myxoma with fibrous dysplasia, Möbius syndrome, N syndrome, NACG, NAGS deficiency, NAME syndrome, NAO syndrome, NARP syndrome, NASH syndrome, NBS, NCL, NCMD, NF 1, NFJ syndrome, NHL, NHPP, NISCH syndrome, NOMID syndrome, NPLCA, NSIP, NTD, Naegeli syndrome, Naegeli-Franceschetti-Jadassohn syndrome, Nager syndrome, Naguib syndrome, Nail anomaly, Nail dysplasia, Naito-Oyanagi disease, Nakagawa's angioblastoma, Nakajo nishimura syndrome, Nakajo syndrome, Nakamura osame syndrome, Nance-Horan syndrome, Narcolepsy without cataplexy, Narcolepsy-Cataplexy, Nasodigitoacoustic syndrome, Nasopharyngeal cancer, Nasu-Hakola disease, Nathalie syndrome, Navajo brainstem syndrome, Naxos disease, Necrotising hypophysitis, Necrotizing myelitis, Nemaline myopathy, Neonatal Onset Multisystem Inflammatory Disease, Neonatal death immune deficiency, Neonatal hemochromatosis, Neonatal neutropenia, Neonatal respiratory distress syndrome, Nephroblastoma, Nephrogenic fibrosing dermopathy, Nephrogenic systemic fibrosis, Nephrolithiasis, Nephronophthisis-hepatic fibrosis, Nephropathy, Nephrosis, Nephrotic syndrome with diffuse mesangial sclerosis, Nephrotic syndrome, Nervous system tumour, Netherton disease, Neu-Laxova syndrome, Neuhauser daly magnelli syndrome, Neuhauser eichner opitz syndrome, Neuhauser's anomaly, Neural crest tumour, Neuroacanthocytosis, Neuroaxonal dystrophy, Neuroblastoma, Neurocutaneous melanosis, Neurodegeneration due to 3-hydroxyisobutyryl-CoA hydrolase deficiency, Neurodegeneration with brain iron accumulation (NBIA), Neurodegenerative disease, Neuroectodermal syndrome, Neuroepithelioma, Neurofibromatosis, Neurolipomatosis, Neuromuscular junction disease, Neuromyelitis optica, Neuromyotonia, Neuropathy, Neutral Lipid Storage Disease, Neutropaenia, Nevo syndrome, Nevoid hypermelanosis, Nezelof syndrome, Nicolaides baraitser syndrome, Niemann-Pick disease, Nievergelt syndrome, Niikawa-Kuroki syndrome, Nijmegen breakage syndrome, Nivelon-Nivelon-Mabille syndrome, Noack syndrome, Noble bass sherman syndrome, Nocardiosis, Nodular lymphocyte predominant Hodgkin lymphoma, Nodulosis-arthropathy-osteolysis syndrome, Noma, Non-24-Hour Sleep-Wake syndrome, Non-DYT1 idiopathic torsion dystonia, Non-Hodgkin malignant lymphoma, Non-alcoholic steatohepatitis, Non-amyloid monoclonal immunoglobulin deposition disease, Non-giant cell granulomatous temporal arteritis with eosinophilia, Non-infectious uveitis affecting the posterior segment of the eye, Nonaka myopathy, Nondysgerminomatous germ cell tumor, Noonan like contracture myopathy hyperpyrexia, Noonan like syndrome, Noonan syndrome, Normomorphic sialidosis, Norrie disease, Norum disease, Nova syndrome, Novak syndrome, Nuclear cell envelopathy, O donnell pappas syndrome, O'Doherty syndrome, O'Sullivan-McLeod syndrome, OA-1, OCA, OCRL1, OFC syndrome, OFCD syndrome, OHSS, OLEDAID, ONMR syndrome, OPPG, ORW 2, OSLAM syndrome, OSMED, OTUDP syndrome, Obliterative portal venopathy, Occlusive infantile arteriopathy, Occupational allergic alveolitis, Ochoa syndrome, Ochronosis, Oculo skeletal renal syndrome, Oculo-osteo-cutaneous syndrome, Oculoectodermal syndrome, Oculogastrointestinal muscular dystrophy, Oculomotor palsy, Oculomotor paralysis, Oculopharyngodistal myopathy, Odontologic disease, Odontomatosis, Oerter-Friedman-Anderson syndrome, Oesophageal atresia, Oguchi disease, Ohaha syndrome, Ohdo madokoro sonoda syndrome, Ohtahara syndrome, Okamoto syndrome, Okihiro syndrome, Oligocone syndrome, Oligomeganephronia, Oliver mcfarlane syndrome, Oliver syndrome, Ollier disease, Olmsted syndrome, Omenn syndrome, Omodysplasia, Onat syndrome, Onchocerciasis, Ondine syndrome, Ondine-Hirschsprung disease, Onychodystrophy, Oochs syndrome, Ophtalmic ichthyosis, Ophtalmoplegia, Opitz BBB/G syndrome, Opitz reynolds fitzgerald syndrome, Opitz-Caltabiano syndrome, Opitz-Frias syndrome, Oppenheim's dystonia, Opsismodysplasia, Opsoclonus-myoclonus syndrome, Optic atrophy, Optic nerve hypoplasia, Optic neuropathy, Optic pathway glioma, Orbital leiomyoma, Ormond's disease, Ornithine aminotransferase deficiency, Orofaciodigital syndrome, Oromandibular dystonia, Oroticaciduria, Oroya fever, Osebold-Remondini syndrome, Osgood-Schlatter disease, Osler-Vaquez disease, Osteoarthropathy, Osteoblastoma, Osteochondritis, Osteochondromas, Osteochondrosis, Osteocraniostenosis, Osteodysplasia, Osteoectasia, Osteogenic sarcoma, Osteolysis, Osteomesopyknosis, Osteonecrosis, Osteopaenia, Osteopathia striata-cranial sclerosis, Osteopetrosis, Osteopoikilosis, Osteoporosis, Osteosarcoma, Osteosclerosis, Ostravik lindemann solberg syndrome, Otosclerosis, Ouvrier billson syndrome, Ovarian Sertoli-Leydig cell tumor, Ovarian cancer, Ovarian germ cell malignant tumor, Ovarioleukodystrophy, Oxalosis, PAF, PAGOD syndrome, PAN, PANDAS, PAP, PAPA syndrome, PARC syndrome, PCA, PCARP, PCH with optic atrophy, PCT, PDALS, PEHO syndrome, PEL, PELVIS syndrome, PFAPA syndrome, PFIC, PHACE syndrome, PIBIDS syndrome, PJS, PLOSL, PMD, PNDM, POADS, POEMS syndrome, POF, POMC deficiency, PPA, PPHS, PPM-X, PPoma, PSEK, PSP, PTC-RCC, PTLAH, PTLD, Pachygyria, Pachyonychia, Pacman dysplasia, Paediatric Autoimmune Disorders Associated with *Streptococcus* infections, Paediatric Autoimmune Neuropsychiatric Disorders Associated with *Streptococcus* infections, Paediatric granulomatous arthritis, Paget disease, Pagon stephan syndrome, Pai syndrome, Pallister W syndrome, Pallister-Hall syndrome, Pallister-Killian syndrome, Palmer pagon syndrome, Palpebral disease, Panayiotopoulos syndrome, Pancreatic carcinoma, Pancreatitis, Panner disease, Panniculitis, Panostotic fibrous dysplasia, Papillo-renal syndrome, Papillomatosis, recurrent respiratory, Papillon-Leage-Psaume syndrome, Papillon-Lefevre syndrome, Papular and sclerodermoid lichen myxedematosus, Papular atrichia, Papular mucinosis of infancy, Paramyotonia, Paraneoplastic pemphigus, Paraneoplastic retinopathy, Paraplegia, Parathyroid carcinoma, Parenchymatous liver disease, Paris-Trousseau thrombocytopenia, Parkes-Weber syndrome, Parkinson disease, Parkinsonism-dementia-ALS complex, Paroxysmal cold haemoglobinuria, Paroxysmal exertion-induced dyskinesia, Paroxysmal ventricular fibrillation, Parry-Romberg syndrome, Parsonage-Turner syndrome, Partial deep dermal and full thickness burns, Partington amyloidosis, Partington disease, Partington-Anderson syndrome, Partington-Mulley syndrome, Parvovirus antenatal infection, Pascuel castroviejo syndrome, Pashayan syndrome, Passwell-Goodman-Siprkowski syndrome, Patau syndrome, Patterned dystrophy of the retinal pigment epithelium, Patterson pseudoleprechaunism syndrome, Patterson stevenson syndrome, Patterson-Lowry rhizomelic dysplasia, Pauciarticular chronic arthritis, Pavone fiumara rizzo syndrome, Pearson syndrome, Peeling skin syndrome, Pelget-Huer anomaly, Pelizaeus-Merzbacher brain sclerosis, Pellagra, Pemphigus, Pena-Shokeir syndrome, Pendred syndrome, Penta X syndrome, Pentosuria, Peptide metabolism disease, Peptidic growth factors deficiency, Perheentupa syndrome, Periarteritis nodosa, Pericardial defect diaphragmatic hernia, Pericarditis, Perineurioma, Peripartum cardiomyopathy, Peripheral T-cell lymphoma, Peripheral neuropathy and optic atrophy, Peritoneal leiomyomatosis, Peritumoral oedema derived from brain tumours, Periventricular nodular heterotopia, Perlman syndrome, Pernicious anaemia, Perniola krajewska carnevale syndrome, Peroxisomal beta-oxidation disease, Perrault syndrome, Persistent Mullerian duct syndrome, Peters anomaly, Peters-plus syndrome, Petges-Clejat syndrome, Petit-Fryns syndrome, Petty laxova wiedemann syndrome, Peutz-Jeghers syndrome, Peyronie syndrome, Pfeiffer mayer syndrome, Pfeiffer palm teller syndrome, Pfeiffer rockelein syndrome, Pfeiffer syndrome, Pfeiffer-Kapferer syndrome, Pfeiffer-Singer-Zschiesche syndrome, Pfeiffer-Weber-Christian syndrome, Phacomatosis, Phaeochromocytoma, Phagocyte function anomaly, Phaver syndrome, Phelan-McDermid syndrome, Phenotypic diarrhoea, Phenylketonuria, Phocomelia, Phytosterolemia, Picardi-Lassueur-Little syndrome, Pick disease of brain, Piebaldism, Pierre Robin sequence associated with branchial archs anomalies, Pierre Robin sequence associated with collagen diseases, Pigeon-breeder's lung disease, Pillay syndrome, Pilomatrixoma, Pilotto syndrome, Pinheiro freire maia miranda syndrome, Pinsky-Di George-Harley syndrome, Pitt-Hopkins syndrome, Pitt-Williams brachydactyl), Pitt-rogers-danks syndrome, Pituitary adenoma, Pituitary agenesis, Pituitary hormone deficiency, Pituitary lactotrophic adenoma, Pityriasis rubra pilaris, Piussan-Lenaerts-Mathieu syndrome, Plasma cell tumour, Platelet function disease, Platyspondylic dysplasia, Plectin deficiency, Pleomorphic liposarcoma, Pleuro-pulmonary blastoma, Pleuro-pulmonary endometriosis, Plott syndrome, Plum syndrome, Plummer-Vinson syndrome, Pneumoblastoma, Pneumocystosis, Pneumonia caused by *Pseudomonas Aeruginosa*, Poikilo-dermatomyositis, Pollitt syndrome, Polyarteritis nodosa, Polyarthritis, Polycystic kidney disease, Polycystic liver disease, Polycystic ovarian disease, Polycythaemia, Polydactyl), Polyepiphyseal dysplasia, Polymicrogyria, Polymorphic catecholergic ventricular tachycardia, Polymyositis, Polyostotic fibrous dysplasia, Polyposis, Polysyndactyly-cardiac malformation, Pompe disease, Popliteal web syndrome, Porokeratosis, Porphyria, Portal hypertension, Portal vein thrombosis, Post polio syndrome, Post transplantation graft dysfunction, Post-poliomyelitis syndrome, Post-transplant lymphoproliferative disease, Post-traumatic syringomyelia, Postanginal sepsis secondary to orophyngeal infection, Posterior cortical atrophy, Postpartum cardiomyopathy, Postviral Fatigue Syndrome, Potocki-Shaffer syndrome, Potter sequence, Powell chandra saal syndrome, Powell venencie gordon syndrome, Prader-Willi syndrome, Prata liberal goncalves syndrome, Preauricular pits renal disease, Precursor B-cell acute lymphoblastic leukaemia, Precursor T-cell acute lymphoblastic leukaemia, Preeyasombat-Varavithya syndrome, Pregnancy-related cholestasis, Premature aging, Pressure-induced localized lipoatrophy, Prieto-Badia-Mulas syndrome, Prieur-Griscelli syndrome, Primary biliary cirrhosis, Primary ciliary dyskinesia, Primary cutaneous CD30-positive T-cell lymphoproliferative disorders, Primary effusion lymphoma, Primary effusion lymphoma associated with the human immunodeficiency virus (HIV) infection, Primary intestinal lymphangiectasia, Primary lateral sclerosis, Primary lipodystrophy, Primary lymphoedema, Primary pulmonary lymphoma, Primary sclerosing cholangitis, Primerose syndrome, Progeria, Progressive bulbar paralysis of childhood, Progressive cone dystrophy, Progressive diaphyseal dysplasia, Progressive massive osteolysis, Progressive nephropathy with hypertension, Progressive neuronal degeneration of childhood with liver disease, Prolactinoma, Propping Zerres syndrome, Prostate cancer, Proteus syndrome, Proud-Levine-Carpenter syndrome, Prune belly syndrome, Psoriatic arthritis, PTEN Hamartoma syndrome, Pterygia, Pudendal neuralgia, Pudendal neuropathy, Pulmonar arterioveinous aneurysm, Pulmonary Langerhans' cell histiocytosis, Pulmonary alveolar microlithiasis, Pulmonary alveolar proteinosis, Pulmonary aortic stenosis, Pulmonary arterial hypertension, Pulmonary arterio-veinous fistula, Pulmonary artery hypoplasia, Pulmonary atresia, Pulmonary blastoma, Pulmonary branch stenosis, Pulmonary endometriosis, Pulmonary haemosiderosis, Pulmonary insufficiency, Pulmonary lymphangiectasia, Pulmonary lymphangiomatosis, Pulmonary nodular lymphoid hyperplasia, Pulmonary supravalvular stenosis, Pulmonary surfactant protein anomalies, Pulmonary valve agenesis (PVA), Pulmonary venoocclusive disease, Pulp stones, Pulpal dysplasia, Puretic syndrome, Purtilo syndrome, Pycnodysostosis, Pyknoachondrogenesis, Pyknolepsy, Pyle disease, Pyoderma gangrenosum, Pyomyositis, Pyropoikilocytosis, Q fever, Qazi-Markouizos syndrome, Quattrin mcpherson syndrome, RAEB-1, RAPADILINO syndrome, RB-ILD, RECQ2, RECQL3, RHS, Rabson-Mendenhall syndrome, Radiation syndromes, Radio renal syndrome, Raine syndrome, Rajab-Spranger syndrome, Rambam-Hasharon syndrome, Rambaud galian syndrome, Ramon syndrome, Ramos arroyo clark syndrome, Ramsay hunt syndrome, Randall disease, Rapp-Hodgkin ectodermal dysplasia syndrome, Rapp-Hodgkin syndrome, Rasmussen johnsen thomsen syndrome, Rasmussen syndrome, Rathburn disease, Ray peterson scott syndrome, Raynaud phenomenon, Reardon-Baraitser syndrome, Reardon-Hall-Slaney syndrome, Recurrent hepatitis C virus induced liver disease in liver transplant recipients, Red cell aplasia, Refetoff syndrome, Reflex sympathetic dystrophy syndrome, Refsum disease, Reginato-Schiapachasse syndrome, Reifenstein syndrome, Reinhardt pfeiffer syndrome, Reiter's syndrome, Renal adysplasia, Renal cell carcinoma, Renal dysplasia, Renal glucosuria, Renal hypertension, Renal hypoplasia, Renal nutcracker syndrome, Renal tubular acidosis, Renal tubular disorder, Renal-coloboma syndrome, Rendu-Osler-Weber disease, Renier-Gabreels-Jasper syndrome, Renpenning syndrome, Resistance to activated protein C, Resistance to thyroid stimulating hormone, Respiratory bronchiolitis, Restless legs syndrome, Restrictive cardiomyopathy, Reticular perineurioma, Retinal arteriolar tortuosity, Retinal degeneration, Retinal dystrophy, Retinal hemorrhage, Retinoblastoma, Retinohepatoendocrinologic syndrome, Retinopathy of prematurity, Retinoschisis with early hemeralopia, Retinoschisis, Retraction syndrome, Retroperitoneal fibrosis, Rett like syndrome, Rett syndrome, Revesz-Debuse syndrome, Reye's syndrome, Reynolds syndrome, Rh deficiency syndrome, Rhabdomyosarcoma, Rheumatic fever, Rhizomelic dysplasia, Rhnull syndrome, Richards-Rundle syndrome, Richardson's syndrome, Richieri Costa-Guion Almeida-Cohen syndrome, Richieri costa da silva syndrome, Richieri costa gorlin syndrome, Richieri-Costa-Colletto syndrome, RichieriCosta-Pereira syndrome, Richner-Hanhart syndrome, Ricker syndrome, Rickettesiae disease, Riedel Thyroiditis, Rieger syndrome, Right atrium familial dilatation, Right ventricle hypoplasia, Rigid spine syndrome, Riley-Day syndrome, Riley-Smith syndrome, Rippberger aase syndrome, Rippling muscle disease, Ritscher schinzel syndrome, Rivera-Perez-Salas syndrome, Roberts syndrome, Robinow syndrome, Robinow-Sorauf syndrome, Robinow-Unger syndrome, Robinow-like syndrome, Roch-Leri mesosomatous lipomatosis, Rocky Mountain spotted fever, Rodini richieri costa syndrome, Roger disease, Roifman-Melamed syndrome, Rokitansky syndrome, Romano-Ward long QT syndrome, Rombo syndrome, Rommen mueller sybert syndrome, Rosai-Dorfman disease, Rosenberg lohr syndrome, Rosenberg Chutorian syndrome, Rothmund-Thomson syndrome, Rotor syndrome, Roy maroteaux kremp syndrome, Rozin-Hertz-Goodman syndrome, Rubinstein-Taybi syndrome, Rudd-Klimek syndrome, Rudiger syndrome, Russell Silver syndrome, Russell weaver bull syndrome, Rutherfurd syndrome, Ruvalcaba syndrome, Ruvalcaba-Myhre-Smith syndrome, SADDAN, SANDO, SAPHO syndrome, SC phocomelia, SCA, SCAN 2, SCAR1, SCARF syndrome, SCASI, SCD, SCID, SCLC, SE(M)D, SGBS, SGS, SHORT syndrome, SIADH, SIBIDS syndrome, SJS, SLK, SMD, SMEI, SMMCI, SOD, SOLAMEN syndrome, SPG, SPONASTRIME dysplasia, SPS, SRP, SUNCT syndrome, Saal-Greenstein syndrome, Saccharopinuria, Sack-Barabas syndrome, Saethre-Chotzen syndrome, Saito kuba tsuruta syndrome, Sakati syndrome, Sakati-Nyhan syndrome, Sakati-Nyhan-Tisdale syndrome, Salcedo syndrome, Salla disease, Salmonellosis, Salti salem syndrome, Sammartino decreccio syndrome, San Luis Valley syndrome, Sandhoff disease, Sandifer syndrome, Sandrow syndrome, Sanfilippo disease, Sanjad-Sakati syndrome, Santavuori disease, Santos-Mateus-Leal syndrome, Sarcocystosis, Sarcoidosis, Sarcosinemia, Sarcosporidiosis, Satoyoshi syndrome, Say barber hobbs syndrome, Say barber miller syndrome, Say field coldwell syndrome, Say meyer syndrome, Scarring in glaucoma filtration surgical procedures, Schaap taylor baraitser syndrome, Scheie syndrome, Scheuermann disease, Schilbach-Rott syndrome, Schilder disease, Schimke syndrome, Schimmelpenning syndrome, Schindler disease, Schinzel syndrome, Schisis association, Schistosomiasis, Schmidt syndrome, Schmitt gillenwater kelly syndrome, Schneckenbecken dysplasia, Schnitzler syndrome, Schofer-Beetz-Bohl syndrome, Scholte begeer van essen syndrome, Schopf-Schulz-Passarge syndrome, Schwannomatosis, Schwartz-Jampel syndrome, Scimitar syndrome, Scleroatrophic syndrome, Scleroderma, Scleromyxedema, Sclerosing mediastinitis, Sclerosteosis, Scott syndrome, Scott-Bryant-Graham syndrome, Scott-Taor syndrome, Seaver cassidy syndrome, Sebastian syndrome, Seckel like syndrome, Seckel syndrome, Sedlackova syndrome, Seemanova lesny syndrome, Segawa syndrome, Seghers syndrome, Seitelberger disease, Selig-Benacerraf-Greene syndrome, Sellars-Beighton syndrome, Sengers syndrome, Sengers-Hamel-Otten syndrome, Senior syndrome, Senior-Boichis syndrome, Senior-Loken syndrome, Sensenbrenner syndrome, Senter syndrome, Sepsis, Septic phlebitis of the internal jugular vein, Sequeiros sack syndrome, Servelle-Martorell syndrome, Setleis syndrome, Severe closed traumatic brain injury, Severe combined immunodeficiency T- B-, Severe combined immunodeficiency with hypereosinophilia, Severe combined immunodeficiency with leukopenia, Severe pneumococcemia, Sezary's lymphoma, Shapiro syndrome, Sharma kapoor ramji syndrome, Sharp syndrome, Sheehan syndrome, Shigellosis, Shokeir syndrome, Shone syndrome, Short QT syndrome, Short bowel syndrome due to necrotizing enterocolitis, Short bowel syndrome due to thrombosis, Short bowel syndrome, Shprintzen omphalocele syndrome, Shprintzen-Goldberg syndrome, Shulman syndrome, Shwachman-diamond syndrome, Shy-drager syndrome, Sialidosis, Sickle cell anaemia, Sideroblastic anaemia, Sidransky-Feinstein-Goodman syndrome, Siegler brewer carey syndrome, Silengo lerone pelizzo syndrome, Sillence syndrome, Simosa penchaszadeh bustos syndrome, Simpson dysmorphia syndrome (SDYS), Simpson-Golabi-Behmel syndrome, Sinding-Larsen-Johansson disease, Singh chhaparwal dhanda syndrome, Singh-Williams-McAlister syndrome, Single ventricular septal defect, Singleton-Merten dysplasia, Singleton-Merten syndrome, Sino-auricular heart block, Sinus node disease and myopia, Sipple syndrome, Sirenomelia, Sitosterolemia, Situs inversus viscerum-cardiopathy, Sjögren syndrome, Sjögren-Larsson syndrome, Skeletal dysplasia, Skeletal muscle disease, Skin collagen disease, Skin vascular disease, Sleep disorder, Sleeping seekness, Sly disease, Small bowel adenocarcinoma, Small bowel leiomyosarcoma, Small non-cleaved cell lymphoma, Smith martin dodd syndrome, Smith-Fineman-Myers syndrome, Smith-Lemli-Opitz syndrome, Smith-Magenis syndrome, Sneddon syndrome, Sneddon-Wilkinson disease, Snyder-Robinson syndrome, Soft tissue perineurioma, Soft tissue sarcomas, Sohval soffer syndrome, Solitary plasmacytoma, Solomon syndrome, Somatotroph adenoma, Sommer hines syndrome, Sommer rathbun battles syndrome, Sommer-Young-Wee-Frye syndrome, Sondheimer syndrome, Sonoda syndrome, Sorsby syndrome, Sorsby's fundus dystrophy, Sotos syndrome, Spastic paraplegia, Spellacy gibbs watts syndrome, Spherophakia-brachymorphia, Sphingolipidosis, Spina bifida, Spinal atrophy, Spirillosis, Splenic marginal zone lymphoma, Spondylarthropathy, Spondylo camptodactyly syndrome, Spondylocostal dysostosis, Spondyloenchondrodysplasia, Spondyloepiphyseal dysplasia, Spongy degeneration of central nervous system, Spongy myocardium, Spontaneous pneumothorax familial type, Sporotrichosis, Squamous cell carcinoma of head and neck, St Louis encephalitis, Stalker chitayat syndrome, Stampe sorensen syndrome, Stapedo-vestibular ankylosis, Staphylococcal necrotizing pneumonia, Staphylococcal scarlet fever, Staphylococcal toxic shock syndrome, Stargardt disease, Stark-Kaeser syndrome, Startle disease, Steatocystoma, Steele-Richardson-Olszewski disease, Stein-Leventhal syndrome, Steinert myotonic dystrophy, Steinfeld syndrome, Stern-Lubinsky-Durrie syndrome, Stevens-Johnson syndrome, Stickler syndrome, Stiff person syndrome, Still disease, Stimmler syndrome, Stoeling a de koomen davis syndrome, Stoll alembik finck syndrome, Stoll geraudel chauvin syndrome, Stoll kieny dott syndrome, Stoll-Levy-Francfort syndrome, Stomach cancer, Stormorken-Sjaastad-Langslet syndrome, Stratton garcia young syndrome, Stratton parker syndrome, Streptobacillosis, Streptococcal toxic-shock syndrome, Stress cardiomyopathie, Strumpell-Lorrain disease, Sturge-Weber syndrome, Stuve-Wiedemann dysplasia, Subcutaneous panniculitis-like T-cell lymphoma, Subpulmonary stenosis, Sucking/swallowing disorder, Sudden infant death syndrome, Sugarman syndrome, Sujansky-Leonard syndrome, Sulfocysteinuria, Summerskill-Walshe-Tygstrup syndrome, Summitt syndrome, Supravalvar aortic stenosis, Susac syndrome, Sutton disease II, Sweet syndrome, Swyer syndrome, Symphalangism, Syncopal paroxysmal tachycardia, Syncopal tachyarythmia, Syndromatic diarrhea, Synovialosarcoma, Synovitis, Synspondylism, Syntelencephaly, Syringocystadenoma papilliferum, Syringomyelia, Systemic capillary leak syndrome, Systemic lupus erythematosus, Systemic mastocytosis, Systemic scleroderma (systemic sclerosis), Systemic vasculitis, T cell immunodeficiency, T-cell leukaemia, T-cell chronic lymphocytic leukaemia, TAC, TAR syndrome, TCP, TDO syndrome, TEMF, TGA, TINU syndrome, TNF receptor 1 associated periodic syndrome, TOS, TRAPS syndrome, TTP, TTR amyloid cardiopathy, TTR amyloid neuropathy, Tabatznik syndrome, Takatsuki syndrome, Takayasu arteritis, Takotsubo cardiomyopathy, Tang hsi ryu syndrome, Tangier disease, Tardive dyskinesia, Tarsal Tunnel syndrome, Tarui disease, Tauopathy, Taussig-Bing syndrome, Tay syndrome, Tay-Sachs disease, Taybi syndrome, Taybi-Linder syndrome, Teebi al saleh hassoon syndrome, Teebi kaurah syndrome, Teebi naguib alawadi syndrome, Teebi shaltout syndrome, Telangiectasia, Telecanthus, Telfer sugar jaeger syndrome, Temtamy-Shalash syndrome, Ter Haar syndrome, Teratoma, Tetraamelia, Tetralogy of Fallot, Thakker donnai syndrome, Thalassaemia syndrome, Thanatophoric dysplasia, Theodore's syndrome, Thiele syndrome, Thiemann disease, Thies-Reis syndrome, Thomas jewett raines syndrome, Thomas syndrome, Thompson baraitser syndrome, Thomsen and Becker disease, Thong douglas ferrante syndrome, Thoracic aortic aneurysm and/or dissection, Thoracic outlet syndrome, Three M disease, Thromboangiitis obliterans, Thrombocytopaenia, Thrombocytopenic purpura autoimmune, Thrombocytopenic purpura idiopathic, Thrombocytosis, Thromboembolic pulmonary hypertension, Thrombotic disease of haematologic origin, Thymic aplasia, Thymic carcinoma, Thyroid tumor, Tick-borne encephalitis, Tietze syndrome, Timothy syndrome, Tollner horst manzke syndrome, Tolosa-Hunt syndrome, Tomaculous neuropathy, Tome brune fardeau syndrome, Toni-Debré-Fanconi disease, Tonoki-Ohura-Niikawa syndrome, TORCH syndrome, Toriello syndrome, Toriello-Carey syndrome, Toriello-Higgins-Miller syndrome, Toriello-Lacassie-Droste syndrome, Torres ayber syndrome, Tourette syndrome, Townes-Brocks syndrome, Toxocariasis, *Toxoplasma* embryopathy, Toxoplasmosis, Tracheopathia osteoplastica, Tranebjaerg-Svejgaard syndrome, Transmissible spongiform encephalopathies, Transposition of the great arteries with pulmonary stenosis, Transthyretin amyloid polyneuropathy, Treacher-Collins syndrome, Aspiration pneumotitis requiring intubation and mechanical ventilation, Cardiogenic shock, Treft-Sanborn-Carey syndrome, Trench fever, Trevor disease, Triatrial heart, Trichinosis, Tricho onychic dysplasia, Tricho-dento-osseous syndrome, Trichohepato-enteric syndrome, Trichorhinophalangeal, Trichorrhexis nodosa syndrome, Trichothiodystrophy, Tricuspid atresia, Triopia, Triple A syndrome, Triple H(HHH) syndrome, Triplo-X syndrome, Trisomy, Tritanopia, Trochlear dysplasia, Tropical calcific chronic pancreatitis, Tropical endomyocardial fibrosis, Trueb burg bottani syndrome, Tsao-Ellingson syndrome, Tsukahara-Kajii syndrome, Tsukuhara syndrome, Tsutsugamushi disease, Tsutsugamushi fever, Tuberculosis, Tuberous sclerosis, Tubular duplication of the oesophagus, Tubular dysplasia, Tubular renal disease-cardiomyopathy, Tubulointerstitial nephritis and uveitis syndrome, Tucker syndrome, Tuffli-Laxova syndrome, Tularaemia, Tungiasis, Tungland-Bellman syndrome, Tunnel subaortic stenosis, Turcot syndrome, Turner syndrome, Turner-Kieser syndrome, Twin.twin transfusion syndrome, Tylosis, ULD, UPDM, UPDP, USH, Uhl anomaly, Ulbright hodes syndrome, Ulcerative colitis, Ulerythema ophryogenesis, Ulick syndrome, Ullrich disease, Umbilical cord ulceration, Univentricular cardiopathy, Unverricht-Lundborg disease, Upington disease, Upshaw-Schulman syndrome, Urbach-Wiethe disease, Urban-Rogers-Meyer syndrome, Urban-Schosser-Spohn syndrome, Uremic pruritus, Urrets-Zavalia syndrome, Usher syndrome, Usual interstitial pneumonia (UIP), Uveitis, VIPoma, VMCM, VODI syndrome, VSD, VWS, Vagneur triolle ripert syndrome, Van Allen-Myhre syndrome, Van Benthem-Driessen-Hanveld syndrome, Van Bogaert disease, Van Der Woude syndrome, Van biervliet hendrickx van ertbruggen syndrome, Van de berghe-Dequeker syndrome, Van den Bosch syndrome, Van den ende brunner syndrome, Van der Knapp syndrome, Van goethem syndrome, Van maldergem wetzburger verloes syndrome, Van regemorter pierquin vamos syndrome, Varadi-Papp syndrome, Vascular leukoencephalopathy, Vasculitis, Vasquez-Hurst-Sotos syndrome, Vasterbotten dystrophy, Vein of Galen aneurysm, Venencie powell winkelmann syndrome, Ventricular septal defect, Ventricular septal defect with aortic insufficiency, Verloes-Gillerot-Fryns syndrome, Verloes bourguignon syndrome, Verloes david syndrome, Verloes van maldergem marneffe syndrome, Verloes-Deprez syndrome, Verloove vanhorick brubakk syndrome, Verneuil disease, Viljoen winship syndrome, Viljoen-Kallis-Voges syndrome, Viljoen-Smart syndrome, Viral hemorrhagic fever, Viral hepatitis, Viral vasculitis, Visceral neuropathy, Vitiligo, Vitreoretinal degeneration, Vogt-Koyanagi-Harada disease, Vohwinkel syndrome, Volcke-Soekarman syndrome, Von Gierke disease, Von Hippel-Lindau disease, Von Recklinghausen disease, Von Voss-Cherstvoy syndrome, Von Willebrand disease, Von hippel anomaly, Vsr syndrome, Vuopala disease, W syndrome, WAGR syndrome, WARBM1, WHIM syndrome, WL syndrome, WT limb-blood syndrome, Waaler-Aarskog syndrome, Waardenburg syndrome, Waardenburg-Shah syndrome, Wagner disease, Waisman syndrome, Waldenstrom macroglobulinemia, Waldmann disease, Walker-Dyson syndrome, Walker-Warburg syndrome, Wallis cremin beighton syndrome, Wallis zieff goldblatt syndrome, Warburg Micro syndrome, Warburg thomsen syndrome, Warburton-Anyane-Yeboa syndrome, Warman-Mulliken-Hayward syndrome, Water-West syndrome, Waterhouse-Friedrickson syndrome, Watson syndrome, Weaver like syndrome, Weaver syndrome, Weaver-Williams syndrome, Weber-Christian disease (WCD), Weber-Christian panniculitis, Webster deming syndrome, Wegener granulomatosis, Weil syndrome, Weill-Marchesani syndrome, Weismann Netter Stuhl syndrome, Weissenbacher-Zweymuller syndrome, Wellesley-Carman-French syndrome, Wells syndrome, Wells-Jankovic syndrome, Werdnig-Hoffmann disease, Wermer syndrome, Werner syndrome, Wernicke's encephalopathy, Wernicke-Korsakoff syndrome, West syndrome, West-Nile encephalitis, Westerhof-Beemer-Cormane syndrome, Western equine encephalomyelitis, Westphall disease, Whelan syndrome, Whipple disease, Whistling face syndrome, Whooping cough, Whyte-Murphy syndrome, Wieacker-Wolff syndrome, Wiedemann grosse dibbern syndrome, Wiedemann oldigs oppermann syndrome, Wiedemann-Beckwith syndrome, Wiedemann-Rautenstrauch syndrome, Wildervanck syndrome, Wilkes stevenson syndrome, Wilkie-Taylor-Scambler syndrome, Willebrand disease, Willi-Prader syndrome, Williams syndrome, Williams-Beuren syndrome, Wilms tumor, Wilson disease, Wilson-Turner syndrome, Winchester disease, Winkelman bethge pfeiffer syndrome, Winkelmann's cytophagic panniculitis, Winship viljoen leary syndrome, Winter harding hyde syndrome, Winter-Shortland-Temple syndrome, Wiskott-Aldrich syndrome, Wissler-Fanconi syndrome, Witkop syndrome, Wittwer syndrome, Wolcott-Rallison syndrome, Wolf-Hirschhorn syndrome, Wolff zimmermann syndrome, Wolff-Parkinson-White syndrome, Wolfram syndrome, Wolman disease, Woodhouse sakati syndrome, Woods black norbury syndrome, Woods leversha rogers syndrome, Woods-Crouchman-Huson syndrome, Worster drought syndrome, Worth syndrome, Wrinkly skin syndrome, Wyburn-Mason syndrome, XHIGM, XLAG syndrome, XMEA, XP, Xanthic urolithiasis, Xanthinuria, Xanthogranulomatous hypophysitis, Xanthomatosis cerebrotendinous, Xerocytosis, Xeroderma pigmentosum, Yellow fever, Yellow nail syndrome, Yersiniosis, Yorifuji-Okuno syndrome, Yoshimura-takeshita syndrome, Young maders syndrome, Young syndrome, Young-Hugues syndrome, Young-Simpson syndrome, Yunis-Varon syndrome, ZASP-related myofibrillar myopathy, Zadik-Barak-Levin syndrome, Zellweger syndrome, Zellweger-like syndrome, Zimmer phocomelia, Zimmerman laband syndrome, Zinsser-Cole-Engman syndrome, Zlotogora-Ogur syndrome, Zlotogura-Martinez syndrome, Zollinger-Ellison syndrome, Zori stalker williams syndrome, Zunich-Kaye syndrome, Zygomycosis, 2,8 dihydroxy-adenine urolithiasis, 2-aminoadipic aciduria, 2-hydroxyglutaricaciduria, 2-methylbutyric aciduria, 3 hydroxyisobutyric aciduria, 3-hydroxy-3-methylglutaric aciduria, 3-methylcrotonylglycinuria, 3-methylglutaconic aciduria, 3C syndrome, 3M syndrome, 4-hydroxybutyricaciduria, Visceral leishmaniasis, Vernal keratoconjunctivitis, UV-A and visible light-induced photosensitivity disorders (chronic actinic dermatitis, cutaneous porphyrias, actinic prurigo and solar urticaria), Uremic pruritus, Tricyclic antidepressants poisoning, Traumatic spinal cord injury, Renal cell carcinoma, Superficial bladder cancer, *Staphylococcus aureus* bacteraemia, Spinal cord injury, Spina bifida, Soft tissue sarcoma, Small cell lung cancer, Sickle cell disease, Severe myoclonic epilepsy in infancy, Severe combined immunodeficiency (SCID), Severe closed traumatic brain injury, Retinopathy of prematurity, Retinitis pigmentosa, Respiratory distress syndrome in premature neonates of less than 32 weeks of gestational age, Recurrent hepatitis C virus induced liver disease in liver transplant recipients, Radiation proctitis, *Pseudomonas aeruginosa* lung infection in cystic fibrosis, Progressive myoclonic epilepsies, Primary malignant bone tumors, Primary apnoea of premature newborns, Post-transplant lymphoproliferative disorders, Post-neonatal intracerebral haemorrhage, Post transplantation graft dysfunction, Polycythemia vera, Peritumoral oedema derived from brain tumors, Peripheral T-cell lymphoma (nodal, other extranodal and leukaemic/ disseminated), Ductus arteriosus in premature neonates of less than 34 weeks of gestational age, Partial deep dermal and full thickness burns, Paroxysmal nocturnal haemoglobinuria, Pancreatic cancer, Painful HIV-associated neuropathy, Ovarian cancer, Osteosarcoma, Orthostatic hypotension in patients with pure autonomic failure, Orthostatic hypotension in patients with multiple system atrophy, Ornithine-transcarbamylase deficiency, Oral mucositis in head and neck cancer patients undergoing radiation therapy, Oesophageal cancer, Non-traumatic osteonecrosis, Non-ketotic hyperglycinaemia, Non-infectious uveitis affecting the posterior segment of the eye, Non-24-hour sleep-wake disorders in blind people with no light perception, Neuroblastoma, Neovascular glaucoma, Nephritic syndrome, Myelodysplastic syndromes, Myasthenia gravis, Moderate and severe traumatic brain injury, Metachromatic leukodystrophy, Medullary thyroid carcinoma, Mastocytosis, Mantle cell lymphoma, Malignant melanoma, Malignant gastrointestinal stromal tumors, Malabsorption due to exocrine pancreatic enzyme insufficiency, Low flow priapism, Lipoprotein lipase deficiency, Ligneous conjunctivitis, Leber's hereditary optic neuropathy, Leber's congenital amaurosis, Late onset sepsis in premature infants of less than or equal to 32 weeks gestational age, Juvenile myelomonocytic leukaemia, Japanese encephalitis, Intestinal graft-versus-host disease, Indolent non-Hodgkin's lymphoma, Inborn errors in primary bile acid synthesis, Hyperphenylalaninemia, Hypereosinophilic syndrome, Glioma, High-grade dysplasia in Barrett's oesophagus, Herpes simplex virus stromal keratitis, Hereditary factor XIII deficiency, Hepatocellular carcinoma, Hepatitis B re-infection following liver transplantation, Hepatic veno-occlusive disease, Gram negative bacterial lung infection in cystic fibrosis, Gastric cancer, Gamma sarcoglycanopathy, Follicular lymphoma, Familial adenomatous polyposis, Emphysema secondary to congenital alpha-1 antitrypsin deficiency, Duchenne muscular dystrophy, Diffuse large B cell lymphoma, Diffuse alveolar haemorrhage, Diarrhoea associated with intestinal microsporidial infection, Cutaneous T-cell lymphoma, Cutaneous forms of lupus erythematosus, Cushing's syndrome secondary to ectopic ACTH secretion, Corneal graft rejection, Congenital venous malformations, Congenital lymphatic malformations, Congenital alpha-1 antitrypsin deficiency, Congenital adrenal hyperplasia, Chronic pain, Cocaine poisoning, Chronic myeloid leukaemia, Chronic lymphocytic leukaemia, Chronic iron overload requiring chelation therapy, Chronic idiopathic myelofibrosis, Chronic eosinophilic leukaemia and the hypereosinophilic syndrome, Cholangiocarcinoma, Charcot-Marie-Tooth disease type 1A, Cardiogenic shock, Bronchopulmonary dysplasia in premature neonates of less than 30 weeks of gestational age, B-cell chronic lymphocytic leukemia, Autoimmune uveitis, Atypical Haemolytic Uraemic Syndrome (aHUS) associated with an inherited abnormality of the complement system, Aspiration pneumonitis requiring intubation and mechanical ventilation, Aneurysmal subarachnoid haemorrhage, Anaplastic thyroid cancer, Anal fistula, Acute sensorineural hearing loss (acute acoustic trauma, sudden deafness and surgery induced acoustic trauma), Acute peripheral arterial occlusion, Acute intermittent porphyria, Active phase of Peyronie's disease, Acanthamoeba keratitis, A-mannosidosis, 5q spinal muscular atrophy, Cavopulmonary Anastomosis, Atrial Septal Defects (ASD), Partial Anomalous Pulmonary Venous Return, Persistent Common Atrio Ventricular Canal Endocardial Cushion Defect. Ostium Primum, Single Atrium, Patent Ductus Arteriosus (PDA), Total Anomalous Pulmonary Venous Return, Ventricular Septal Defects (VSD), Pulmonary Valve Stenosis, Pulmonary Artery Stenosis and Stenosis of Pulmonary Artery Branches, Pulmonary Atresia with Intact Ventricular Septum, Congenital Mitral Valve Disease, Aortic Valvular Stenosis and Congenital Aortic Valvular Regurgitation, Supravalvular Aortic Stenosis, Transposition of the Great Arteries, Double Outlet Right Ventricle, Corrected Transposition of the Great Arteries, Truncus Arteriosus, Aorto Pulmonary Window, Tricuspid Atresia, Ebstein Anomaly, Malformations of the Vena Cava, Coarctation of the Aorta, Atresia of Aortic Valve, Anomalies of the Aortic Arch, Anomalous Origin of the Right Subclavian Artery with Coarctation of the Aorta, Idiopathic Dilatation of the Pulmonary Artery, Left Pulmonary Artery Arising from Right Pulmonary Artery, Dextrocardia-Situs Inversus Totalis, Association of Heart Malformations with Asplenia, Malformations of the Vena Cava, Congenital Coronary Artery Arterio-Venous Fistula, Abnormal Origin of the Coronary Arteries, Aneurysm of the Sinus of Valsalva (Aortic Sinus Aneurysm), Endocardial Fibroelastosis, Idiopathic Hypertrophic Subaortic Stenosis (IHSS), Mitral Valve Prolapse-Barlow's Syndrome, Hypoplastic Left Heart.

Pharmaceutical Compositions

Still another aspect of the present invention relates to the use of the peptide according to claim 1 as an active ingredient, together with at least one pharmaceutically acceptable carrier, excipient and/or diluents for the manufacture of a pharmaceutical composition for the treatment and/or prophylaxis of cancer, an autoimmune disease, a fibrotic disease, an inflammatory disease, a neurodegenerative disease, an infectious disease, a lung disease, a heart and vascular disease or a metabolic disease or any other disease disclosed herein.

Such pharmaceutical compositions comprise the peptide as an active ingredient, together with at least one pharmaceutically acceptable carrier, excipient, binders, disintegrates, glidents, diluents, lubricants, coloring agents, sweetening agents, flavoring agents, preservatives or the like. The pharmaceutical compositions of the present invention can be prepared in a conventional solid or liquid carrier or diluents and a conventional pharmaceutically-made adjuvant at suitable dosage level in a known way.

Preferably the peptide is suitable for intravenous administration or suitable for oral administration or suitable for administration by inhalation.

Administration forms include, for example, pills, tablets, film tablets, coated tablets, capsules, liposomal formulations, micro- and nano-formulations, powders and deposits. Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain the peptide according to the present invention.

The present invention also includes the mammalian milk, artificial mammalian milk as well as mammalian milk substitutes as a formulation for oral administration of the peptide to newborns, toddlers, and infants, either as pharmaceutical preparations, and/or as dietary food supplements.

The peptide of the invention can also be administered in form of its pharmaceutically active salts. Suitable pharmaceutically active salts comprise acid addition salts and alkali or earth alkali salts. For instance, sodium, potassium, lithium, magnesium or calcium salts can be obtained.

The peptide of the invention forms pharmaceutically acceptable salts with organic and inorganic acids. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphersulfonic acid, china acid, mandelic acid, o-methylmandelic acid, hydrogen-benzenesulfonic acid, picric acid, adipic acid, D-o-tolyltartaric acid, tartronic acid, a-toluic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

The pharmaceutical compositions according to the present invention will typically be administered together with suitable carrier materials selected with respect to the intended form of administration, i.e. for oral administration in the form of tablets, capsules (either solid filled, semi-solid filled or liquid filled), powders for constitution, aerosol preparations consistent with conventional pharmaceutical practices. Other suitable formulations are gels, elixirs, dispersible granules, syrups, suspensions, creams, lotions, solutions, emulsions, suspensions, dispersions, and the like. Suitable dosage forms for sustained release include tablets having layers of varying disintegration rates or controlled release polymeric matrices impregnated with the active components and shaped in tablet form or capsules containing such impregnated or encapsulated porous polymeric matrices. The pharmaceutical compositions may be comprised of 5 to 95% by weight of the peptide.

As pharmaceutically acceptable carrier, excipient and/or diluents can be used lactose, starch, sucrose, cellulose, magnesium stearate, dicalcium phosphate, calcium sulfate, talc, mannitol, ethyl alcohol (liquid filled capsules).

Suitable binders include starch, gelatin, natural sugars, corn sweeteners, natural and synthetic gums such as acacia, sodium alginate, carboxymethyl-cellulose, polyethylene glycol and waxes. Among the lubricants that may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The peptide of the present invention may also be deliverable transdermally. The transdermal compositions may take the form of creams, lotions, aerosols and/or emulsions and can be included in a transdermal patch of the matrix or reservoir type as are conventional in the art for this purpose.

The transdermal formulation of the peptide of the invention is understood to increase the bioavailability of said peptide into the circulating blood. One problem in the administration of peptides is the loss of bioactivity due to the formation of insolubles in aqueous environments or due to degradation. Therefore stabilization of peptides for maintaining their fluidity and maintaining their biological activity upon administration to the patients in need thereof needs to be achieved.

Prior efforts to provide active agents for medication include incorporating the medication in a polymeric matrix whereby the active ingredient is released into the systemic circulation. Known sustained-release delivery means of active agents are disclosed, for example, in U.S. Pat. Nos. 4,235,988, 4,188,373, 4,100,271, 4,474,751, 4,474,752, 4,474,753, or 4,478,822 relating to polymeric pharmaceutical vehicles for delivery of pharmaceutically active chemical materials to mucous membranes. The pharmaceutical carriers are aqueous solutions of certain polyoxyethylene-polyoxypropylene condensates. These polymeric pharmaceutical vehicles are described as providing for increased drug absorption by the mucous membrane and prolonged drug action by a factor of two or more. The substituents are block copolymers of polyoxypropylene and polyoxyethylene used for stabilization of drugs such as insulin.

Aqueous solutions of polyoxyethylene-polyoxypropylene block copolymers (poloxamers) are useful as stabilizers for the peptide. Aside from serving as a stabilizer for the peptide, poloxamers provide excellent vehicles for the delivery of the peptide, and they are physiologically acceptable. Poloxamers, also known by the trade name Pluronics (e.g. Pluronic F127, Pluronic P85, Pluronic F68) have surfactant properties that make them useful in industrial applications. Among other things, they can be used to increase the water solubility of hydrophobic, oily substances or otherwise increase the miscibility of two substances with different hydrophobicities. For this reason, these polymers are commonly used in industrial applications, cosmetics, and pharmaceuticals. They have also been used as model systems for drug delivery applications. In situ gelation of pharmaceutical compositions based on poloxamer that are biologically triggered are known in the art (e.g. U.S. Pat. No. 5,256,396), describing compositions containing poloxamer 407 and water at specified concentrations.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refers to the active ingredients dispersed or solubilized in a hydrophilic semi-solid matrix.

Powders for constitution refer to powder blends containing the active ingredients and suitable diluents which can be suspended in water or juices. One example for such an oral administration form for newborns, toddlers and/or infants is a human breast milk substitute which is produced from milk powder and milk whey powder, optionally and partially substituted with lactose.

Human breast milk is a complex fluid, rich in nutrients and in non-nutritional bioactive components. It contains all of the nutrients needed by the newborn baby. These include the metabolic components (fat, protein, and carbohydrates), water, and the raw materials for tissue growth and development, such as fatty acids, amino acids, minerals, vitamins, and trace elements.

More than 98% of the fat in is in the form of triglycerides. Oleic acid and palmitic acid are the most abundant fatty acids in breastmilk triglycerides, with comparatively high proportions of the essential fatty acids, and linolenic acid, followed by long-chain polyunsaturated fatty acids, such as arachidonic acid and docosahexaenoic acid. These long-chain fatty acids are constituents of brain and neural tissue and are needed in early life for mental and visual development. The lipid component of breast milk is the transport vehicle for fat-soluble micronutrients such as prostaglandins and vitamins A, D, E, and K.

Proteins account for approximately 75% of the nitrogen-containing compounds in breast milk. Non-protein nitrogen substances include urea, nucleotides, peptides, free amino acids, and DNA. The proteins of breast milk can be divided into two categories: micellar caseins and aqueous whey proteins, present in the ratio of about 40:60. Casein forms micelles of relatively small volume and produces a soft, flocculent curd in the infant's stomach. The major whey proteins are lactalbumin, lactoferrin, secretory IgA, and serum albumin, with a large number of other proteins and peptides present in smaller amounts.

The principal carbohydrate is lactose, a disaccharide produced in the mammary epithelial cell from glucose by a reaction involving lactalbumin. In addition to the nutritional components, breast milk contains a wealth of bioactive components that have beneficial non-nutritional functions. These include a wide range of specific and non-specific antimicrobial factors; cytokines and anti-inflammatory substances; and hormones, growth modulators, and digestive enzymes (Table 1), many of which have multiple activities. These components may be of particular importance for young infants because of the immaturity of the host defense and digestive systems early in life.

TABLE 4

Examples of the non-nutritional components of breast milk

Antimicrobial factors secretory IgA, IgM, IgG
lactoferrin
lysozyme
complement C3
leucocytes
*bifidus* factor
lipids and fatty acids
antiviral mucins, GAGs
oligosaccharides Cytokines and anti-inflammatory factors tumor necrosis factor
interleukins
interferons
prostaglandins
antichymotrypsin
antitrypsin
platelet-activating factor Hormones feedback inhibitor of lactation (FIL)
insulin
prolactin
thyroid hormones
corticosteroids
ACTH
oxytocin
calcitonin
parathyroid hormone
erythropoietin Growth factors epidermal (EGF)
nerve (NGF)
insulin-like (IGF)
transforming (TGF)
taurine
polyamines Digestive enzymes amylase
bile acid-stimulating esterase
bile acid-stimulating lipases
lipoprotein lipase Transporters lactoferrin (Fe)
folate binder
cobalamin binder
IgF binder
thyroxine binder
corticosteroid binder Besides breast milk, infant formula is the only other infant milk which the medical community considers nutritionally acceptable for infants under the age of one year. Cow's milk is not recommended because of its high protein and electrolyte (salt) content which may harm infant's immature kidneys. The nutrient content of infant formula should comprise: Protein, Fat, Linoleic acid, Vitamins: A, C, D, E, K, thiamin (B1), riboflavin (B2), B6, B12, Niacin, Folic acid, Pantothenic acid, Calcium, Metals: magnesium, iron, zinc, manganese, copper; Phosphorus, Iodine, Sodium chloride, Potassium chloride. In addition, formulas not made with cow's milk must include biotin, choline, and inositol. Hypoallergenic formulas reduce the likelihood of certain medical complications in babies with specific health problems. Baby formula can be synthesized from raw amino acids. This kind of formula is sometimes referred to as elemental infant formula or as medical food because of its specialized nature. Powder blends containing the active ingredients and suitable diluents which can be suspended in water or juices can be produced by spray drying.

Spray drying has been found the most suitable process for removing the last part of the water, since spray drying can convert milk concentrate into a powder while still keeping the valuable properties of the milk. The principle of all spray dryers is to transform the concentrate into many small droplets which are then exposed to a fast current of hot air. Because of the very large surface area of the droplets, the water evaporates almost instantaneously and the droplets are transformed into powder particles.

Powdered milk is a powder made from dried milk solids. Powdered milk has a far longer shelf life than liquid milk and does not need to be refrigerated due to its low moisture content.

Instant milk powder is produced by partially rehydrating the dried milk powder particles causing them to become sticky and agglomerate. The water is then removed by drying resulting in an increased amount of air incorporated between the powder particles.

Milk powder manufacture is a process carried out on a large scale. It involves the gentle removal of water, while retaining all the desirable natural properties of the milk like colour, flavour, solubility, nutritional value.

Milk powder process includes spray drying, fluid bed processing, extraction, evaporation and freeze drying. Other processes are freeze concentration, filteration, and homogenisation.

The artificial mother milk formulations or mother milk substitutes of the present invention are preferably prepared by adding to a mother milk formulation including commercially available mother milk formulations especially in power form the peptide of the present invention. The peptide is preferably added in an amount of 3-100 µg peptide or per 100 ml (commercially available) mother milk formulation, more preferably in an amount of 5-70 µg/100 ml and most preferably in an amount of 10-40 µg/100 ml mother milk formulation.

Suitable diluents are substances that usually make up the major portion of the composition or dosage form. Suitable diluents include sugars such as lactose, sucrose, mannitol and sorbitol, starches derived from wheat, corn rice and potato, and celluloses such as microcrystalline cellulose. The amount of diluents in the composition can range from about 5 to about 95% by weight of the total composition, preferably from about 25 to about 75%, more preferably from about 30 to about 60% by weight, and most preferably from about 40 to 50% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 1 to about 40% by weight of the composition, preferably 2 to about 30% by weight of the composition, more preferably from about 3 to 20% by weight of the composition, and most preferably from about 5 to about 10% by weight.

Binders characterize substances that bind or "glue" powders together and make them cohesive by forming granules, thus serving as the "adhesive" in the formulation. Binders add cohesive strength already available in the diluents or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 1 to 30% by weight of the composition, preferably from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.05 to about 15% by weight of the composition, preferably 0.2 to about 5% by weight of the composition, more preferably from about 0.3 to about 3%, and most preferably from about 0.3 to about 1.5% by weight of the composition.

Glidents are materials that prevent caking and improve the flow characteristics of granulations, so that flow is smooth and uniform. Suitable glidents include silicon dioxide and talc. The amount of glident in the composition can range from about 0.01 to 10% by weight of the composition, preferably 0.1% to about 7% by weight of the total composition, more preferably from about 0.2 to 5% by weight, and most preferably from about 0.5 to about 2% by weight.

Coloring agents are excipients that provide coloration to the composition or the dosage form. Such excipients can include food grade dyes and food grade dyes adsorbed onto a suitable adsorbent such as clay or aluminum oxide. The amount of the coloring agent can vary from about 0.01 to 10% by weight of the composition, preferably from about 0.05 to 6% by weight, more preferably from about 0.1 to about 4% by weight of the composition, and most preferably from about 0.1 to about 1%.

The peptide of the invention can be used to form multiparticulates, discrete particles, well known dosage forms, whose totality represents the intended therapeutically useful dose of a drug. When taken orally, multiparticulates generally disperse freely in the gastrointestinal tract, and maximize absorption. A specific example is described in U.S. Pat. No. 6,068,859, disclosing multiparticulates that provide controlled release of azithromycin. Another advantage of the multiparticulates is the improved stability of the drug. The poloxamer component of the multiparticulate is very inert, thus minimizing degradation of the drug.

However, formulation problems result from the melt-congeal process often used to form multiparticulates. The multiparticulates are preferably formed into round beads or spheres. Some carriers, when melted and then solidified, do not form round beads but may solidify into rods, strings, or other non-spherical shapes. The result is very irregularly shaped multiparticulates that are difficult to process into dosage forms. This problem is solved by e.g. WO 2007104173 where the particles consist of a poloxamer, a resin, and/or a tocopherol, creating together with the medicament (e.g. insulin) micelles. Micelle formation is essential for the absorption of many nutrients within the human body. Bile salts formed in the liver and secreted by the gall bladder allow micelles of fatty acids to form. This allows the absorption of complicated lipids and lipid soluble vitamins within the micelle by the small intestine. Micelles are approximately spherical in shape. Preferably, peptide of the invention are formulated with a poloxamer and a resin to form micelles suitable for oral administration to patients in need of the medicament.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Other preferred pharmaceutical compositions are buffered solutions. The term buffer, buffer system, buffer solution and buffered solution, when used with reference to hydrogen-ion concentration or pH, refers to the ability of a system, particularly an aqueous solution, to resist a change of pH on adding acid or alkali, or on dilution with a solvent. Preferred buffer systems can be selected from the group consisting of formate (pKa=3.75), lactate (pKa=3.86), benzoic acid (pKa=4.2) oxalate (pKa=4.29), fumarate (pKa=4.38), aniline (pKa=4.63), acetate buffer (pKa=4.76), citrate buffer (pKa2=4.76, pKa3=6.4), glutamate buffer (pKa=4.3), phosphate buffer (pKa=7.20), succinate (pKa1=4.93; pKa2=5.62), pyridine (pKa=5.23), phthalate (pKa=5.41); histidine (pKa=6.04), MES (2-(N-morpholino)ethanesulphonic acid; pKa=6.15); maleic acid (pKa=6.26); cacodylate (dimethylarsinate, pKa=6.27), carbonic acid (pKa=6.35), ADA (N-(2-acetamido)imino-diacetic acid (pKa=6.62); PIPES (4-piperazinebis-(ethanesulfonic acid; BIS-TRIS-propane (1,3-bis[tris(hydroxymethyl)methylamino]-propane), pKa=6.80), ethylendiamine (pKa=6.85), ACES 2-[(2-amino-2-oxoethyl)amino]ethanesulphonic acid; pKa=6.9), imidazole (pKa=6.95), MOPS (3-(N-morphin)-propansulfonic acid; pKa=7.20), diethylmalonic acid (pKa=7.2), TES (2-[tris (hydroxymethyl)methyl]amino ethanesulphonic acid; pKa=7.50) and HEPES (N-2-hydroxylethylpiperazin-N'-2-ethansulfonic acid; pKa=7.55) buffers or other buffers having a pKa between 3.8 to 7.7.

Preferred is the group of carboxylic acid buffers such as acetate and carboxylic diacid buffers such as fumarate, tartrate and phthalate and carboxylic triacid buffers such as citrate. Another group of preferred buffers is represented by inorganic buffers such as sulfate, borate, carbonate, oxalate, calcium hydroxyde and phosphate buffers. Another group of preferred buffers are nitrogen containing buffers such as imidazole, diethylenediamine, and piperazine.

Also preferred are sulfonic acid buffers such as TES, HEPES, ACES, PIPES, [(2-hydroxy-1,1-bis(hydroxymethyl)ethyl)amino]-1-propanesulfonic acid (TAPS), 4-(2-hydroxyethyl)piperazine-1-propanesulfonic acid (EPPS), 4-Morpholinepropanesulfonic acid (MOPS) and N,N-bis(2-hydroxyethyl)-2-aminoethanesulfonic acid (BES).

Another group of preferred buffers are glycine buffers such as glycine, glycyl-glycine, glycyl-glycyl-glycine, N,N-bis(2-hydroxyethyl)glycine and N-[2-hydroxy-1,1-bis(hydroxymethyl)ethyl]glycine (Tricine).

Preferred are also amino acid buffers such as glycine, alanine, valine, leucine, isoleucine, serine, threonine, phenylalanine, tyrosine, tryptophane, lysine, arginine, histidine, aspartate, glutamate, asparagine, glutamine, cysteine, methionine, proline, 4-hydroxyproline, N,N,N-trimethyllysine, 3-methylhistidine, 5-hydroxylysine, O-phosphoserine, γ-carboxyglutamate, ε-N-acetyllysine, ω-N-methylarginine, citrulline, ornithine and derivatives thereof.

TABLE 5

Also preferred are the following buffers:

| effective pH range | pKa 25° C. | buffer |
| --- | --- | --- |
| 2.7-4.2 | 3.40 | malate (pK1) |
| 3.0-4.5 | 3.75 | formate |
| 3.0-6.2 | 4.76 | citrate (pK2) |
| 3.2-5.2 | 4.21 | succinate (pK1) |
| 3.6-5.6 | 4.76 | acetate |
| 3.8-5.6 | 4.87 | propionate |
| 4.0-6.0 | 5.13 | malate (pK2) |
| 4.9-5.9 | 5.23 | pyridine |
| 5.0-6.0 | 5.33 | piperazine (pK1) |
| 5.0-7.4 | 6.27 | cacodylate |
| 5.5-6.5 | 5.64 | succinate (pK2) |
| 5.5-6.7 | 6.10 | MES |
| 5.5-7.2 | 6.40 | citrate (pK3) |
| 5.5-7.2 | 6.24 | maleate (pK2) |
| 5.5-7.4 | 1.70, 6.04, 9.09 | histidine |
| 5.8-7.2 | 6.46 | bis-tris |
| 5.8-8.0 | 7.20 | phosphate (pK2) |
| 6.0-12.0 | 9.50 | ethanolamine |
| 6.0-7.2 | 6.59 | ADA |
| 6.0-8.0 | 6.35 | carbonate (pK1) |
| 6.1-7.5 | 6.78 | ACES |
| 6.1-7.5 | 6.76 | PIPES |
| 6.2-7.6 | 6.87 | MOPSO |
| 6.2-7.8 | 6.95 | imidazole |
| 6.3-9.5 | 6.80, 9.00 | BIS-TRIS propane |
| 6.4-7.8 | 7.09 | BES |
| 6.5-7.9 | 7.14 | MOPS |
| 6.8-8.2 | 7.48 | HEPES |
| 6.8-8.2 | 7.40 | TES |
| 6.9-8.3 | 7.60 | MOBS |
| 7.0-8.2 | 7.52 | DIPSO |
| 7.0-8.2 | 7.61 | TAPSO |
| 7.0-8.3 | 7.76 | triethanolamine (TEA) |
| 7.0-9.0 | 0.91, 2.10, 6.70, 9.32 | pyrophosphate |
| 7.1-8.5 | 7.85 | HEPPSO |
| 7.2-8.5 | 7.78 | POPSO |

Preferred are the buffers having an effective pH range of from 2.7 to 8.5, and more preferred of from 3.8 to 7.7. The effective pH range for each buffer can be defined as pKa−1 to pKa+1, where Ka is the ionization constant for the weak acid in the buffer and pKa=−log K.

Most preferred are buffers suitable for pharmaceutical use e.g. buffers suitable for administration to a patient such as acetate, carbonate, citrate, fumarate, glutamate, lactate, phosphate, phthalate, and succinate buffers. Particularly preferred examples of commonly used pharmaceutical buffers are acetate buffer, citrate buffer, glutamate buffer and phosphate buffer. Also most preferred is the group of carboxylic acid buffers. The term "carboxylic acid buffers" as used herein shall refer to carboxylic mono acid buffers and carboxylic diacid buffers as well as carboxylic triacid buffers.

Of course also combinations of buffers, especially of the buffers mentioned herein are useful for the present invention.

Some suitable pharmaceutical buffers are a citrate buffer (preferably at a final formulation concentration of from about 20 to 200 mM, more preferably at a final concentration of from about 30 to 120 mM) or an acetate buffer (preferably at a final formulation concentration of about 20 to 200 mM) or a phosphate buffer (preferably at a final formulation concentration of about 20 to 200 mM).

Techniques for the formulation and administration of the peptide of the present invention may be found in "Remington's Pharmaceutical Sciences" Mack Publishing Co., Easton Pa. A suitable composition comprising the peptide mentioned herein may be a solution of the peptide in a suitable liquid pharmaceutical carrier or any other formulation such as tablets, pills, film tablets, coated tablets, dragees, capsules, powders and deposits, gels, syrups, slurries, suspensions, emulsions, and the like.

A particularly preferred pharmaceutical composition is a lyophilised (freeze-dried) preparation (lyophilisate) suitable for administration by inhalation or for intravenous administration. To prepare the preferred lyophilised preparation the peptide of the invention are solubilised in a 4 to 5% (w/v) mannitol solution and the solution is then lyophilised. The mannitol solution can also be prepared in a suitable buffer solution as described above.

Further examples of suitable cryo-/lyoprotectants (otherwise referred to as bulking agents or stabilizers) include thiol-free albumin, immunoglobulins, polyalkyleneoxides (e.g. PEG, polypropylene glycols), trehalose, glucose, sucrose, sorbitol, dextran, maltose, raffinose, stachyose and other saccharides (cf. for instance WO 97/29782), while mannitol is used preferably. These can be used in conventional amounts in conventional lyophilization techniques. Methods of lyophilisation are well known in the art of preparing pharmaceutical formulations.

For administration by inhalation the particle diameter of the lyophilised preparation is preferably between 2 to 5 µm, more preferably between 3 to 4 µm. The lyophilised preparation is particularly suitable for administration using an inhalator, for example the OPTINEB® or VENTA-NEB® inhalator (NEBU-TEC, Elsenfeld, Germany). The lyophilised product can be rehydrated in sterile distilled water or any other suitable liquid for inhalation administration.

Alternatively for intravenous administration the lyophilised product can be rehydrated in sterile distilled water or any other suitable liquid for intravenous administration.

After rehydration for administration in sterile distilled water or another suitable liquid the lyophilised preparation should have the approximate physiological osmolality of the target tissue for the rehydrated peptide preparation i.e. blood for intravenous administration or lung tissue for inhalation administration. Thus it is preferred that the rehydrated formulation is substantially isotonic.

The preferred dosage concentration for either intravenous, oral, or inhalation administration is between 100 to 2000 µmole/ml, and more preferably is between 200 to 800 µmole/ml. These are also the preferred ranges of the peptide in the mother milk substitute or artificial mother milk formulation or the pharmaceutical compositions disclosed herein.

Dietary Supplement

Still another aspect of the present invention relates to the use of disclosed peptide as a dietary supplement. That dietary supplement is preferably for oral administration and especially but not limited to administration to newborns, toddlers, and/or infants. A dietary supplement is intended to supplement the diet. The "dietary ingredients" in these products may in addition include: vitamins, minerals, herbs or other botanicals, amino acids, and substances such as enzymes, organ tissues, glandulars, and metabolites. Dietary supplements may be manufactured in forms such as tablets, capsules, softgels, gelcaps, liquids, or powders.

Method of Treatment

Another aspect of the present invention relates to a method of prophylaxis and/or treatment of cancer, an autoimmune disease, a fibrotic disease, an inflammatory disease, a neurodegenerative disease, an infectious disease, a lung disease, a heart and vascular disease or a metabolic disease or any other disease disclosed herein comprising administering to a patient in need thereof a pharmaceutical composition comprising the peptide Ac-Arg-Phe-Met-Trp-Met-Arg-NH$_2$ or salts, hydrates and the deacetylated form thereof in a therapeutically effective amount effective to treat the afore-mentioned disease.

Accordingly, the terms "prophylaxis" or "treatment" includes the administration of the peptide of the present invention to prevent, inhibit, or arrest the symptoms of an infectious disease, an autoimmune disease, a fibrotic disease, an inflammatory disease, a neurodegenerative disease, or a heart and vascular disease. In some instances, treatment with the peptide of the present invention will be done in combination with other protective compounds to prevent, inhibit, or arrest the symptoms of an infectious disease, an autoimmune disease, a fibrotic disease, an inflammatory disease, a neurodegenerative disease, or a heart and vascular disease.

The term "active agent" or "therapeutic agent" as used herein refers to an agent that can prevent, inhibit, or arrest the symptoms and/or progression of an infectious, an autoimmune disease, a fibrotic disease, an inflammatory disease, a neurodegenerative disease, or a heart and vascular disease or any other disease disclosed herein.

The term "therapeutic effect" as used herein, refers to the effective provision of protection effects to prevent, inhibit, or arrest the symptoms and/or progression of an infectious, an autoimmune disease, a fibrotic disease, an inflammatory disease, a neurodegenerative disease, or a heart and vascular disease.

The term "a therapeutically effective amount" as used herein means a sufficient amount of the peptide of the invention to produce a therapeutic effect, as defined above, in a subject or patient in need of treatment.

The terms "subject" or "patient" are used herein mean any mammal, including but not limited to human beings, including a human patient or subject to which the compositions of the invention can be administered. The term mammals include human patients and non-human primates, as well as experimental animals such as rabbits, rats, and mice, and other animals.

The peptide of the present invention can be used for the prophylaxis and/or treatment of cancer, an autoimmune disease, a fibrotic disease, an inflammatory disease, a neurodegenerative disease, an infectious disease, a lung disease, a heart and vascular disease or a metabolic disease or any other disease mentioned herein in combination administration with another therapeutic compound. As used herein the term "combination administration" of a compound, therapeutic agent or known drug with the peptide of the present invention means administration of the drug and the peptide at such time that both the known drug and the peptide will have a therapeutic effect. In some cases this therapeutic effect will be synergistic. Such concomitant administration can involve concurrent (i.e. at the same time), prior, or subsequent administration of the drug with respect to the administration of the peptide of the present invention. A person of ordinary skill in the art would have no difficulty determining the appropriate timing, sequence and dosages of administration for particular drugs and peptide of the present invention.

Definition of Peptide Activity

A peptide is deemed to have therapeutic activity if it demonstrated any one of the following activities listed in a) to g).
a) The peptide could inhibit the activity of an over active biological pathway.
b) The peptide could inhibit the production of an over produced biological molecule.
c) The peptide could inhibit the activity of an over produced biological molecule.
d) The peptide could increase the activity of an under active biological pathway.
e) The peptide could increase the production of an under produced biological molecule.
f) The peptide could mimic the activity of an under produced biological molecule.
g) The peptide could prevent, inhibit, or arrest the symptoms and/or progression of cancer, an infectious disease, an autoimmune disease, a fibrotic disease, an inflammatory disease, a neurodegenerative disease, or a heart and vascular disease or any other disease disclosed herein.

As used herein "inhibition" is defined as a reduction of the activity or production of a biological pathway or molecule activity of between 10 to 100%. More preferably the reduction of the activity or production of a biological pathway or molecule activity is between 25 to 100%. Even more preferably the reduction of the activity or production of a biological pathway or molecule activity is between 50 to 100%.

As used herein "increase" is defined as an increase of the activity or production of a biological pathway or molecule of between 10 to 100%. More preferably the increase of the activity or production of a biological pathway or molecule activity is between 25 to 100%. Even more preferably the increase of the activity or production of a biological pathway or molecule activity is between 50 to 100%.

As used herein "mimic" is defined as an increase in the activity of a biological pathway dependent on the under produced biological molecule of between 10 to 100%. More preferably the increase of the activity of the biological pathway is between 25 to 100%. Even more preferably the increase of the activity the biological pathway is between 50 to 100%.

Peptide

The peptide of the invention was for tested for the activity as a therapeutic agent for the prophylaxis and/or treatment of cancer, an infectious disease, an autoimmune disease, a fibrotic disease, an inflammatory disease, a neurodegenerative disease, or a heart and vascular disease:

peptide having the amino acid sequence:
Ac-Arg-Phe-Met-Trp-Met-Arg-NH$_2$.

Furthermore the present invention relates to the use of the above-mentioned peptide as pharmaceutically active agents in medicine, i.e. as medicament. Advantage of the peptide of the invention is that the peptide is less toxic in comparison to the commonly used drugs for the certain indications mentioned herein and that the peptide have less side effects, can be used for a long term treatment of certain diseases and can be easily administered. Moreover the peptide are selective for certain targets and under physiological conditions no toxic or noxious degradation products are formed."

As used herein, the term "peptide(s)" or "peptide(s) of the invention" shall also refer to salts, deprotected form, acetylated form of the peptide, deacetylated form of the peptide, enantiomers, diastereomers, racemates, prodrugs and hydrates of the above-mentioned peptide. Diastereomers of the peptide are obtained when the stereochemical or chiral center of one or more amino acids is changed. The enantiomer has the opposite stereochemistry at all chiral centers.

The term "prodrug" refers to any precursor compound which is able to generate or to release the above-mentioned peptide under physiological conditions. Such prodrugs, i.e. such precursor molecules are for instance larger peptides which are selectively cleaved in order to form the peptide of the invention. Further prodrugs are protected amino acids having especially protecting groups at the carboxylic acid and/or amino group.

Suitable protecting groups for amino groups are the benzyloxycarbonyl, t-butyloxycarbonyl (BOC), formyl, and acetyl or acyl group. Suitable protecting groups for the carboxylic acid group are esters such as benzyl esters or t-butyl esters.

The present invention also includes the above peptide having amino acid substitutions, deletions, additions, the substitutions and additions including the standard D and L amino acids and modified amino acids such as for example amidated and acetylated amino acids, wherein the therapeutic activity of the base peptide sequence as shown above is maintained.

In the listed peptide sequences "Ac" indicates an acetylated residue and "NH$_2$" indicates an amidated residue, "cyclo" indicates a cyclic peptide, and "D" indicates a D optical isomer. Deacetyled amino or NH-group refers to the free amino (—HH$_2$) group.

TABLE 6

The following abbreviations are used for the common amino acids referred to herein.

| Abbreviation | Amino acid |
| --- | --- |
| Ala | Alanine |
| Arg | Arginine |
| Asn | Asparagine |
| Asp | Aspartic acid (Aspartate) |
| Cys | Cysteine |
| Gln | Glutamine |
| Glu | Glutamic acid (Glutamate) |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Pyl | Pyrrolysine |
| Ser | Serine |
| Sec | Selenocysteine |
| Thr | Threonine |
| Trp | Tryptophan |
| Tyr | Tyrosine |
| Val | Valine |
| Asx | Aspartic acid or Asparagine |
| Glx | Glutamine or Glutamic acid |
| Xaa | Any amino acid |
| Xle | Leucine or Isoleucine |

Some modified amino acids are indicated as follows:
"D-2-Nal" is 2-naphthyl-D-alanine,
"SertBu" is t-butyl serine,
"Azagly" is aza glycine, "Me" is methyl,
Met(O) is methionine sulfoxide,
"Pyr" and "pGlu" are pyroglutamic acid,
"Tyr(SO3H)" is sulphated tyrosine,
"Tyr(Me)" is methyltyrosine,
"NHEt" is ethylamide.

EXAMPLES

The peptide as listed above was tested for activity using the assays described in Examples 1 to 17. The tested peptide is commercially available.

Example 1

HIV-1 Experiments

CEM-SS cells were passaged in T-75 flasks prior to use in the antiviral assay. On the day preceding the assay, the cells were split 1:2 to assure they were in an exponential growth phase at the time of infection. Total cell viability quantification was performed using a hemacytometer and trypan blue exclusion. Cell viability was greater than 95% for the cells to be utilized in the assay. The cells were resuspended at $5 \times 10^4$ cells/ml in tissue culture medium and added to the peptide-containing microtiter plates in a volume of 50 microliters.

The virus used was the lymphocytotropic strain HIV-1$_{IIIB}$. Virus was obtained from NIH AIDS Research and Reference Reagent Program and was grown in CEM-SS cells for the production of stock virus pools. For each assay, a pre-titered aliquot of virus was removed from the freezer (−80° C.) and allowed to thaw slowly to room temperature in a biological safety cabinet. The virus was resuspended and diluted into tissue culture medium such that the amount of virus added to each well in a volume of 50 microliters was the amount determined to give between 85% to 95% cell killing after 6 days post-infection. TCID$_{50}$ calculations by endpoint titration in CEM-SS cells indicated that the multiplicity of infection was approximately 0.01. AZT (nucleoside reverse transcriptase inhibitor; NRTI) and indinavir (protease inhibitor; PI) were used as positive control antiviral compounds.

Plate Format

Each plate contained cell control wells (cells only), virus control wells (cells plus virus), drug cytotoxicity wells (cells plus peptide only), peptide colorimetric control wells (peptide only) as well as experimental wells (peptide—10 micrograms per ml—plus cells plus virus). Samples were evaluated for antiviral efficacy with triplicate measurements and with duplicate measurements to determine cellular cytotoxicity, if detectable.

At assay termination, the plates were stained with the soluble tetrazolium-based dye MTS (CellTiter 96 Reagent, Promega) to determine cell viability and quantify peptide' toxicity. MTS is metabolized by the mitochondrial enzymes of metabolically active cells to yield a soluble formazan product, allowing the rapid quantitative analysis of cell viability and peptide cytotoxicity. This reagent is a stable, single solution that does not require preparation before use. At assay termination, 20-25 microliters of MTS reagent was added per well and the microtiter plates were then incubated for 5 hours at 37° C., and 5% $CO_2$ to assess cell viability. Adhesive plate sealers were used in place of lids, the sealed plates were inverted several times to mix the soluble formazan product and the plate was read spectrophotometrically at 490/560 nm with a Molecular Devices Vmax plate reader.

The overall assay performance was valid based upon judgement of the positive control compounds AZT and indinavir exhibiting the expected levels of antiviral activity. Macroscopic observation of the cells in each well of the microtiter plate confirmed the cytotoxicity results obtained following staining of the cells with the MTS metabolic dye.

Results from HIV Experiments:

| Compound | % CPE reduction in HIV-1 infected CEM-SS cells | % Cell viability |
|---|---|---|
| Ac-Arg-Phe-Met-Trp-Met-Arg-NH$_2$ | 0.0 | 100 |
| AZT (positive control) | 99 | 97 |
| Indinavir (positive control) | 100 | 93 |

Example 2

HBV Experimental Assay System

HepG2-2.2.15 is a stable cell line containing the hepatitis B virus (HBV) ayw strain genome (ATCC Cat. No. CRL-11997). Antiviral compounds blocking any late step of viral replication such as transcription, translation, pregenome encapsidation, reverse transcription, particle assembly and release can be identified and characterized using this cell line. In this assay, an active compound will reduce the production of secreted HBV from cells, measured by utilizing real time quantitative PCR (TaqMan) assay to directly and accurately measure HBV DNA copies. The analysis of this data allows to calculate:

Antiviral activity
Compound Cytotoxicity

HepG2-2.2.15 cells were plated in 96-well microtiter plates. After 16-24 hours the confluent monolayer of HepG2-2.2.15 cells was washed and the medium was replaced with complete medium containing test peptide—10 micrograms per ml—in duplicate. Lamivudine (3TC) was used as the positive control, while media alone was added to the cells as a negative control (virus control). Three days later the culture medium was replaced with fresh medium containing the peptide. Six days following the initial administration of the peptide, the cell culture supernatants was collected, treated with pronase and DNAse and then used in a real-time quantitative TaqMan PCR assay. The PCR-amplified HBV DNA was detected in real-time by monitoring increases in fluorescence signals that result from the exonucleolytic degradation of a quenched fluorescence probe molecule that hybridizes to the amplified HBV DNA. For each PCR amplification, a standard curve was simultaneously generated using dilutions of purified HBV DNA. Antiviral activity was calculated from the reduction in HBV DNA levels (% virus control). A novel dye uptake assay was then employed to measure cell viability, which is used to calculate toxicity (% cell control).

Results from HBV Experiments:

| Compound | % inhibition of HBV replication in HEP G2 cells | % Cell Viability |
|---|---|---|
| Ac-Arg-Phe-Met-Trp-Met-Arg-NH$_2$ | 46.8 | 100 |
| 3TC (positive control) | 92.0 | 95.8 |

Example 3

HCMV Experimental Assay System

MRC-5 cells (human embryonal lung fibroblasts) were obtained from the American Type Culture Collection (ATCC CCL-171; Rockville, Md.) and grown in Eagle's Minimum Essential Medium with Earle's BSS (EMEM) supplemented with 10% fetal bovine serum (FBS), 0.1 mM non-essential amino acids, 1.0 mM sodium pyruvate, 2.0 mM L-Glutamine, 100 units/ml Penicillin and 100 micrograms/ml Streptomycin. Cells were split twice a week 1:2.

HCMV strain AD169 was obtained from ATCC (ATCC VR-538). Virus stocks were prepared by infecting 80% confluent MRC-5 cells at a minimal multiplicity of infection in MRC-5 growth medium containing 2% FBS. Monolayers were incubated at 37° C., 5% $CO_2$ until 90%-95% viral cytopathic effect (CPE) was observed (10-13 days). Culture medium was then collected from the cells, centrifuged at low speed to remove cellular debris, aliquoted in 1 ml volumes and stored at −80° C. as stock virus.

MRC-5 cells were seeded at 75,000 cells/well in 24 well plates using MRC-5 growth medium. The plates were incubated overnight at 37° C., 5% $CO_2$. The following day, media was removed and 100 plaque forming units (pfu) of HCMV was added to the wells. Virus was allowed to adsorb onto the cells for 1 hour at 37° C., 5% $CO_2$. Peptide was diluted—10 micrograms per ml—in assay medium containing 0.5% Methylcellulose.

After the incubation period, 1 ml of each peptide solution was added to the wells without aspirating the virus inoculums. The plates were incubated for 7-10 days to allow for plaque formation. Ganciclovir was used as positive control. Cultures were examined microscopically and toxicities were noted. The media was the aspirated from the wells and the cells were fixed and stained using 20% methanol containing Crystal Violet followed by enumeration of plaques by microscopic inspection.

For cytotoxicity testing, MRC-5 cells were seeded at 2,500 cells/well in 96 well plates using growth medium. The plates were incubated overnight at 37° C., 5% $CO_2$. The following day, peptide was added and tested in duplicates. After a 6 days incubation period, cell viability was measured using CellTiter 96 Solution (Promega). Plates were incubated for additional 4 hours at 37° C. Adhesive plate sealers were used in place of lids, the sealed plates were inverted several times to mix the soluble formazan product and the plate was read spectrophotometrically at 490/560 nm with a Molecular Devices Vmax plate reader.

The overall assay performance was valid based upon judgement of the positive control compound Ganciclovir exhibiting the expected levels of antiviral activity. Macroscopic observation of the cells in each well of the microtiter plate confirmed the cytotoxicity results obtained following staining of the cells with the MTS metabolic dye.

Results from HCMV Assay:

| Compound | % plaque reduction | % Cell viability |
| --- | --- | --- |
| Ac-Arg-Phe-Met-Trp-Met-Arg-$NH_2$ | 0.0 | 84.0 |
| Ganciclovir (positive control) | 100 | 100 |

Example 4

Methicillin Resistant *Staphylococcus Aureus* (MRSA) Assay

The antibacterial assay was conducted using clear, U-bottom 96-well microtiter plates. Cation-adjusted Mueller-Hinton Broth (MHB) was used for testing MRSA. The peptide of the invention (0.1 ml of each—10 micrograms per ml—) was dispensed into wells in duplicate. Then the wells were inoculated with $5 \times 10^5$ CFU/mL MRSA in 0.1 ml volume. For control purposes, each plate included 4 wells containing media without bacterial inoculum and 4 wells containing medium with inoculum but without peptide. The plates were incubated for 12 h at 37° C., and read visually 18-24 hours post-incubation. Growth control of MRSA was examined first to determine adequacy of media preparations and growth conditions. Acceptable growth is defined as $\geq 2$ mm wide button of cells at the bottom of each sample well, or obvious turbidity in the culture supernatant. Test wells were examined and scored as positive/negative for activity. A positive score for activity is based on complete inhibition of macroscopic growth of the test MRSA.

Results from MRSA Assay:

| Compound | % inhibition |
| --- | --- |
| Ac-Arg-Phe-Met-Trp-Met-Arg-$NH_2$ | 0.0 |

Example 5

*Pseudomonas aeruginosa* Assay

The antibacterial assay was conducted using clear, U-bottom 96-well microtiter plates. Cation-adjusted Mueller-Hinton Broth (MHB) was used for testing *Pseudomonas aeruginosa*. The peptide of the invention (0.1 ml of each—10 micrograms per ml—) was dispensed into wells in duplicate. Then the wells were inoculated with $5 \times 10^5$ CFU/mL *Pseudomonas aeruginosa* in 0.1 ml volume. For control purposes, each plate included 4 wells containing media without bacterial inoculum and 4 wells containing medium with inoculum but without peptide. The plates were incubated for 12 h at 37° C., and read visually 18-24 hours post-incubation. Growth control of *Pseudomonas aeruginosa* was examined first to determine adequacy of media preparations and growth conditions. Acceptable growth is defined as $\geq 2$ mm wide button of cells at the bottom of each sample well, or obvious turbidity in the culture supernatant. Test wells were examined and scored as positive/negative for activity. A positive score for activity is based on complete inhibition of macroscopic growth of the test *Pseudomonas aeruginosa*.

Results from *Pseudomonas aeruginosa* Assay:

| Compound | % inhibition |
| --- | --- |
| Ac-Arg-Phe-Met-Trp-Met-Arg-$NH_2$ | 0.0 |

Example 6

*Streptococcus pneumoniae* Assay

The antibacterial assay was conducted using clear, U-bottom 96-well microtiter plates. Cation-adjusted Mueller-Hinton Broth (MHB) was used for testing *Streptococcus pneumoniae*. The peptide of the invention (0.1 ml of each—10 micrograms per ml—) was dispensed into wells in duplicate. Then the wells were inoculated with 5×10⁵ CFU/mL *Streptococcus pneumoniae* in 0.1 ml volume. For control purposes, each plate included 4 wells containing media without bacterial inoculum and 4 wells containing medium with inoculum but without peptide. The plates were incubated for 12 h at 37° C., and read visually 18-24 hours post-incubation. Growth control of *Streptococcus pneumoniae* was examined first to determine adequacy of media preparations and growth conditions. Acceptable growth is defined as ≧2 mm wide button of cells at the bottom of each sample well, or obvious turbidity in the culture supernatant. Test wells were examined and scored as positive/negative for activity. A positive score for activity is based on complete inhibition of macroscopic growth of the test *Streptococcus pneumoniae*.

Results from *Streptococcus pneumoniae* Assay:

| Compound | % inhibition |
|---|---|
| Ac-Arg-Phe-Met-Trp-Met-Arg-NH$_2$ | 0.0 |

Example 7

*Mycobacterium tuberculosis* Assay

The antibacterial assay was conducted using clear, U-bottom 96-well microtiter plates. Middlebrook 7H12 assay medium was used for testing drug-resistant *Mycobacterium tuberculosis*. The peptide of the invention (0.1 ml of each—10 micrograms per ml—) was dispensed into wells in duplicate. Then the wells were inoculated with 5×10⁵ CFU/mL *Mycobacterium tuberculosis* in 0.1 ml volume. For control purposes, each plate included 4 wells containing media without bacterial inoculum and 4 wells containing medium with inoculum but without peptide. The plates were incubated for seven days at 37° C., and read visually thereafter. Growth control of *Mycobacterium tuberculosis* was examined first to determine adequacy of media preparations and growth conditions. Acceptable growth is defined as ≧2 mm wide button of cells at the bottom of each sample well, or obvious turbidity in the culture supernatant. Test wells were examined and scored as positive/negative for activity. A positive score for activity is based on complete inhibition of macroscopic growth of the test *Mycobacterium tuberculosis*. The drug-resistant *Mycobacterium tuberculosis* that was used in the assay is resistant against following medicaments: para-aminosalicylic acid (PAS), streptomycin and isoniazid (INH).

Results from *Mycobacterium tuberculosis* Assay:

| Compound | % inhibition |
|---|---|
| Ac-Arg-Phe-Met-Trp-Met-Arg-NH$_2$ | 100.0 |

Example 8

Cell Cycle Assay

Human A549 cells (carcinomic human alveolar basal epithelial cells) were utilized in the experiments employing the Propidium iodide cell cycle assay. The eukaryotic cell cycle is a series of events that take place in a cell leading to its replication. The regulation of the cell cycle involves steps crucial to the cell, including detecting and repairing genetic damage, and provision of various checks to prevent uncontrolled cell division. The molecular events that control the cell cycle are ordered and directional; that is, each process occurs in a sequential fashion. The cell cycle consists of four distinct phases: $G_1$ phase, S phase, $G_2$ phase (collectively known as interphase) and M phase. M phase is itself composed of two tightly coupled processes: mitosis, in which the cell's chromosomes are divided between the two daughter cells, and cytokinesis, in which the cell's cytoplasm divides forming distinct cells. Activation of each phase is dependent on the proper progression and completion of the previous one. Cells that have temporarily or reversibly stopped dividing are said to have entered a state of quiescence called $G_o$ phase. The relatively brief M phase consists of nuclear division and cytoplasmic division. The first phase within interphase, from the end of the previous M phase till the beginning of DNA synthesis is called $G_1$ (G indicating gap or growth). During this phase the biosynthetic activities of the cell resume at a high rate. This phase is marked by synthesis of various enzymes that are required in S phase, mainly those needed for DNA replication. The ensuing S phase starts when DNA synthesis commences; when it is complete, all of the chromosomes have been replicated. The cell then enters the $G_2$ phase, which lasts until the cell enters mitosis. Significant protein synthesis occurs during this phase, mainly involving the production of microtubules, which are required during the process of mitosis. Inhibition of protein synthesis during $G_2$ phase prevents the cell from undergoing mitosis.

Disregulation of the cell cycle components may lead to tumor formation.

Propidium iodide is an intercalating agent and a fluorescent molecule that can be used to stain DNA. Cells were incubated for 24 hours with test peptide—10 micrograms per ml—or left untreated. After that cells were trypsinized, suspended in medium +10% FCS, centrifuged (1000 rpm, 5 min), and the cell pellet resuspended in PBS (1 ml). The cells were pipetted into 2.5 ml absolute EtOH (final concentration approx. 70%) and incubated on ice for 15 min. Thereafter, cells were pelleted at 1500 rpm for 5 min and resuspended in Propidium iodide solution in PBS. After incubation for 40 min at 37° C., cells were analyzed in the FACS.

Results from Cell Cycle Assay:

| | Cell cycle analysis | | |
|---|---|---|---|
| Compound | G0/G1 | S | G2/M |
| Ac-Arg-Phe-Met-Trp-Met-Arg-NH$_2$ | 59.2 | 32.7 | 8.2 |

Example 9

T Cell Proliferation Assay

Human Peripheral Blood Mononuclear Cells (PBMC) were obtained from normal human donors. The T cell proliferation was induced by stimulation of the cells with the T cell mitogen phytohemagglutinin (PHA), either in the absence (positive proliferation control), or in the presence of test peptide—10 micrograms per ml—to examine their effects on the T cell proliferating response. $10^5$/well PBMC were plated in 96-well microtiter plates and assayed in duplicate with the peptide. Cell cultures were incubated at 37° C. for 3 days in a 5% $CO_2$ incubator and were thereafter pulsed with 1 microCi/well $^3$H-thymidine for additional 12 hours of culture. At the end of incubation time, the plates were harvested and the cells counted by liquid scintillation for the incorporation of $^3$H-thymidine as a measure of T cell proliferation.
Results from T cell Proliferation Assay:

| Compound | % of PHA induced control |
|---|---|
| Ac-Arg-Phe-Met-Trp-Met-Arg-$NH_2$ | 109.1 |

Example 10

B Cell Proliferation Assay

Human Peripheral Blood Mononuclear Cells (PBMC) were obtained from normal human donors. The B cell proliferation was induced by stimulation of the cells with the B cell mitogen *Staphylococcus aureus* Cowans I (SAC) plus Interleukin-2, either in the absence (positive proliferation control), or in the presence of test peptide—10 micrograms per ml—to examine their effects on the B cell response. $10^5$/well PBMC were plated in 96-well microtiter plates and assayed in duplicate with the peptide. Cell cultures were incubated at 37° C. for 3 days in a 5% $CO_2$ incubator and were thereafter pulsed with 1 microCi/well $^3$H-thymidine for additional 12 hours of culture. At the end of incubation time, the plates were harvested and the cells counted by liquid scintillation for the incorporation of $^3$H-thymidine as a measure of B cell proliferation.
Results from B Cell Proliferation Assay:

| Compound | % of SAC/IL2 induced control |
|---|---|
| Ac-Arg-Phe-Met-Trp-Met-Arg-$NH_2$ | 106.3 |

Example 11

Phagocytosis Assay

RAW 264.7 (Mouse leukaemic monocyte macrophage cell line) cells were obtained from ATCC and grown in RPMI 1640 medium containing 10% FBS. Cells were incubated in 12×75 mm tubes at 37° C. with test peptide—10 micrograms per ml—for 30 min prior to adding Fluorescein-labeled *Escherichia coli* bacteria as the agent to be ingested. After the cells were incubated for additional 60 min at 37° C. and allowed to ingest the Fluorescein-labeled *Escherichia coli* bacteria, cells were fixed with 1% paraformaldehyde. The samples were then analyzed by flow cytometry to determine the amount of phagocytosis as a function of brightness (the greater the phagocytic activity, the more fluorescence in the macrophage population). Data are reported as % positive and the mean fluorescence intensity (MFI) of positively stained cells.
Results from Phagocytosis Assay:

| Compound | % of control phagocytosis |
|---|---|
| Ac-Arg-Phe-Met-Trp-Met-Arg-$NH_2$ | 105.9 |

Example 12

Apoptosis Induction Assay

Human A549 cells (carcinomic human alveolar basal epithelial cells) were utilized in the experiments employing the Annexin-5 apoptosis assay. Annexin-5 is a member of a highly conserved protein family that binds acidic phospholipids in a calcium-dependent manner. Annexin-5 possesses a high affinity for phosphatidylserine. Phosphatidylserine is translocated from the inner side of the plasma membrane to the outer layer when cells undergo death by apoptosis or cell necrosis and serves as a signal by which cell destined for death are recognized by phagocytes. Test peptide—10 micrograms per ml—were exposed for 24 hours to the A549 cells before they were analyzed for signs of apoptosis.
Results from Apoptosis Induction Assay:

| Compound | % of induction |
|---|---|
| Ac-Arg-Phe-Met-Trp-Met-Arg-$NH_2$ | 1.2 |

Example 13

Apoptosis Prevention Assay

Human A549 cells (carcinomic human alveolar basal epithelial cells) were utilized in the experiments employing the Annexin-5 apoptosis assay. Annexin-5 is a member of a highly conserved protein family that binds acidic phospholipids in a calcium-dependent manner. Annexin-5 possesses a high affinity for phosphatidylserine. Phosphatidylserine is translocated from the inner side of the plasma membrane to the outer layer when cells undergo death by apoptosis or cell necrosis and serves as a signal by which cell destined for death are recognized by phagocytes. A549 cells were pre-treated for 30 min with test peptide—10 micrograms per ml—followed by the exposure to C2 ceramide. Ceramide mediates cell apoptosis through the activation of the mitogen activating protein kinase (MAPK) and the stress activated kinase (JNK/SAPK). C2 ceramide is a synthetic, membrane soluble analog of ceramide.

Results from Apoptosis Prevention Assay:

| Compound | % prevention of ceramide induced apoptosis |
|---|---|
| Ac-Arg-Phe-Met-Trp-Met-Arg-NH$_2$ | 0.0 |

Example 14

Th1/Th2 Cytokine Profiling Assay

The Balb/c mice (originated in 1923, it is a popular strain and is used in many different research disciplines. Also classified as an inbred from the production of 20 or more successive brother-sister matings, the Balb/c mouse is albino and small in size) were immunized on Days 1, 15, and 29 with Ovalbumin (Ovalbumin is the main protein found in egg white, commonly used to stimulate an immunological reaction in test animals) in PBS (5 micrograms/injection). On day 50, spleens of the mice were harvested (3 weeks after last boost with Ovalbumin). Cells were cultured ($2 \times 10^5$/well in triplicate) and incubated with culture medium or test peptide—10 micrograms per ml—for 30 min. Thereafter, additional Ovalbumin was added to the cells at 10 micrograms/ml for in vitro restimulation of the cells. 72 hours later, cell supernatants were harvested and assayed using the Becton Dickinson Mouse Th1/Th2 Cytokine CBA Kit. This kit can be used to measure Interleukin-2 (IL-2), Interleukin-4 (IL-4), Interleukin-5 (IL-5), Interferon-γ (IFN-γ), and Tumor Necrosis Factor-α (TNF-α) protein levels in a single sample. The kit performance has been optimized for analysis of physiologically relevant concentrations (μg/ml levels) of specific cytokine proteins in tissue culture supernatants and serum samples. Results from Th1/Th2 Cytokine Assay:

TABLE 2

| Compound | TNF-a spleen cells; TH1 response (% of control) | INFγ spleen cells; TH1 response (% of control) | IL-2 spleen cells (% of control) | IL-4 spleen cells; TH2 response (% of control) | IL-5 spleen cells; TH2 response (% of control) |
|---|---|---|---|---|---|
| Ac-Arg-Phe-Met-Trp-Met-Arg-NH$_2$ | 118.8 | 218.6 | 156.5 | 156.2 | 93.8 |

Example 15

TNF Alpha Production Assay

Human Peripheral Blood Mononuclear Cells (PBMC) were obtained from normal human donors. The macrophages were prepared by adherence of PBMC to the plastic wells of the plates. After 8 days in culture in the presence of recombinant human macrophage-colony stimulating factor at 2 ng/ml, differentiated macrophages were preincubated with test peptide—10 micrograms per ml—for 30 min, followed by in-well stimulation by the addition of lipopolysaccharide at a final concentration of 200 ng/ml. Not stimulated macrophages served as negative background control.

After overnight incubation, supernatants from the control and LPS-stimulated cultures were harvested and assayed for TNF alpha production employing a TNF alpha specific ELISA.

Results from TNF Alpha Assay:

| Compound | % of LPS induction |
|---|---|
| Ac-Arg-Phe-Met-Trp-Met-Arg-NH$_2$ | 149.8 |

Example 16

Endothelial Cell Migration Assay

Endothelial cell migration is a prerequisite for the process of neo-vascularization or angiogenesis which is crucial for on-site recruitment of blood vessel formation. Primary Human endothelial cells (HUVEC) were seeded in insert chambers with 3 micrometer pore size of multi-transwell plate for 6 hours at 37° C. in Endothelial Cell Basal Medium (EBM) supplemented with 0.1% bovine serum albumin. Thereafter, designated concentration of test peptide—10 micrograms per ml—was added in duplicate wells. The endothelia were allowed to migrate for 22 hours at 37° C., then, migrated cells were fixed and stained with Hoechst 33342 dye. Images of 3 fields per insert were taken and the number of migrated cells per field were quantified using the ImageProPlus software. Data were analyzed for the average number of the migrated cells and standard deviation of six data points for each treatment condition. Active test peptide against HUVEC migration was determined based on 50% inhibition of migrated cells as compared with the control. Statistic p values were computed using the Student's t-test.

Results from Endothelial Cell Migration Assay:

| Compound | % inhibition of migration |
|---|---|
| Ac-Arg-Phe-Met-Trp-Met-Arg-NH$_2$ | −15 |

Example 17

Endothelial Tube Formation Assay

The endothelial tube formation assay is based on the ability of endothelial cells to form three-dimensional capillary-like tubular structures when cultured on a gel of basement membrane extract. The endothelial tube formation assay represents a powerful model for studying inhibition and induction of angiogenesis. Pre-labeled HUVEC with Calcein AM were seeded in a 96-well culture plate coated with extracellular matrix (Chemicon international Cat. ECM625) and treated with test peptide—10 micrograms per ml—in full growth medium. Positive control was vehicle only. The endothelial cells were allowed to form tubes for 20 hours and were then examined under an inverted fluorescent microscope. Duplicate wells for each treatment were photographed and quantitatively analyzed for an average tubule length using image analysis software ImageProPlus. Raw data were expressed as average tubule lengths in pixels ±standard deviation. Statistic p values were computed using the Student's t-test.

Results from Endothelial Tube Formation Assay:

| Compound | % inhibition of tube formation |
|---|---|
| Ac-Arg-Phe-Met-Trp-Met-Arg-$NH_2$ | 23 |

Example 18

Mother Milk Formulation

Methods to prepare mother milk or artificial mother milk formulations or mother milk substitutes are described in WO03043429, U.S. Pat. No. 5,962,062, WO0030461, EP0527283, EP0832565

One example of an artificial mother milk or mother milk substitute formulation is provided in the following while also the other formulations disclosed in the above mentioned references can be used and are included herewith by reference.

The milk substitute contains, by weight, approximately 15% skimmed milk solids, approximately 75% demineralized water, approximately 9% soya oil, approximately 0.02% of carrageenates, 0.2% lecithin, and approximately 0.2% of disodium hydrogenphosphate.

In a first step, the solubilizing aqueous medium is produced, comprises, by weight, approximately 75% of water, approximately 0.02% of carrageenate and approximately 0.2% of disodium hydrogenphosphate.

The skimmed milk powder is then added to the solution for 10 min at 60° C. and dissolved in the liquid.

Then soya oil and lecithin are added to the milk substitute composition at 60° C. The milk composition is allowed to stand 30 min at 55° C. After pasteurization, the peptide of the invention is added in liquid or powder form in such a quantity that the milk composition obtained comprises an amount of 5-50 micrograms, preferably 10-40 micrograms per 100 ml of milk composition. Optionally peptide 2 could be added in similar or smaller amounts to the obtained composition.

Example 19

Gel Formulation 0.5 g of peptide
1.6 g of isopropanol
1.0 g of glycerol
1.6 g of polyoxyethylene-polyoxypropylene copolymer 12500 (Pluronic F127)
5.3 g of water are mixed for 10 minutes and then heated to 85° C. under continuous stirring for 15 minutes. The solution is cooled to room temperature under stirring. During the cooling phase the solution begins to gel at a temperature of about 45° C. to form a clear gel. The gel contains 5% of the peptide combination for medical use. Optionally peptide 2 could be added in an amount form 0.01 to 0.5 g.

Example 20

Lotion Formulation 0.5 g of peptide
1.9 g of isopropanol
1.0 g of dimethylisosorbide
1.0 g of polyoxyethylene-polyoxypropylene copolymer 12500 (Pluronic F127)
5.6 g of water are stirred and heated at 50° C., until a clear solution has been formed. Then the composition is cooled to room temperature under stirring. The lotion contains 5% of peptide combination for medical use. Optionally peptide 2 could be added in an amount form 0.01 to 0.5 g.

---

The invention claimed is:

1. A method of treatment of *Mycobacterium tuberculosis* infection, the method comprising,
administering to a patient in need thereof, a therapeutically effective amount of a pharmaceutical compostion comprising a peptide consisting of the sequence Ac-Arg-Phe-Met-Trp-Met-Arg-NH$_2$ (SEQ ID NO: 1) or salts thereof, wherein administration of the pharmaceutical composition treats said diseases.

2. The method of claim 1, wherein the peptide is administered by intravenous administration, oral administration, or administration by inhalation.

3. The method of claim 1, wherein the peptide is administered as a lyophilized formulation or as a buffered liquid formulation.

* * * * *